United States Patent
Essam et al.

(10) Patent No.: US 12,380,966 B2
(45) Date of Patent: Aug. 5, 2025

(54) AA2CDS: PRE-TRAINED AMINO ACID-TO-CODON SEQUENCE MAPPING ENABLING EFFICIENT EXPRESSION AND YIELD OPTIMIZATION

(71) Applicant: Proteinea, Inc., Newton, MA (US)

(72) Inventors: Hazem Essam, Alexandria (EG); Hosna Eltarras, Cairo (EG); Wafaa Ashraf Salah-Eldin, New Cairo (EG); Mohamed Soudy, Cairo (EG); Ahmed Saleh, New Cairo (EG); Walid Moustafa, Cairo (EG); Ahmed Eid Zoheir, Beni Suef (EG); Mohamed Ashraf Elkerdawy, New Cairo (EG)

(73) Assignee: Proteinea, Inc., Newton, MA (US)

( * ) Notice: Subject to any disclaimer, the term of this patent is extended or adjusted under 35 U.S.C. 154(b) by 0 days.

(21) Appl. No.: 18/769,001

(22) Filed: Jul. 10, 2024

(65) Prior Publication Data

US 2025/0022540 A1 Jan. 16, 2025

Related U.S. Application Data

(60) Provisional application No. 63/616,896, filed on Jan. 2, 2024, provisional application No. 63/525,735, filed on Jul. 10, 2023.

(51) Int. Cl.
*G06N 3/123* (2023.01)
*G16B 40/20* (2019.01)

(52) U.S. Cl.
CPC ............ *G16B 40/20* (2019.02); *G06N 3/123* (2013.01)

(58) Field of Classification Search
CPC ................................ G06N 3/123; G16B 40/20
See application file for complete search history.

(56) References Cited

U.S. PATENT DOCUMENTS

| | | | |
|---|---|---|---|
| 2022/0172055 A1 | 6/2022 | Bileschi et al. | |
| 2024/0112751 A1* | 4/2024 | Dutta | G16B 40/20 |
| 2024/0120022 A1* | 4/2024 | Senior | G06N 3/045 |

FOREIGN PATENT DOCUMENTS

| | | |
|---|---|---|
| CN | 113851190 B | 12/2021 |
| CN | 116153402 A | 5/2023 |

(Continued)

OTHER PUBLICATIONS

Elnaggar et al., ProtTrans: Towards Cracking the Language of Life's Code Through Self-Supervised Learning, IEEE Trans. Pattern Analysis & Machine Intelligence, vol. 14, No. 8, Aug. 2021. (Year: 2021).*

(Continued)

*Primary Examiner* — Marshall L Werner
(74) *Attorney, Agent, or Firm* — Flagship Patents; Stephanie Backovic; Sikander M. Khan

(57) ABSTRACT

Systems, methods, and apparatus for generating a DNA/gene sequence output, given a protein sequence input. In one aspect, the protein-to-DNA mapping system includes a protein language model (embedder) that generates a high-dimensional protein embedding from a low-dimensional protein sequence input; and the system includes a protein-to-DNA translator that processes the protein embedding and generates a DNA sequence output, based on the protein embedding. The protein-to-DNA translator is a neural network (e.g., a Seq2Seq model) and is configured with translation coefficients that may be trained with a training dataset, comprising the training protein and DNA embeddings. Training the translation coefficients can include supervised learning that maps the protein embedding (input) to a DNA sequence (target). The systems, methods, and apparatus may increase protein yield/expression, improve protein functionality, enhance gene therapy efficacy, streamline synthetic (Continued)

biology design, and/or broaden functional genomics studies, all leading to reduced costs, better performance, and increased accessibility.

18 Claims, 26 Drawing Sheets
(9 of 26 Drawing Sheet(s) Filed in Color)

(56) References Cited

FOREIGN PATENT DOCUMENTS

| | | |
|---|---|---|
| CN | 116246716 A | 6/2023 |
| CN | 117352049 A | 1/2024 |
| CN | 117497092 A | 2/2024 |
| CN | 117766019 A | 3/2024 |
| CN | 117976048 A | 5/2024 |
| WO | 2004053766 A1 | 6/2004 |

OTHER PUBLICATIONS

Li et al., OPTIMUS: Organizing Sentences via Pre-trained Modeling of a Latent Space, Oct. 2020. (Year: 2020).*

Le et al., A Transformer Architecture Based on BERT and 2D Convolutional Neural Network to Identify DNA Enhancers from Sequence Information, Feb. 2021. (Year: 2021).*

Gankin et al., Species-Aware DNA Language Modeling, Jan. 2023. (Year: 2023).*

Marin et al., Gene Finding Revisited: Improved Robustness Through Structured Decoding From Learning Embeddings, Feb. 2023 (Year: 2023).*

Dutta et al., U.S. Appl. No. 63/411,581 Provisional for 20240112751, Sep. 2022. (Year: 2022).*

Bhushan Mohanraj, Dr. Chao Lu, Dr. Ryan Urbanowicz, CodOpt: Enhancing Drug and Vaccine Development byUsing Deep Learning and Natural-Language Processingto Optimize Recombinant Codon Sequences via a Host-Independent Data Pipeline, Mar. 19, 2023, 36 pages.

Carlos Outeiral, Charlotte M. Deane, Codon language embeddings provide strong signals for protein engineering, Dec. 19, 2022, 27 pages.

Constant, David & Gutierrez, Jahir & Sastry, Anand & Viazzo, Rebecca & Smith, Nicholas & Hossain, Jubair & Spencer, David & Carter, Hayley & Ventura, Abigail & Louie, Michael & Kohnert, Christa & Consbruck, Rebecca & Bennett, Joshua & Crawford, Kenneth & Sutton, John & Morrison, Anneliese & Steiger, Andrea & Jackson, Kerianne & Stanton, Jennifer & Gander, Miles. (Feb. 2023). Deep learning-based codon optimization with large-scale synonymous variant datasets enables generalized tunable protein expression, 56 pages.

Haoran Gong, Jianguo Wen, Ruihan Luo, Yuzhou Feng, JingJing Guo, Hongguang Fu and Xiaobo Zhou, Integrated mRNA sequence optimization using deep learning, Briefings in Bioinformatics, 2023, 24(1), 1-11, 11 pages.

Hugo Dalla-Torre, Liam Gonzalez, Javier Mendoza-Revilla, Nicolas Lopez Carranza, Adam Henryk Grzywaczewski, Francesco Oteri, Christian Dallago, Evan Trop, Hassan Sirelkhatim, Guillaume Richard, Marcin Skwark, Karim Beguir, Marie Lopez, Thomas Pierrot, The Nucleotide Transformer: Building and Evaluating Robust Foundation Models for Human Genomics, Mar. 21, 2023, 40 pages.

Jeliazko R. Jeliazkov, Maxim V. Shapovalov, Diego del Alamo, Matt C. Sternke, and Joel D. Karpiak, Agile Language Transformers for Recombinant Protein Expression Optimization, Machine Learning for Structural Biology Workshop, NeurIPS 2022, 7 pages.

Maxim Zvyagin, Alexander Brace, Kyle Hippe, Yuntian Deng, Bin Zhang, Cindy Orozco Bohorquez, Austin Clyde, Bharat Kale, Danilo Perez-Rivera, Heng Ma, Carla M. Mann, Michael Irvin, J. Gregory Pauloski, Logan Ward, Valerie Hayot-Sasson, Murali Emani, Sam Foreman, Zhen Xie, Diangen Lin, Maulik Shukla, Weili Nie, Josh Romero, Christian Dallago, Arash Vahdat, Chaowei Xiao, Thomas Gibbs, Ian Foster, James J. Davis, Michael E. Papka, Thomas Brettin, Rick Stevens, Anima Anandkumar, Venkatram Vishwanath, Arvind Ramanathan, GenSLMs: Genome-scale language.

Prior-art Search for AA2DNA: Amino Acid-to-DNA Sequence Mapping Enabling Efficient Protein Expression and Yield Optimization, 17 pages.

Yanrong Ji, Zhihan Zhou, Han Liu, Ramana V. Davuluri, DNABERT: pre-trained Bidirectional Encoder Representations from Transformers model for DNA-language in genome, Bioinformatics, 37(15), 2021, 2112-2120, Feb. 4, 2021, 9 pages.

Žiga Avsec, Vikram Agarwal, Daniel Visentin, Joseph R Ledsam, Agnieszka Grabska-Barwinska,Yannis Assael, John Jumper, Pushmeet Kohli, David R Kelley, Effective gene expressionintegrating long-range interactions, Oct. 2021; 18(10):1196-1203, 24 pages.

* cited by examiner

FOLD-CHANGE IN PROTEIN EXPRESSION LEVEL ACROSS 5 mAb PROTEINS (each with at least two variants) AND ACROSS 4 VHH PROTEINS (each with three variants) IN CHO CELLS

| Cell-line | Protein Class | Protein Index | Yield (mg/L) | Fold Change per Variant in reference to WT |
|---|---|---|---|---|
| CHO | mAb | mAb4-1 WT | 45.372 | N/A |
| | | mAb4-1.1 | 326.38 | 7.193 |
| | | mAb4-1.2 | 128.304 | 2.828 |
| | | mAb4-2 WT | 167.766 | N/A |
| | | mAb4-2.1 | 282.344 | 1.683 |
| | | mAb4-2.2 | 227.316 | 1.355 |
| | | mAb4-2.3 | 288.596 | 1.720 |
| | | mAb4-3 WT | 1.268 | N/A |
| | | mAb4-3.1 | 82.519 | 65.078 |
| | | mAb4-3.2 | 2.976 | 2.347 |
| | | mAb4-3.3 | 33.062 | 26.074 |
| | | mAb4-4 WT | 97.252 | N/A |
| | | mAb4-4.1 | 81.227 | 0.835 |
| | | mAb4-4.2 | 36.146 | 0.372 |
| | | mAb4-4.3 | 127.984 | 1.316 |
| | | mAb4-8 WT | 5.141 | N/A |
| | | mAb4-8.1 | 206.34 | 40.136 |
| | | mAb4-8.2 | 164.22 | 31.943 |
| | | mAb4-8.3 | 51.768 | 10.070 |
| Cell-line | Protein Class | Protein Index | Yield (mg/L) | Fold Change per Variant in reference to WT |
| CHO | VHH | VHH4-1 WT | 441.152 | N/A |
| | | VHH4-1.1 | 427.112 | 0.968 |
| | | VHH4-1.2 | 474.796 | 1.076 |
| | | VHH4-1.3 | 483.14 | 1.095 |
| | | VHH4-2 WT | 311.568 | N/A |
| | | VHH4-2.1 | 425.536 | 1.366 |
| | | VHH4-2.2 | 423.44 | 1.359 |
| | | VHH4-2.3 | 409.644 | 1.315 |
| | | VHH4-3 WT | 73.828 | N/A |
| | | VHH4-3.1 | 103.148 | 1.397 |
| | | VHH4-3.2 | 116.736 | 1.581 |
| | | VHH4-3.3 | 66.308 | 0.898 |
| | | VHH4-5 WT | 160.564 | N/A |
| | | VHH4-5.1 | 286.24 | 1.783 |
| | | VHH4-5.2 | 259.968 | 1.619 |
| | | VHH4-5.3 | 300.672 | 1.873 |

FIG. 24

**FOLD-CHANGE IN PROTEIN EXPRESSION LEVEL
ACROSS 5 VHH PROTEINS (each with three variants) IN HEK293 CELLS**

| Cell line | Protein Class | Protein Index | Yield (mg/L) | Fold Change per Variant in reference to WT |
|---|---|---|---|---|
| HEK293 | VHH | VHH4-1 WT | 102.34 | N/A |
| | | VHH4-1.1 | 253.89 | 2.47 |
| | | VHH4-1.2 | 34 | 0.33 |
| | | VHH4-1.3 | 447.06 | 4.37 |
| | | VHH4-1.4 | 52.44 | 0.51 |
| | | VHH4-1.5 | 91.5 | 0.89 |
| | | VHH4-1.6 | 80.15 | 0.78 |
| | | VHH4-1.7 | 130.76 | 1.28 |
| | | VHH4-1.8 | 282.32 | 2.76 |
| | | VHH4-1.9 | 25.571 | 0.25 |
| | | VHH4-2 WT | 327.11 | N/A |
| | | VHH4-2.1 | 343.87 | 1.05 |
| | | VHH4-2.2 | 459.65 | 1.41 |
| | | VHH4-2.3 | 374.78 | 1.15 |
| | | VHH4-2.4 | 355.67 | 1.09 |
| | | VHH4-2.5 | 398.93 | 1.22 |
| | | VHH4-2.6 | 369.46 | 1.13 |
| | | VHH4-2.7 | 354.07 | 1.08 |
| | | VHH4-2.8 | 352.15 | 1.08 |
| | | VHH4-2.9 | 394.62 | 1.21 |
| | | VHH4-3 WT | 26.279 | N/A |
| | | VHH4-3.1 | 87.13 | 3.32 |
| | | VHH4-3.2 | 55.71 | 2.12 |
| | | VHH4-3.3 | 53.16 | 2.02 |
| | | VHH4-3.4 | 16.841 | 0.64 |
| | | VHH4-3.5 | 2.089 | 0.08 |
| | | VHH4-3.6 | 20.236 | 0.77 |
| | | VHH4-3.7 | 42.35 | 1.61 |
| | | VHH4-3.8 | 43.92 | 1.67 |
| | | VHH4-3.9 | 4.385 | 0.17 |
| | | VHH4-4 WT | 51.7 | N/A |
| | | VHH4-4.1 | 106.72 | 2.06 |
| | | VHH4-4.2 | 125.25 | 2.42 |
| | | VHH4-4.3 | 153.27 | 2.96 |
| | | VHH4-4.4 | 87.21 | 1.69 |
| | | VHH4-4.5 | 89.07 | 1.72 |
| | | VHH4-4.6 | 81.28 | 1.57 |
| | | VHH4-4.7 | 37.3 | 0.72 |
| | | VHH4-4.8 | 78.95 | 1.53 |
| | | VHH4-4.9 | 149.07 | 2.88 |
| | | VHH4-5 WT | 177.7 | N/A |
| | | VHH4-5.1 | 292.71 | 1.65 |
| | | VHH4-5.2 | 399.94 | 2.25 |
| | | VHH4-5.3 | 382.84 | 2.15 |
| | | VHH4-5.4 | 276.28 | 1.55 |
| | | VHH4-5.5 | 387.58 | 2.18 |
| | | VHH4-5.6 | 193.69 | 1.09 |
| | | VHH4-5.7 | 347.4 | 1.95 |
| | | VHH4-5.8 | 227.89 | 1.28 |
| | | VHH4-5.9 | 310.94 | 1.75 |

FIG. 25A

FOLD-CHANGE IN PROTEIN EXPRESSION LEVEL
ACROSS 8 mAb PROTEINS (each with three variants) IN HEK293 CELLS

FIG. 25B

AA2CDS: PRE-TRAINED AMINO ACID-TO-CODON SEQUENCE MAPPING ENABLING EFFICIENT EXPRESSION AND YIELD OPTIMIZATION

PRIORITY DATA

This application claims the benefit of (priority to) U.S. Provisional Application 63/525,735 filed on Jul. 10, 2023, entitled "AA2CDS", and U.S. Provisional Application 63/616,896 filed on Jan. 1, 2024, entitled "AA2DNA: Amino Acid-to-DNA Sequence Mapping Enabling Efficient Protein Expression and Yield Optimization".

FIELD OF THE TECHNOLOGY

The technology disclosed relates to artificial intelligence type computers and digital data processing systems and corresponding data processing methods and products for emulation of intelligence (i.e., knowledge-based systems, reasoning systems, and knowledge acquisition systems); and including systems for reasoning with uncertainty (e.g., fuzzy logic systems), adaptive systems, machine learning systems, and artificial neural networks.

BACKGROUND

Optimization techniques are at the forefront of scientific advancements in the fields of biotechnology and genetic engineering. These techniques are designed to enhance gene expression and protein production in specific host organisms through precise modifications of DNA sequences. Despite notable advancements in this domain of optimization, especially via deep learning, significant challenges still exist in the heterologous expression of genes from one organism to another. These challenges lead to restricted protein yield, misfolding, and aggregation.

Given their data driven nature, deep learning methods are hindered by the scarcity of large-scale host/protein-specific data, or the high computational cost associated with multi-host/multi-protein data. Furthermore, deep learning methods are hindered by their limitation in covering long context lengths while retaining the relevance of distance tokens, which are of special importance in protein sequences. Finally, deep learning methods, in the best cases, produce a viable mapping of the protein sequence rather than an optimum one.

Gene optimization is a process of particular importance in improving the expression and yield of recombinant proteins within specific host organisms. This optimization process targets specific regions within the plasmid—the extrachromosomal genetic vector that is being used to express the recombinant protein. These specific regions include the promoter, RBS (Ribosome Binding Site), CDSs (DNA Coding Sequences), signal peptides, and transcriptional terminators. Each of these regions plays a pivotal role in regulating gene expression and protein production.

The potency of gene optimization becomes particularly pronounced when considering recombinant protein production for therapeutic applications. Within this specialized arena, addressing the challenges associated with cross-species gene expression is paramount. Such challenges include grappling with issues of inadequate protein yield, misfolding, and aggregation-factors that can significantly impede the efficacy of therapeutic interventions. By optimizing the promoter region, efficient transcription initiation can be ensured. Optimization of the RBS facilitates proper ribosome binding and translation initiation. Additionally, codon optimization of CDSs and signal peptides involves adapting the codons of the heterologous sequence to match the preferred codon usage of the host organism, leading to improved protein expression levels. Furthermore, optimizing the signal peptide can ensure correct targeting and localization of the protein, affecting its stability, functionality, and ultimately its expression in the context of its intended cellular environment. Finally, proper optimization of the terminator region ensures accurate transcription termination, preventing unintended read-through or interference with neighboring genes. By meticulously tailoring the DNA sequence to align with the host organism, researchers can overcome challenges associated with heterologous gene expression thereby enhancing both the quality and quantity of the produced protein.

The significance of yield improvement within this therapeutic framework extends far beyond the laboratory bench. Indeed, the ability to control protein expression for yield quantity and quality improvement purposes has direct implications for the affordability and accessibility of critical/high-impact drugs. Optimized protein production stands as a potential cornerstone for driving down the costs of manufacturing, thereby increasing the accessibility of the biology in question. This facet resonates particularly and profoundly in the therapeutic landscape, where equitable access to effective treatments is of paramount importance.

The existing methods for gene optimization are classified as rule-based and machine learning-based. Rule-based methods hinge on predetermined criteria derived from factors such as codon usage frequency, mRNA secondary structure and stability, GC content, and restriction sites, often sourced from literature studies. However, these methods have significant limitations. Firstly, changes to synonymous codons can adversely impact the protein's structure, including its conformation, folding, stability, and post-translational modification sites. Additionally, relying solely on straightforward criteria like codon usage frequency and mRNA folding energy overlooks key biological factors influencing protein expression, such as sequence context, tRNA availability, ribosome pausing, mRNA degradation, and translation kinetics. Lastly, the optimal codons vary based on the host organism and protein type, making the generalization of rule-based techniques a source of inconsistency.

Despite the transformative impact of machine learning-based techniques, particularly those harnessing the power of deep neural networks and specialized language models due to their ability to understand the underlying features in coding sequences and the relationship between host/protein-specific optimization, their practical success is often hindered by the prevalent issue of data scarcity, an issue that is heightened when the application of interest is yield optimization for therapeutics. For instance, if the modeling focus was the coding sequence (CDS), utilizing a sequence-to-sequence (Seq2Seq) language model to produce a host-specific codon sequence (output) given an amino acid sequence (input) requires large-scale host/protein-specific data. In fact, performing the pre-training of the designated language model from scratch entails the fulfillment of several requirements revolving around data diversity, comprehensiveness, generality, and large scale. Such adaptation of Seq2Seq language models is rather hindered due to the increased sequence length (given each amino acid is encoded by three nucleotides, the sequence length triples). Moreover, the direct adaptation of the Seq2Seq framework does not guarantee the generation of viable codon sequences (i.e., sequences that do map back to the original protein).

The alternative approach of utilizing multi-host/multi-protein data requires scalability of the modeling architecture, resulting in a massive computational prerequisite cost.

Providing these challenges were mitigated via a supervised machine translation or unsupervised conditional generation frameworks, this adaptation only allows the model to produce a "valid" translation rather than an optimized translation given the inadequacy of high-quality amino acid sequence-to-codon sequence mappings (i.e., producing a codon sequence that corresponds to higher expression while retaining/improving its functional attributes). Therefore, the problem of producing a high-quality codon sequence given a low-scale host-specific/protein-specific dataset remains unsolved.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

FIG. 24 includes a table that shows the fold-change in yield/expression for two protein classes, each with several corresponding proteins, that were each expressed in the CHO cell line.

FIG. 25A includes a table that shows the fold-change in yield/expression for the first of two protein classes, each with several corresponding protein indices, that were each expressed in the HEK293 cell line.

FIG. 25B includes a table that shows the fold-change in yield/expression for the second of two protein classes, each with several corresponding proteins, that were each expressed in the HEK293 cell line.

DETAILED DESCRIPTION

Figure 1:
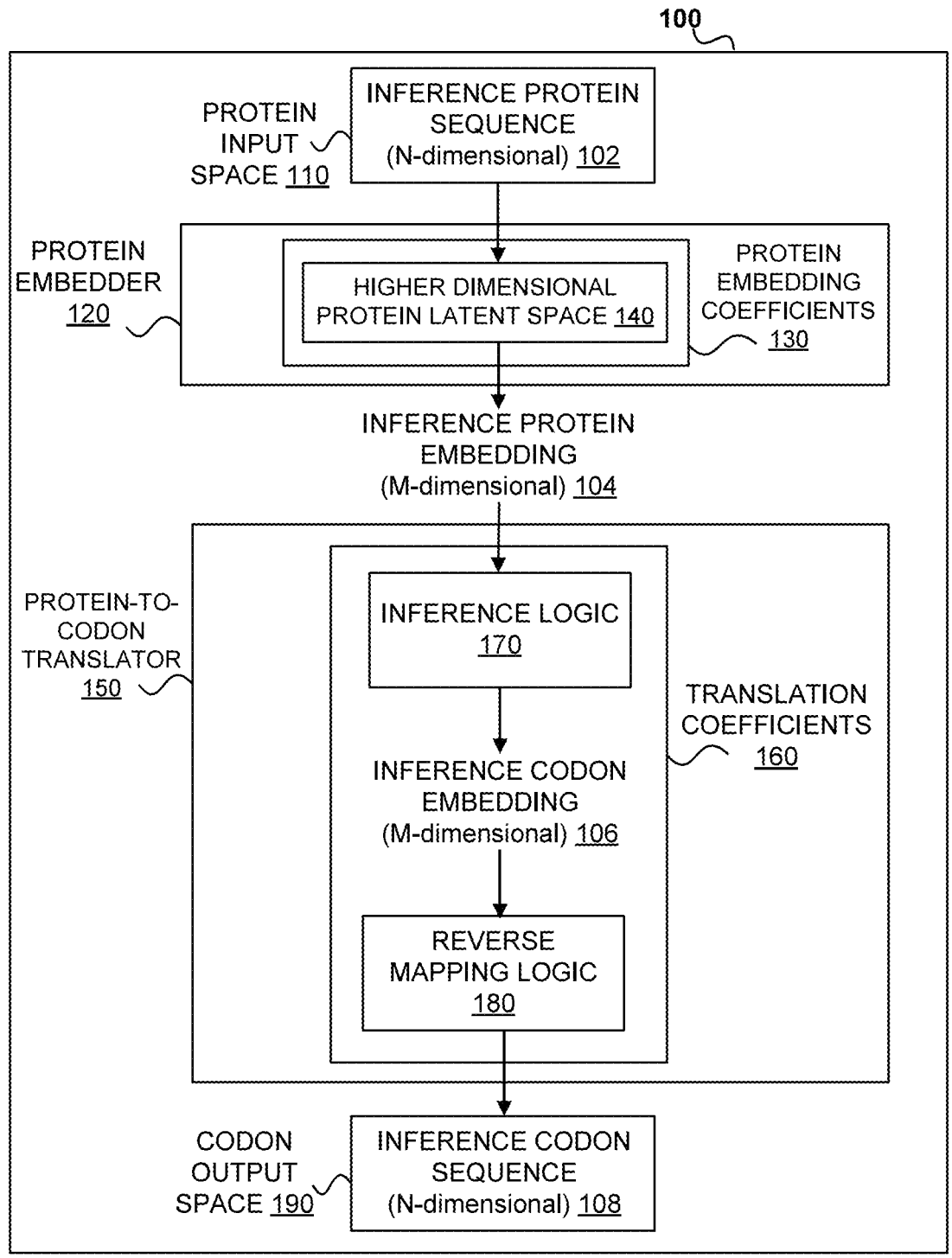
FIG. 1 shows one example protein-to-codon sequence mapping system.

Disclosed is a deep learning-based framework that maps amino acid sequences into optimized codon nucleotide sequences given a low-scale host-specific/protein-specific dataset, referred to as "AA2DNA." The AA2DNA framework provides contextual and dynamic codon mapping. This mapping accounts for the evolutionary features of the protein which in turn opts for more conservative alterations in terms of the resulting structural, functional, and biophysical attributes. The AA2DNA framework utilizes pre-trained amino acid and codon nucleotide embeddings to map the protein into a prominent coding sequence, respectively. By doing so, the AA2DNA framework evades the challenge of high-quality host/protein-specific data sparsity while ensuring an efficient and accessible two modes of operation, supervised and unsupervised. Furthermore, the AA2DNA framework ensures the generation of a valid DNA/gene sequence with robustness to long sequences and their distant token relationships. Finally, the AA2DNA framework enables the generation of optimized codon sequences with improved yield.

The utility of the AA2DNA framework translates to increased protein yield, improved functionality, enhanced gene therapy efficacy, streamlined synthetic biology design, and broadened functional genomics studies, all leading to reduced costs, better performance, and increased accessibility.

AA2DNA is a framework customized for mapping an amino acid sequence into a prominent DNA/gene sequence satisfying pre-determined constraints such as, but not limited to, host organism or protein type. AA2DNA supports application on a subset/full plasmid map, with a bias for CDS optimization for yield improvement. AA2DNA seeks to evade the challenges introduced via the utilization of language models for the codon optimization problem. Firstly, AA2DNA constrains the sampling of codons per amino acid to correspond for valid sequence mapping. Secondly, AA2DNA adopts a novel positional embedding that provides accurate extrapolation for longer sequences while accommodating the impact of sequence folding on the relevance between distant tokens. Thirdly, AA2DNA allows for encompassing the evolutionary relationships between protein classes and hosts by enabling the use of pre-trained embedding vectors extracted from independent source protein and DNA language models to represent the amino acid sequences and codon sequences, respectively.

Such source models are often pre-trained using tens to hundreds of millions of unsupervised sequences and high-complexity architectures encompassing a massive number of trainable parameters and therefore, requiring a massive computational cost. Given the existence of such source/base models in both the protein and DNA/gene domain, pre-training a machine translation network from scratch would not be needed for the default use of the framework. Utilization of embeddings of such source/base models can be viewed to introduce higher-dimensional dense information to the amino acid and codon sequences with dramatically less computational resources, making the task of inferring predictions out of their mappings more approachable. Therefore, and finally, AA2DNA supports the generation of optimum CDS sequences (as opposed to just viable CDS sequences) by enabling the mapping of an arbitrary CDS into another of higher expression and yield.

One example of the AA2DNA is a neural network system. In one implementation, the neural network system processes the input representations as input and generates the output representations as output. In some implementations, the neural network system is at least one of a language model neural network, a sequence-to-sequence neural network, an encoder-decoder neural network, an autoencoder neural network, a variational autoencoder neural network, a generative adversarial neural network, a diffusion neural network, a Transformer neural network, a recurrent neural network, a long-short term memory neural network, an autoregressive neural network, an energy-based neural network, and a flow-based neural network.

Some implementations of the technology disclosed relate to using a Transformer model to provide the AA2DNA framework. In particular, the technology disclosed proposes a parallel input, parallel output (PIPO) the AA2DNA framework based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed AA2DNA framework is a multilayer perceptron (MLP). In another implementation, the disclosed AA2DNA framework is a feedforward neural network. In yet another implementation, the disclosed AA2DNA framework is a fully connected neural network. In a further implementation, the disclosed AA2DNA framework is a fully convolution neural network. In a yet further implementation, the disclosed AA2DNA framework is a semantic segmentation neural network. In yet another further implementation, the disclosed AA2DNA framework is a generative adversarial network (GAN) (e.g., CycleGAN, StyleGAN, pixelRNN, text-2-image, DiscoGAN, IsGAN). In yet another implementation, the disclosed AA2DNA framework includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLaMA versions, BERT, SpanBERT, ROBERTa, XLNet, ELECTRA, UniLM, BART, T5, ERNIE (THU), KnowBERT, DeiT-Ti, DeiT-S, DeiT-B, T2T-ViT-14, T2T-VIT-19, T2T-VIT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCIT-S12/16, CMT-S, CMT-B, VOLO-D1, VOLO-D2, VOLO-D3, VOLO-D4, MoCo v3, ACT, TSP, Max-DeepLab, VisTR, SETR, Hand-Transformer, HOT-Net, METRO, Image Transformer, Taming Transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, VITB/16-FRCNN, VIT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed AA2DNA framework is a convolution neural network (CNN) with a plurality of convolution layers. In another implementation, the disclosed AA2DNA framework is a recurrent neural network (RNN) such as a long short-term memory network (LSTM), bi-directional LSTM (Bi-LSTM), or a gated recurrent unit (GRU). In yet another implementation, the disclosed AA2DNA framework includes both a CNN and an RNN.

In yet other implementations, the disclosed AA2DNA framework can use 1D convolutions, 2D convolutions, 3D convolutions, 4D convolutions, 5D convolutions, dilated or atrous convolutions, transpose convolutions, depth-wise separable convolutions, pointwise convolutions, 1×1 convolutions, group convolutions, flattened convolutions, spatial and cross-channel convolutions, shuffled grouped convolutions, spatial separable convolutions, and deconvolutions.

The disclosed AA2DNA framework can use one or more loss functions such as logistic regression/log loss, multiclass cross-entropy/softmax loss, binary cross-entropy loss, mean-squared error loss, L1 loss, L2 loss, smooth L1 loss, and Huber loss. The disclosed AA2DNA framework can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed AA2DNA framework can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed AA2DNA framework can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed AA2DNA framework can be an ensemble of multiple models, in some implementations.

In some implementations, the disclosed AA2DNA framework can be trained using backpropagation-based gradient update techniques. Example gradient descent techniques that can be used for training the disclosed AA2DNA framework include stochastic gradient descent, batch gradient descent, and mini-batch gradient descent. Some examples of gradient descent optimization algorithms that can be used to train the disclosed AA2DNA framework are Momentum, Nesterov accelerated gradient, Adagrad, Adadelta, RMSprop, Adam, AdaMax, Nadam, and AMSGrad.

In some implementations, AA2DNA can include training a Seq2Seq model from scratch, using pre-trained embeddings for a Seq2Seq model, generating codon sequences under constrained sampling, using scaled rotary positional embeddings, using DPO, generating higher-yield/expression output sequences from lower-yield/expression input sequences, and/or a subset/combination of the aforementioned.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but Transformers can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks. This architecture is described in the following sections.

Encoder-Decoder Architecture

An encoder-decoder architecture is often used for NLP and has two main building blocks. The first building block is the encoder that encodes an input into a fixed-size vector. In the system we describe here, the encoder is based on a recurrent neural network (RNN). At each time step, t, a hidden state of time step, t−1, is combined with the input value at time step t to compute the hidden state at timestep t. The hidden state at the last time step, encoded in a context vector, contains relationships encoded at all previous time steps. For NLP, each step corresponds to a word. Then the context vector contains information about the grammar and the sentence structure. The context vector can be considered a low-dimensional representation of the entire input space. For NLP, the input space is a sentence, and a training set consists of many sentences.

The context vector is then passed to the second building block, the decoder. For translation, the decoder has been trained on a second language. Conditioned on the input context vector, the decoder generates an output sequence. At each time step, t, the decoder is fed the hidden state of time step, t−1, and the output generated at time step, t−1. The first hidden state in the decoder is the context vector, generated by the encoder. The context vector is used by the decoder to perform the translation.

The whole model is optimized end-to-end by using backpropagation, a method of training a neural network in which the initial system output is compared to the desired output and the system is adjusted until the difference is minimized. In backpropagation, the encoder is trained to extract the right information from the input sequence, the decoder is trained to capture the grammar and vocabulary of the output language. This results in a fluent model that uses context and generalizes well. When training an encoder-decoder model, the real output sequence is used to train the model to prevent mistakes from stacking. When testing the model, the previously predicted output value is used to predict the next one.

When performing a translation task using the encoder-decoder architecture, all information about the input sequence is forced into one vector, the context vector. Information connecting the beginning of the sentence with the end is lost, the vanishing gradient problem. Also, different parts of the input sequence are important for different parts of the output sequence, information that cannot be learned using only RNNs in an encoder-decoder architecture.

Attention Mechanism

Attention mechanisms distinguish Transformers from other machine learning models. The attention mechanism provides a solution for the vanishing gradient problem. For example, an attention mechanism can be added onto an RNN encoder-decoder architecture. At every step in this example, the decoder is given an attention score, e, for each encoder hidden state. In other words, the decoder is given weights for each relationship between words in a sentence. The decoder uses the attention score concatenated with the context vector during decoding. The output of the decoder at time step t is based on all encoder hidden states and the attention outputs. The attention output captures the relevant context for time step t from the original sentence. Thus, words at the end of a sentence may now have a strong relationship with words at the beginning of the sentence. In the sentence "The quick brown fox. upon arriving at the doghouse. jumped over the lazy dog." fox and dog can be closely related despite being far apart in this complex sentence.

To weight encoder hidden states, a dot product between the decoder hidden state of the current time step, and all encoder hidden states, is calculated. This results in an attention score for every encoder hidden state. The attention scores are higher for those encoder hidden states that are similar to the decoder hidden state of the current time step. Higher values for the dot product indicate the vectors are pointing more closely in the same direction. The attention scores are converted to fractions that sum to one using the SoftMax function.

The SoftMax scores provide an attention distribution. The x-axis of the distribution is position in a sentence. The y-axis is attention weight. The scores show which encoder hidden states are most closely related. The SoftMax scores specify which encoder hidden states are the most relevant for the decoder hidden state of the current time step.

The elements of the attention distribution are used as weights to calculate a weighted sum over the different encoder hidden states. The outcome of the weighted sum is called the attention output. The attention output is used to predict the output, often in combination (concatenation) with the decoder hidden states. Thus, both information about the inputs, as well as the already generated outputs, can be used to predict the next outputs.

By making it possible to focus on specific parts of the input in every decoder step, the attention mechanism solves the vanishing gradient problem. By using attention, information flows more directly to the decoder. It does not pass through many hidden states. Interpreting the attention step can give insights into the data. Attention can be thought of as a soft alignment. The words in the input sequence with a high attention score align with the current target word. Attention describes long-range dependencies better than RNN alone. This enables analysis of longer, more complex sentences.

The attention mechanism can be generalized as: given a set of vector values and a vector query, attention is a technique to compute a weighted sum of the vector values, dependent on the vector query. The vector values are the encoder hidden states, and the vector query is the decoder hidden state at the current time step.

The weighted sum can be considered a selective summary of the information present in the vector values. The vector query determines on which of the vector values to focus. Thus, a fixed-size representation of the vector values can be created that depends upon the vector query.

The attention scores can be calculated by the dot product, or by weighing the different values (multiplicative attention).

Embeddings

For most machine learning models, the input to the model needs to be numerical. The input to a translation model is a sentence, and words are not numerical. multiple methods exist for the conversion of words into numerical vectors. These numerical vectors are called the embeddings of the words. Embeddings can be used to convert any type of symbolic representation into a numerical one.

Embeddings can be created by using one-hot encoding. The one-hot vector representing the symbols has the same length as the total number of possible different symbols. Each position in the one-hot vector corresponds to a specific symbol. For example, when converting colors to a numerical vector, the length of the one-hot vector would be the total number of different colors present in the dataset. For each input, the location corresponding to the color of that value is one, whereas all the other locations are valued at zero. This works well for working with images. For NLP, this becomes problematic because the number of words in a language is very large. This results in enormous models and the need for a lot of computational power. Furthermore, no specific information is captured with one-hot encoding. From the numerical representation, it is not clear that orange and red are more similar than orange and green. For this reason, other methods exist.

A second way of creating embeddings is by creating feature vectors. Every symbol has its specific vector representation, based on features. With colors, a vector of three elements could be used, where the elements represent the amount of yellow, red, and/or blue needed to create the color. Thus, all colors can be represented by only using a vector of three elements. Also, similar colors have similar representation vectors.

For NLP, embeddings based on context, as opposed to words, are small and can be trained. The reasoning behind this concept is that words with similar meanings occur in similar contexts. Different methods take the context of words into account. Some methods, like GloVe, base their context embedding on co-occurrence statistics from corpora (large texts) such as Wikipedia. Words with similar co-occurrence statistics have similar word embeddings. Other methods use neural networks to train the embeddings. For example, they train their embeddings to predict the word based on the context (Common Bag of Words), and/or to predict the context based on the word (Skip-Gram). Training these contextual embeddings is time intensive. For this reason, pre-trained libraries exist. Other deep learning methods can be used to create embeddings. For example, the latent space of a variational autoencoder (VAE) can be used as the embedding of the input. Another method is to use 1D convolutions to create embeddings. This causes a sparse, high-dimensional input space to be converted to a denser, low-dimensional feature space.

Self-Attention: Queries (Q), Keys (K), Values (V)

Transformer models are based on the principle of self-attention. Self-attention allows each element of the input sequence to look at all other elements in the input sequence and search for clues that can help it to create a more meaningful encoding. It is a way to look at which other sequence elements are relevant for the current element. The Transformer can grab context from both before and after the currently processed element.

When performing self-attention, three vectors need to be created for each element of the encoder input: the query vector (Q), the key vector (K), and the value vector (V). These vectors are created by performing matrix multiplications between the input embedding vectors using three unique weight matrices.

After this, self-attention scores are calculated. When calculating self-attention scores for a given element, the dot products between the query vector of this element and the key vectors of all other input elements are calculated. To make the model mathematically more stable, these self-attention scores are divided by the root of the size of the vectors. This has the effect of reducing the importance of the scalar thus emphasizing the importance of the direction of the vector. Just as before, these scores are normalized with a SoftMax layer. This attention distribution is then used to calculate a weighted sum of the value vectors, resulting in a vector z for every input element. In the attention principle explained above, the vector to calculate attention scores and to perform the weighted sum was the same, in self-attention two different vectors are created and used. As self-attention needs to be calculated for all elements (thus a query for every element), one formula can be created to calculate a Z matrix. The rows of this Z matrix are the z vectors for every sequence input element, giving the matrix a size length sequence dimension QKV.

Multi-headed attention is executed in the Transformer. For example, consider the calculation of self-attention using one attention head. For every attention head, different weight matrices are trained to calculate Q, K, and V. Every attention head outputs a matrix, Z. Different attention heads can capture different types of information. The different Z matrices of the different attention heads are concatenated. This matrix can become large when multiple attention heads are used. To reduce dimensionality, an extra weight matrix W is trained to condense the different attention heads into a matrix with the same size as one Z matrix. This way, the amount of data given to the next step does not increase every time self-attention is performed.

When performing self-attention, information about the order of the different elements within the sequence is lost. To address this problem, positional encodings are added to the embedding vectors. Every position has its unique positional encoding vector. These vectors follow a specific pattern, which the Transformer model can learn to recognize. This way, the model can consider distances between the different elements.

As discussed above, in the core of self-attention are three objects: queries (Q), keys (K), and values (V). Each of these objects has an inner semantic meaning of their purpose. One can think of these as analogous to databases. We have a user-defined query of what the user wants to know. Then we have the relations in the database, i.e., the values which are the weights. More advanced database management systems create some apt representation of its relations to retrieve values more efficiently from the relations. This can be achieved by using indexes, which represent information about what is stored in the database. In the context of attention, indexes can be thought of as keys. So instead of running the query against values directly, the query is first executed on the indexes to retrieve where the relevant values or weights are stored. Lastly, these weights are run against the original values to retrieve data that is most relevant to the initial query.

In another example, several attention heads can be in a Transformer block. In this example, the outputs of queries and keys dot products in different attention heads enable the multi-head attention to focus on different aspects of the input and to aggregate the obtained information by multiplying the input with different attention weights.

Examples of attention calculation include scaled dot-product attention and additive attention. There are several reasons why scaled dot-product attention is used in the Transformers. Firstly, the scaled dot-product attention is relatively fast to compute, since its main parts are matrix operations that can be run on modern hardware accelerators. Secondly, it performs similarly well for smaller dimensions of the K matrix, dk, as the additive attention. For larger dk, the scaled dot-product attention performs a bit worse because dot products can cause the vanishing gradient problem. This is compensated via the scaling factor.

As discussed above, the attention function takes as input three objects: key, value, and query. In the context of Transformers, these objects are matrices of shapes (n, d), where n is the number of elements in the input sequence and d is the hidden representation of each element (also called the hidden vector). Attention is then computed as:

Attention (Q, K, V)=SoftMax where Q, K, V are computed as:

X is the input matrix and WQ, WK, WV are learned weights to project the input matrix into the representations. The dot products appearing in the attention function are exploited for their geometrical interpretation where higher values of their results mean that the inputs are more similar, i.e., pointing in the geometrical space in the same direction. Since the attention function now works with matrices, the dot product becomes matrix multiplication. The SoftMax function is used to normalize the attention weights into the value of 1 prior to being multiplied by the values matrix. The resulting matrix is used either as input into another layer of attention or becomes the output of the Transformer.

Multi-Head Attention

Transformers become even more powerful when multi-head attention is used. Queries, keys, and values are computed the same way as above, though they are now projected into h different representations of smaller dimensions using a set of h learned weights. Each representation is passed into a different scaled dot-product attention block called a head. The head then computes its output using the same procedure as described above.

Formally, the multi-head attention is defined as: MultiHeadAttention (Q, K, V)=[head1, . . . , headh]W0 where headi=Attention ( ).

The outputs of all heads are concatenated together and projected again using the learned weights matrix W0 to match the dimensions expected by the next block of heads or the output of the Transformer. Using multi-head attention, instead of the simpler scaled dot-product attention, enables Transformers to jointly attend to information from different representation subspaces at different positions.

One can use multiple workers to compute the multi-head attention in parallel, as the respective heads compute their outputs independently of one another. Parallel processing is one of the advantages of Transformers over RNNs. Assuming the naive matrix multiplication algorithm has a complexity of:

For matrices of shape (a, b) and (c, d), to obtain values Q, K, V, the following operations should be computed: X·WQ, X·WK, X·WV The matrix X is of shape (n, d) where n is the number of patches and d is the hidden vector dimension. The weights WQ, WK, WV all have a shape of (d, d). Omitting the constant factor 3, the resulting complexity is: n·d2.

Next, the complexity of the attention function itself should be computed, i.e., of SoftMax. The matrices Q and K are both of shape (n, d). The transposition operation does not influence the asymptotic complexity of computing the dot product of matrices of shapes (n, d)·(d, n), therefore its complexity is: n2·d.

Scaling by a constant factor, where dk is the dimension of the keys vector, as well as applying the SoftMax function, both have the complexity of a·b for a matrix of shape (a, b), hence they do not influence the asymptotic complexity. Lastly the dot product SoftMax is between matrices of shapes (n, n) and (n, d) and so its complexity is: n2·d.

The final asymptotic complexity of scaled dot-product attention is obtained by summing the complexities of computing Q, K, V, and of the following attention function:

$$n \cdot d2 + n2 \cdot d.$$

The asymptotic complexity of multi-head attention is the same since the original input matrix X is projected into h matrices of shapes (n,), where h is the number of heads. From the point of view of asymptotic complexity, h is constant, therefore we would arrive at the same estimate of asymptotic complexity using a similar approach as for the scaled dot-product attention.

Transformer models often have the encoder-decoder architecture, although this is not necessarily the case. The encoder is built out of different encoder layers which are all constructed in the same way. The positional encodings are added to the embedding vectors. Afterward, self-attention is performed.

Encoder Block of Transformer

In one example of a single encoder layer of a Transformer network, every self-attention layer can be surrounded by a residual connection, summing up the output and input of the self-attention. This sum is normalized, and the normalized vectors are fed to a feed-forward layer. Every z vector is fed separately to this feed-forward layer. The feed-forward layer is wrapped in a residual connection and the outcome is normalized too. Often, numerous encoder layers are piled to form the encoder. The output of the encoder is a fixed-size vector for every element of the input sequence.

Just like the encoder, the decoder is built from different decoder layers. In the decoder, a modified version of self-attention takes place. The query vector is only compared to the keys of previous output sequence elements. The elements further in the sequence are not known yet, as they still must be predicted. No information about these output elements may be used.

Encoder-Decoder Blocks of Transformer

In another example, a Transformer model having encoder-decoder layers is described. Next to a self-attention layer, a layer of encoder-decoder attention is present in the decoder, in which the decoder can examine the last Z vectors of the encoder, providing fluent information transmission. The ultimate decoder layer is a feed-forward layer. All layers are packed in a residual connection. This allows the decoder to examine all previously predicted outputs and all encoded input vectors to predict the next output. Thus, information from the encoder is provided to the decoder, which could improve the predictive capacity. The output vectors of the last decoder layer need to be processed to form the output of the entire system. This is done by a combination of a feed-forward layer and a SoftMax function. The output corresponding to the highest probability is the predicted output value for a subject time step.

For some tasks other than translation, only an encoder is needed. This is true for both document classification and name entity recognition. In these cases, the encoded input vectors are the input of the feed-forward layer and the SoftMax layer. Transformer models have been extensively applied in different NLP fields, such as translation, document summarization, speech recognition, and named entity recognition. These models have applications in the field of biology as well for predicting protein structure and function and labeling DNA sequences.

Vision Transformer

There are extensive applications of Transformers in vision including popular recognition tasks (e.g., image classification, object detection, action recognition, and segmentation), generative modeling, multi-modal tasks (e.g., visual-question answering, visual reasoning, and visual grounding), video processing (e.g., activity recognition, video forecasting), low-level vision (e.g., image super-resolution, image enhancement, and colorization) and 3D analysis (e.g., point cloud classification and segmentation).

Transformers were originally developed for NLP and worked with sequences of words. In image classification, we often have a single input image in which the pixels are in a sequence. To reduce the computation required, Vision Transformers (ViTs) cut the input image into a set of fixed-sized patches of pixels. The patches are often 16×16 pixels. They are treated much like words in NLP Transformers. Unfortunately, important positional information is lost because image sets are position-invariant. This problem is solved by adding a learned positional encoding into the image patches.

The computations of the ViT architecture can be summarized as follows. The first layer of a ViT extracts a fixed number of patches from an input image. The patches are then projected to linear embeddings. A special class token vector is added to the sequence of embedding vectors to include all representative information of all tokens through the multi-layer encoding procedure. The class vector is unique to each image. Vectors containing positional information are combined with the embeddings and the class token. The sequence of embedding vectors is passed into the Transformer blocks. The class token vector is extracted from the output of the last Transformer block and is passed into a multilayer perceptron (MLP) head whose output is the final classification. The perceptron takes the normalized input and places the output in categories. It classifies the images.

When the input image is split into patches, a fixed patch size is specified before instantiating a ViT. Given the quadratic complexity of attention, patch size has a large effect on the length of training and inference time. A single Transformer block comprises several layers. The first layer implements Layer Normalization, followed by the multi-head attention that is responsible for the performance of ViTs. In a Transformer block, including skip connection data can simplify the output and improve the results. The output of the multi-head attention is followed again by Layer Normalization. And finally, the output layer is an MLP (Multi-Layer Perceptron) with the GELU (Gaussian Error Linear Unit) activation function.

ViTs can be pre-trained and fine-tuned. Pretraining is generally done on a large dataset. Fine-tuning is done on a domain specific dataset.

Domain-specific architectures, like convolutional neural networks (CNNs) or long short-term memory networks (LSTMs), have been derived from the usual architecture of MLPs and suffer from so-called inductive biases that predispose the networks towards a certain output. ViTs stepped in the opposite direction of CNNs and LSTMs and became more general architectures by eliminating inductive biases. A ViT can be seen as a generalization of MLPs because MLPs, after being trained, do not change their weights for different inputs. On the other hand, ViTs compute their attention weights at runtime based on the particular input.

The following detailed description is made with reference to the figures. Example implementations are described to illustrate the technology disclosed, not to limit its scope, which is defined by the claims. Those of ordinary skill in the art will recognize a variety of equivalent variations on the description that follows.

FIGS. 1-20 depict at least one example of a protein-to-codon mapping system that generates an optimized codon sequence upon processing an input sequence. FIGS. 1-10 depict a protein-to-codon mapping system that may include a protein embedder. Moreover, the protein-to-codon mapping system may include a protein-to-codon translator. Depicted implementations also demonstrate at least one example of training a protein-to-codon translator, training a protein embedder, or training a codon embedder. FIGS. 11-20 depict at least one example of a high-yield codon sequence generator. Also shown in the figures is at least one example of a confined search, as well as relative positional embedding to a multi-head transformer. Depicted implementations also demonstrate at least one example of training a high-yield codon sequence generator.

IMPLEMENTATIONS

In this disclosure, the example embodiments may use various machine learning models for the codon sequence optimization and the high-yield codon generation problems described above. As will be described in more detail, the machine learning models may require sample data (also referred to as training data) to make predictions or decisions. In the description that follows, various implementations of the disclosed technology are described with reference to the following figures.

FIG. 1 shows one example of a protein-to-codon sequence mapping system 100. The protein-to-codon sequence mapping system 100 may receive an inference protein sequence 102 for translation to an inference codon sequence 108. The inference protein sequence 102 may be processed via a protein embedder 120 to generate an inference protein embedding 104. The inference protein embedding 104 may be processed via a protein-to-codon translator 150 to generate an inference codon sequence 108. Protein-to-codon sequence mapping system 100 may provide a codon sequence that increases protein yield and improves functionality.

The protein-to-codon sequence mapping system 100 may receive the inference protein sequence 102 from storage in a memory (memory not shown, but see storage subsystem 2002 in computer system 2000). Memory may store the inference protein sequence 102 that requires translation from a protein input space 110 to a codon output space 190. Memory may include, for example, random-access memory (RAM), read-only memory (ROM), static random-access memory (SRAM), dynamic random-access memory (DRAM), flash memory, magnetic disks, optical disks, a computer-readable medium, or others known in the art. The memory may be coupled to at least one processor that is coupled to the memory and operative to perform the exemplary implementations. An example computer system that may be used to implement the protein-to-codon sequence mapping system 100 is described in more detail with reference to FIG. 20.

Inference protein sequence 102 from memory (not shown) may be received by protein input space 110 for subsequent translation via protein-to-codon sequence mapping system 100. Protein input space 110 can be the space of possible input inference protein sequences 102. The inference protein sequence 102 may include any of the 20 amino acid residues, in any sequence order, and without an upper boundary on protein sequence length. Inference protein sequence 102 may be obtained from any source, such as databases or laboratory/clinical sequence data. Inference protein sequence 102 may be pre-processed before or within protein-to-codon sequence mapping system 100, for example via multiple sequence alignment or cluster analysis. Those having skill in the art will appreciate that inference protein sequence 102 may be derived from a previous workflow output and/or prediction model output.

The textual representation of inference protein sequence 102 may be converted from a character representation to a numerical representation of the same protein sequence. A tokenizer may convert each unique element of inference protein sequence 102 into a token or "word" vector having a numerical representation. A tokenizer may utilize a 1:1 strategy that converts each unique amino acid residue into a token or word vector. Other tokenizers may define a unit of inference protein sequence 102 to include two or more amino acids as a k-mer, such that each k-mer may comprise tokens or word vectors. In some embodiments, positional encoding may conserve the positional information of tokens of inference protein sequence 102. Any appropriate method of positional encoding, such as the sinusoidal positional encoding technique, may be applied to achieve the desired function of retaining positional information about inference protein sequence 102.

Protein embedder 120 may receive inference protein sequence 102 from protein input space 110. Protein embedder 120 may be configured to generate inference protein embedding 104. Inference protein sequence 102 may be represented by a sparse vector that is N-dimensional, or low dimensional. In contrast, inference protein embedding 104 may be represented by a dense vector that is M-dimensional, or high dimensional, wherein the M-dimensional value is significantly greater than the N-dimensional value (i.e., $M>>N$) due to extra protein sequence properties encoded within the inference protein embedding 104. Inference protein embedding 104 implicitly represents various features of inference protein sequence 102 that may be relevant to predicting inference codon sequence 108.

Protein language models, such as exemplary protein embedder 120, may extract features directly from inference protein sequence 102. Some examples of extracted features may include, but are not limited to, physical properties of amino acids (such as amino acid charge or hydrophobicity), structural protein features (such as secondary structures formed via alpha helices, beta-sheets, or hairpins, etc., or such as tertiary structures maintained via disulfide bonds or others), structural-functional protein features (such as post-translational modification sites, substrate binding sites, or others), or others. Various features extracted from inference protein sequence 102 may be combined to build inference protein embedding 104 into a meaningful embedded protein representation.

Protein embedder 120 may have any suitable neural network architecture that enables it to process inference protein sequence 102 to generate inference protein embedding 104. Suitable neural networks may include Fully Connected Neural Networks (FCNNs), Recurrent Neural Networks (RNNs), Convolutional Neural Networks (CNNs), Long Short-Term Memory (LSTM) networks, autoencoders, deep belief networks, and generative adversarial networks.

In some implementations, protein embedder 120 may be configured to generate inference protein embedding 104 in response to processing inference protein sequence 102 through protein embedding coefficients 130 trained to encode the inference protein sequence 102 in a higher-dimensional protein latent space 140.

In some implementations of protein-to-codon sequence mapping system 100, protein embedder 120 may be a protein language model, such as Ankh Suite, ProtTrans Suite, or ESM suite. In some examples, protein embedder 120 may be an encoder-decoder transformer, an encoder-only model, or a decoder-only model.

In some implementations, an encoder of a protein language model may learn to project inference protein sequence 102 into a higher-dimensional protein latent space 130 during feature extraction. Higher-dimensional protein latent space 130 may be a contextual representation of inference protein sequence 102. In some implementations, a decoder of a protein language model may learn to generate inference protein embedding sequence 104 from higher-dimensional protein latent space 140.

In some implementations, higher-dimensional protein latent space 140 may be a component of a neural network. Features may be extracted from inference protein sequence 102 in higher-dimensional protein latent space 140. In some implementations, features may be extracted in a pre-trained higher-dimensional protein latent space 380 of pre-trained protein embedder 370 to produce a fixed length embedding representation (e.g. task-specific protein embeddings 364), given an input protein sequence (e.g. a task specific protein sequence 362). As such, higher-dimensional protein latent space 140 may be used for feature extraction and for generating dense representations of inference protein sequence 102.

Protein embedder 120 may comprise protein embedding coefficients 130 that are "weights" of a neural network that can be used as a protein embedder. Protein embedding coefficients 130 may be trained to encode the inference protein sequence 102 in a higher-dimensional protein latent space 140. An example of training a neural network is determining one or more weights associated with the neural network, such as by hardware acceleration via a deep learning accelerator. An example of making an inference is using a trained neural network to compute results by processing input data based on weights associated with the trained neural network. As used herein. the term 'weight' is an example of a 'parameter' as used in various forms of neural network processing. For example, some neural network learning is directed to determining parameters that are then usable for performing neural network inferences using the parameters.

Protein embedder 120 may be a trained neural network. Various training methods may be used to train a neural network, such as supervised training, unsupervised training, semi-supervised training, reinforcement learning, self-learning, transfer learning, and others.

Training a neural network from scratch may be one approach required to train a neural network. In this approach, the neural network begins as naïve and untrained, without any learned parameters. Training a model from scratch may be applicable when a large dataset and/or significant computational resources are available. In other cases, training a model from scratch may be combined with, replaced by, and/or supplemented with transfer learning and/or fine-tuning.

Transfer learning (e.g., feature extraction, attention extraction, fine-tuning, etc.) is reusing the learned weights or parameters from a pretrained model (e.g. a base model) and transferring the existing knowledge (i.e., weights or parameters) to an untrained second model. Transfer learning may include freezing the parameters that were learned during pre-training and utilizing the frozen parameters in connection with the second untrained model. In this way, the second untrained model may build on the knowledge the pre-trained model has previously learned. One example of pre-training the protein embedder 120 for use as a fixed feature extractor when paired with protein-to-codon translator 150, is described in detail with reference to FIG. 2 and FIG. 6. One with skill in the art will recognize the benefits of transfer learning include a large reduction in the computational overhead to extract (protein) features and train the model to integrate (protein) features.

Fine-tuning may be another approach used that transfers knowledge from a pre-trained first model to a second untrained model. However, the parameters of the pre-trained model are not fixed when combining with a second untrained model, and instead the pre-trained model continues to learn when joined with the second untrained model. Fine-tuning may also combine a pre-trained base model with a second untrained model and further training the pre-trained base model parameters with a different dataset domain/distribution (i.e., a fine-tuning dataset that is distinct from the original large dataset used for pre-training, wherein the fine-tuning dataset has a domain/distribution that is related to the original training dataset). One example of pre-training a protein embedder that may be paired with protein-to-codon translator 150, wherein the whole or part of the combined model can be subjected to fine-tuning, is described in detail with reference to FIG. 3. A person having skill in the art will also appreciate that transfer learning via a pre-trained protein embedder provides significantly more information to a second model, rather than merely providing protein sequence data alone.

Inference protein embedding 104, generated by protein embedder 120, may be received by a protein-to-codon translator 150 configured with translation coefficients 160 trained using training protein 650 and codon 660 embedding pairs that are higher-dimensional representations of corresponding training protein 610 and codon 620 pairs. The training protein 650 and codon 660 embedding pairs may be M-dimensional, or higher-dimensional, whereas the training protein 610 and codon 620 pairs may be N-dimensional, or lower-dimensional, such that the M-dimensional value is much greater than the N-dimensional value (M>>N) due to extra protein or codon sequence properties encoded within the protein or codon embeddings, respectively. Protein-to-codon translator 150 configured with translation coefficients 160 may be trained with training protein 650 and codon 660 embedding pairs that are higher-dimensional representations of corresponding training protein 610 and codon 620 pairs, as described in detail with reference to FIG. 6.

The protein-to-codon translator 150 may be a neural network. Examples of neural networks include Fully Connected Neural Networks (FCNNs), Recurrent Neural Networks (RNNs), Convolutional Neural Networks (CNNs), Long Short-Term Memory (LSTM) networks, autoencoders, deep belief networks, and generative adversarial networks.

The translation coefficients 160 are "weights" of a neural network that is used as the protein-to-codon translator 150. An example of training the protein-to-codon translator 150 (i.e., neural network) is determining one or more weights associated with the neural network, such as by hardware acceleration via a deep learning accelerator. An example of making an inference is using a trained the protein-to-codon translator 150 to compute results by processing input inference protein sequence 102 data based on weights associated with the trained protein-to-codon translator 150. As used herein. the term 'weight' is an example of a 'parameter' as used in various forms of neural network processing. For example, some neural network learning is directed to determining parameters that are then usable for performing neural network inferences using the parameters.

Protein-to-codon translator 150 may be a trained neural network. Various training methods may be used to train a neural network such as supervised training, unsupervised training, semi-supervised training, reinforcement learning, self-learning, transfer learning, and others. In one implementation, protein-to-codon translator 150 may be trained with pre-trained amino acid and codon nucleotide embeddings to map the protein into a prominent coding sequence (inference codon sequence 108). One example of training protein-to-codon translator 150 via a supervised machine translation technique is described in detail with reference to FIG. 7. In another implementation, protein-to-codon translator 150 may be trained in an unsupervised machine translation technique with protein embeddings concatenated with their corresponding codon embeddings as input. One example of training protein-to-codon translator 150 via an unsupervised machine translation technique is described in detail with reference to FIG. 9.

Protein-to-codon translator 150 may comprise an inference logic 170. Inference logic 170 may be configured to process the inference protein embedding 104 through the translation coefficients 160 and may cause the protein-to-codon translator 150 to generate an inference codon embedding 106.

As used herein. "inference logic" 170 includes. for example software, hardware, and/or any combination of software and hardware, such as firmware, that can be used to implement inferencing. Inference logic 170 may be configured to generate output predictions for inference protein embedding 104 (e.g., inference protein sequence 102 is never-before seen data that is distinct from training data that includes training protein 610 and codon 620 pairs or training protein 650 and codon 660 embedding pairs). An example of making an inference that may utilize inference logic is using the trained protein-to-codon translator 150 to generate inference codon embedding 106 by processing input inference protein embedding 104 data.

Protein-to-codon translator 150 may also comprise a reverse mapping logic 180. Reverse mapping logic 180 may be configured to process the inference codon embedding 106 through the translation coefficients 160 and may cause the protein-to-codon translator 150 to generate an inference codon sequence 108 that is a translation of the inference protein sequence 102 in the codon output space 190.

As used herein. "reverse mapping logic" 180 includes. for example software, hardware, and/or any combination of software and hardware, such as firmware, that can be used to implement reverse mapping of inference codon embedding 106 to inference codon sequence 108.

Reverse mapping logic 180 may receive inference codon embedding 106 from inference logic 170. Reverse mapping logic 180 may be configured to generate inference codon sequence 108. Inference codon embedding 106 may be represented by a dense vector that is M-dimensional, or high dimensional. In contrast, inference codon sequence 108 may be represented by a sparse vector that is N-dimensional, or low dimensional, wherein the M-dimensional value is significantly greater than the N-dimensional value (i.e., M>>N) due to extra codon sequence properties encoded within the codon embeddings.

Codon output space 190 can be the space of possible output inference codon sequences 108. The generated inference codon sequences 108 will have a codon sequence. For example, the inference codon sequence 108 may be optimized for higher levels of protein expression within the specified host organism, inference codon sequence 108 may be optimized for improved protein function, or inference codon sequence 108 may have other desirable qualities according to training data. One having skill in the art will appreciate the benefits of generating a codon sequence that may retain or improve upon a protein's functional attributes and/or obtain other desirable qualities.

Protein-to-codon sequence mapping system 100 may be implemented using several different framework compositions. For example, one implementation may comprise a framework wherein the protein-to-codon translator 150 is different from the protein embedder 120. An exemplar implementation may comprise a framework wherein the protein-to-codon translator 150 is different from the codon embedder (for example, codon embedder, referred to as DNA language model 410 in FIG. 4).

In other implementations of the framework of protein-to-codon sequence mapping system 100, the protein-to-codon translator 150 is the same as the protein embedder 120, or within the same framework as the protein embedder 120. Exemplary implementations may comprise a framework wherein the protein-to-codon translator 150 is the same as the codon embedder (for example, codon embedder, referred to as DNA language model 410 in FIG. 4), or within the same framework as the codon embedder.

Figure 2:
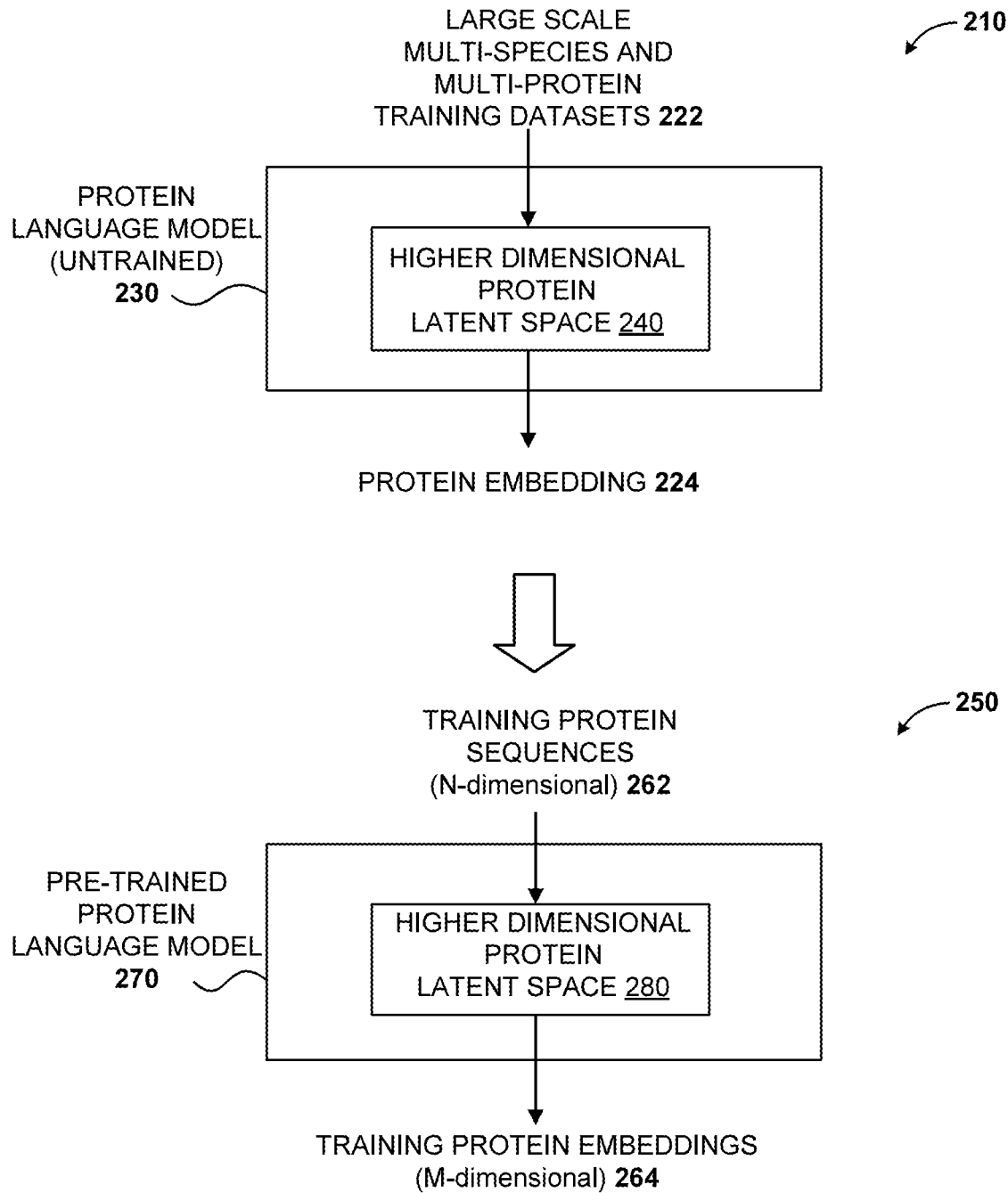
FIG. 2 shows one example of pre-training an untrained protein language model with large scale multi-species and multi-protein training datasets and generating training protein embeddings from a pre-trained protein language model.

FIG. 2 shows one example of pre-training 210 an untrained protein language model 230 with large scale multi-species and multi-protein training datasets 222 and generating 250 training protein embeddings 264 from a pre-trained protein language model 270. Pre-trained protein language model 270 may transfer learning to protein-to-codon sequence mapping system 100. In addition, pre-trained protein language model 270 may supply (pre-trained) training protein embeddings 264 to train protein-to-codon translator 150. Large scale multi-species and multi-protein training datasets 222 may be used to pre-train the untrained protein language model 230. Pre-training from scratch, as depicted in 210, typically requires immense computational resources and data resources.

During pre-training, untrained protein language model 230 may be pre-trained on large-scale multi-species and multi-protein training datasets 222. Untrained protein language model 230 may be pre-trained using tens to hundreds of millions of unsupervised sequences, such as large-scale multi-species and multi-protein training datasets 222, and high-complexity architectures that encompass a massive number of trainable parameters. The sheer size of the large-scale multi-species and multi-protein training datasets 222 and number of trainable parameters required for pre-training may incur a massive computational cost. Pre-trained protein language model 270 may serve as protein embedder 120 in protein-to-codon sequence mapping system 100 (either within or outside of the system framework). Therefore, using pre-trained protein language model 270 can avoid a very large computational cost. One with skill in the art will recognize the savings in time and resources afforded by using pre-trained protein language model 270 in conjunction with other models.

Pre-trained protein language model 270 may generate training protein embeddings 264 that may be used to train protein-to-codon translator 150. In particular, the pre-trained protein language model 270 may receive training protein sequences 262 for processing. After processing, training protein embeddings 264 can be extracted from the higher-dimensional protein latent space 280 of pre-trained protein language model 270. Training protein embeddings 264 may be pre-trained embedding vectors extracted from independent pretrained protein language model 270. Extraction or feature extraction may refer to utilizing the pre-trained higher-dimensional protein latent space 280 of pre-trained protein language model 270 to produce a fixed length embedding representation (e.g., inference protein embeddings 104 or training protein embeddings 264) of input sequences (e.g., inference protein sequence 102 or training protein sequences 262). These extracted training protein embeddings 264 may be used to train protein-to-codon translator 150. Further, these extracted training protein embeddings 264 may belong to paired training protein 650 and codon 660 embeddings. As such, pre-trained protein language model 270 may generate training protein embeddings 264 in the training protein 650 and codon 660 embedding pairs in response to processing corresponding (training) protein sequences 262 in the training protein and codon pairs. Training protein 650 and codon 660 embedding pairs as well as training protein 610 and codon 620 pairs will be discussed in further detail with reference to FIG. 6.

Utilizing pre-trained protein language model 270 in conjunction with protein-to-codon translator 150 can provide massive computational savings as well as a data-rich resource. For example, the computational resources used to pre-train the pre-trained protein language model 270 to generate the higher-dimensional protein latent space 280 are orders of magnitude larger than computational resources used to train the translation coefficients 680 of protein-to-codon translator 670. Further, the training datasets (such as large-scale multi-species and multi-protein training datasets 222) used to pre-train the pre-trained protein language model 270 to generate the higher-dimensional protein latent space 280 are orders of magnitude larger than training datasets used to train the translation coefficients 680 of protein-to-codon translator 670.

Utilization of training protein embeddings 264 from pre-trained protein language model 270 (i.e., source model or base model) can be viewed to provide another model with higher-dimensional dense information that corresponds to training protein sequences 262, with dramatically less computational resources. As a result, the task of generating predictions during inference (as in protein-to-codon sequence mapping system 100) from inference protein embeddings 204 can be much more manageable. Moreover, the use of high-dimensional dense information of inference protein embeddings 104 enables the use of optimum input-target pairs (wherein training protein embeddings 650 may be input and training codon embeddings 660 may be target or ground truth) during supervised training (for example, as in supervised machine translation technique 700), as opposed to the use of valid input-target pairs (wherein sparse training protein sequences 610 may be input and sparse training codon sequences 620 may be target or ground truth). The use of high dimensional dense information in paired training protein 650 and codon 660 embeddings as well as in inference protein embeddings 104 may allow protein-to-codon sequence mapping system 100 to generate "optimized" inference codon sequences 108. as opposed to generating merely "valid" inference codon sequences. Moreover, the use of high dimensional dense information in paired training protein 650 and codon 660 embeddings as well as in inference protein embeddings 104 may allow protein-to-codon sequence mapping system 100 to generate inference codon sequences 108 with a number of possible qualities, in accordance with the training data.

Figure 3:
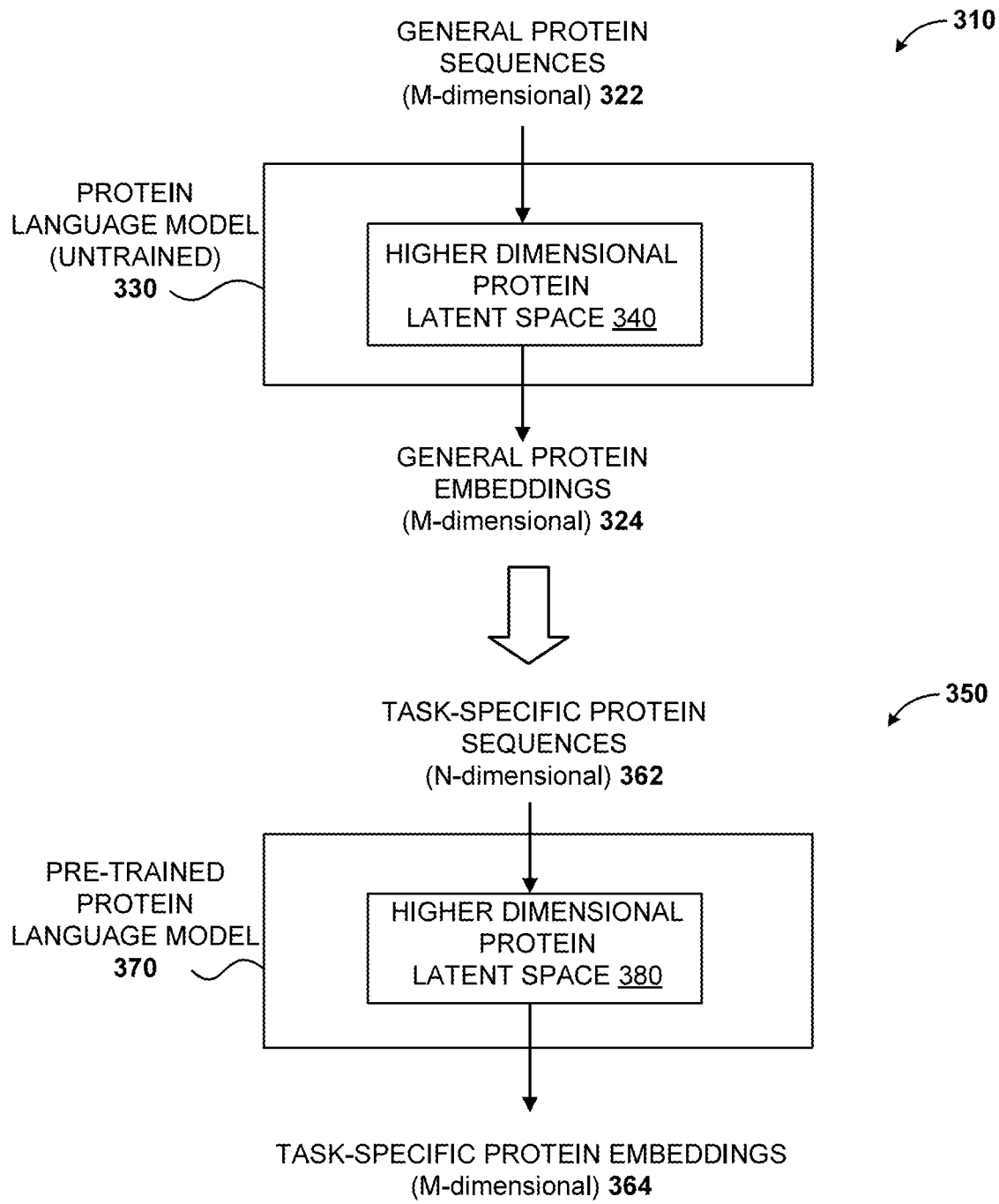
FIG. 3 shows one example of training an untrained protein language model and fine-tuning the pre-trained protein language model.

FIG. 3 shows one example of training 310 an untrained protein language model 330 and fine-tuning 350 the pre-trained protein language model 370. Untrained protein language model 330 may receive general protein sequences 322 during pre-training 310. Pre-trained protein language model 370 may be fine-tuned 350 by performing additional training with task-specific protein sequences 362. Pre-trained protein language model 370 may gain additional task-specific knowledge after fine-tuning 350. One having skill in the art will recognize that fine-tuning a pre-trained base model (such as pre-trained protein language model 370) may be particularly advantageous to save computational resources and/or to train a specific task when only smaller amounts of data may be available.

Untrained protein language model 330 may receive general protein sequences 322 during pre-training 310. During fine-tuning 350, the parameters of pre-trained protein language model 370 are not fixed. Fine-tuning 350 refines the pre-trained protein language model's 370 weights and biases to better perform the specified task of generating task-specific protein embeddings 364 when provided task-specific protein sequences 362 as input for processing. During fine-tuning, pre-trained protein language model 370 may be fine-tuned separately on task specific protein sequences 362, or pre-trained protein language model 370 may be fine-tuned in combination with a second model. For example, pre-trained protein language model 370 may be a protein embedder 120 that may be paired with protein-to-codon translator 150, wherein the whole or part of the combined embedder-translator model can be subjected to fine-tuning. After pre-trained protein language model 370 is fine-tuned, task-specific protein embeddings 364 may be extracted from trained higher-dimensional protein latent space 380.

Figure 4:
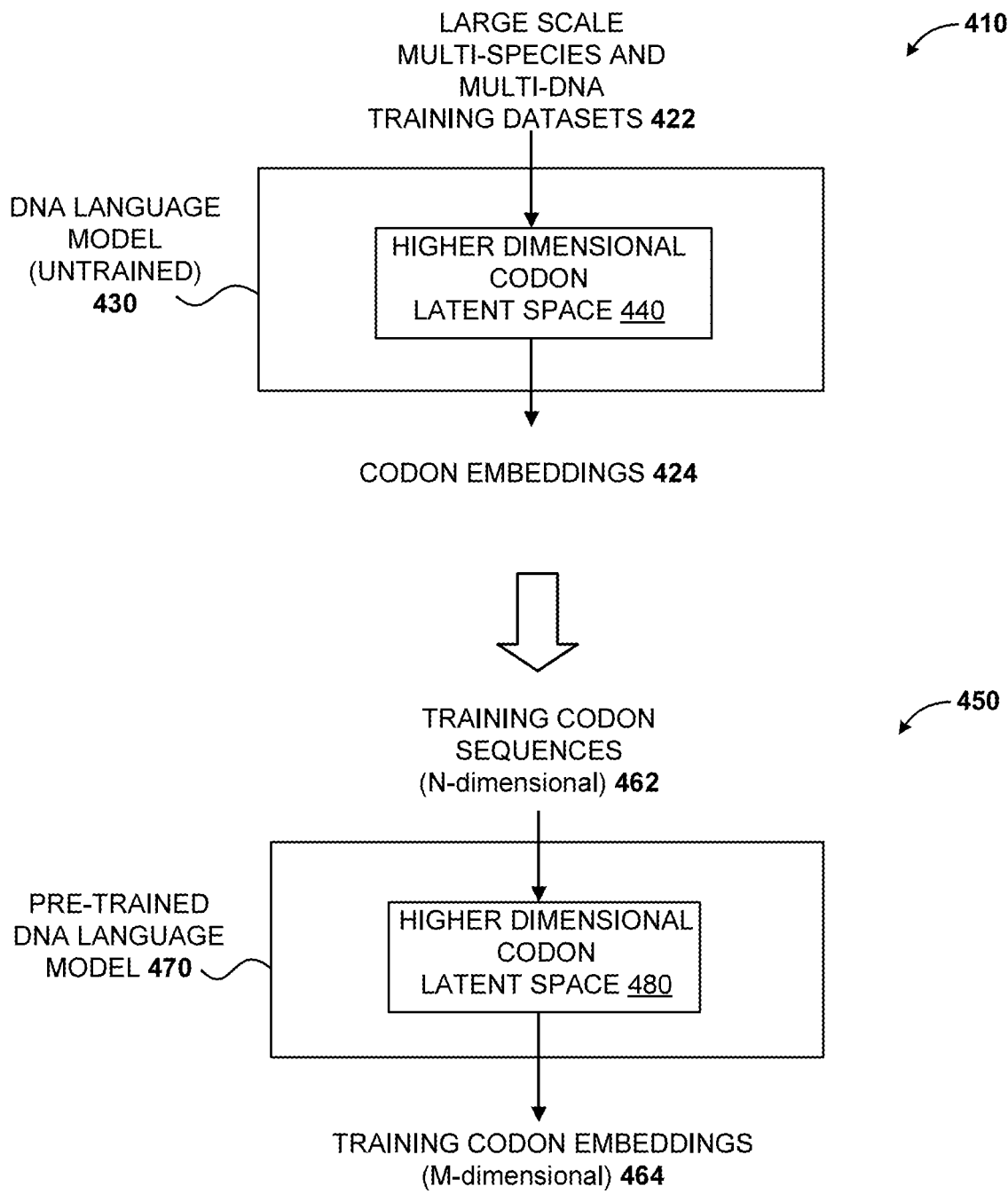
FIG. 4 shows one example of pre-training an untrained DNA language model with large scale multi-species and multi-DNA training datasets and generating training codon embeddings from a pre-trained DNA language model.

FIG. 4 shows one example of pre-training 410 an untrained DNA language model 430 with large scale multi-species and multi-DNA training datasets 422 and generating training codon embeddings 464 from a pre-trained DNA language model 470. In addition, pre-trained DNA language model 470 may supply (pre-trained) training gene embeddings 464 to train protein-to-codon translator 150. Large scale multi-species and multi-DNA training datasets 422 may be used to pre-train the untrained DNA language model 430. Pre-training from scratch, as depicted in 410, typically requires immense computational resources and data resources.

During pre-training, untrained DNA language model 430 may be pre-trained on large-scale multi-species and multi-DNA training datasets 422. Untrained DNA language model 430 may be pre-trained using tens to hundreds of millions of unsupervised sequences, such as large-scale multi-species and multi-DNA training datasets 422, and high-complexity architectures that encompass a massive number of trainable parameters. The sheer size of the large-scale multi-species and multi-DNA training datasets 422 and number of trainable parameters required for pre-training may incur a massive computational cost. Therefore, using pre-trained DNA language model 470 can avoid a very large computational cost. One with skill in the art will recognize the savings in time and resources afforded by using pre-trained DNA language model 470 in conjunction with other models.

Pre-trained DNA language model 470 may generate training codon embeddings 464 that may be used to train protein-to-codon translator 150. In particular, the pre-trained DNA language model 470 may receive training codon sequences 462 for processing. After processing, training codon embeddings 464 can be extracted from the higher-dimensional codon latent space 480 of pre-trained DNA language model 470. Training codon embeddings 464 may be pre-trained embedding vectors extracted from independent pretrained DNA language model 470. Extraction or feature extraction may refer to utilizing the pre-trained higher-dimensional codon latent space 480 of pre-trained DNA language model 470 to produce a fixed length embedding representation (e.g., training codon embeddings 464) of input sequences (e.g., training codon sequences 462). These extracted training codon embeddings 464 may be used to train protein-to-codon translator 150. Further, these extracted training codon embeddings 464 may belong to paired training protein 650 and codon 660 embeddings. As such, pre-trained DNA language model 470 may generate training codon embeddings 464 in the training protein 650 and codon 660 embedding pairs in response to processing corresponding (training) codon sequences 262 in the training protein and codon pairs. Training protein 650 and codon 660 embedding pairs as well as training protein 610 and codon 620 pairs will be discussed in further detail with reference to FIG. 6.

Utilizing pre-trained DNA language model 470 in conjunction with protein-to-codon translator 150 can provide massive computational savings as well as a data-rich resource. For example, the computational resources used to pre-train the pre-trained codon language model 470 to generate the higher-dimensional codon latent space 480 are orders of magnitude larger than computational resources used to train the translation coefficients 680 of protein-to-codon translator 670. Further, the training datasets (such as large-scale multi-species and multi-DNA training datasets 422) used to pre-train the pre-trained DNA language model 470 to generate the higher-dimensional codon latent space 480 are orders of magnitude larger than training datasets used to train the translation coefficients 680 of protein-to-codon translator 670.

Utilization of training codon embeddings 464 from pre-trained DNA language model 470 (i.e., source model or base model) can be viewed to provide another model with higher-dimensional dense information that corresponds to training codon sequences 462, with dramatically less computational resources. Moreover, the use of high-dimensional dense information inherent to training codon embeddings 464 enables the use of optimum input-target pairs (wherein training protein embeddings 650 may be input and training codon embeddings 660 may be target or ground truth) during supervised training (for example, as in supervised machine translation technique 700), as opposed to the use of valid input-target pairs (wherein sparse training protein sequences 610 may be input and sparse training codon sequences 620 may be target or ground truth). The use of high dimensional dense information in paired training protein 650 and codon 660 embeddings may allow protein-to-codon sequence mapping system 100 to generate "optimized" inference codon sequences 108. as opposed to generating merely "valid" inference codon sequences. Moreover, the use of high dimensional dense information in paired training protein 650 and codon 660 embeddings as well as in inference protein embeddings 104 may allow protein-to-codon sequence mapping system 100 to generate inference codon sequences 108 with a number of possible qualities, in accordance with the training data.

Figure 5:
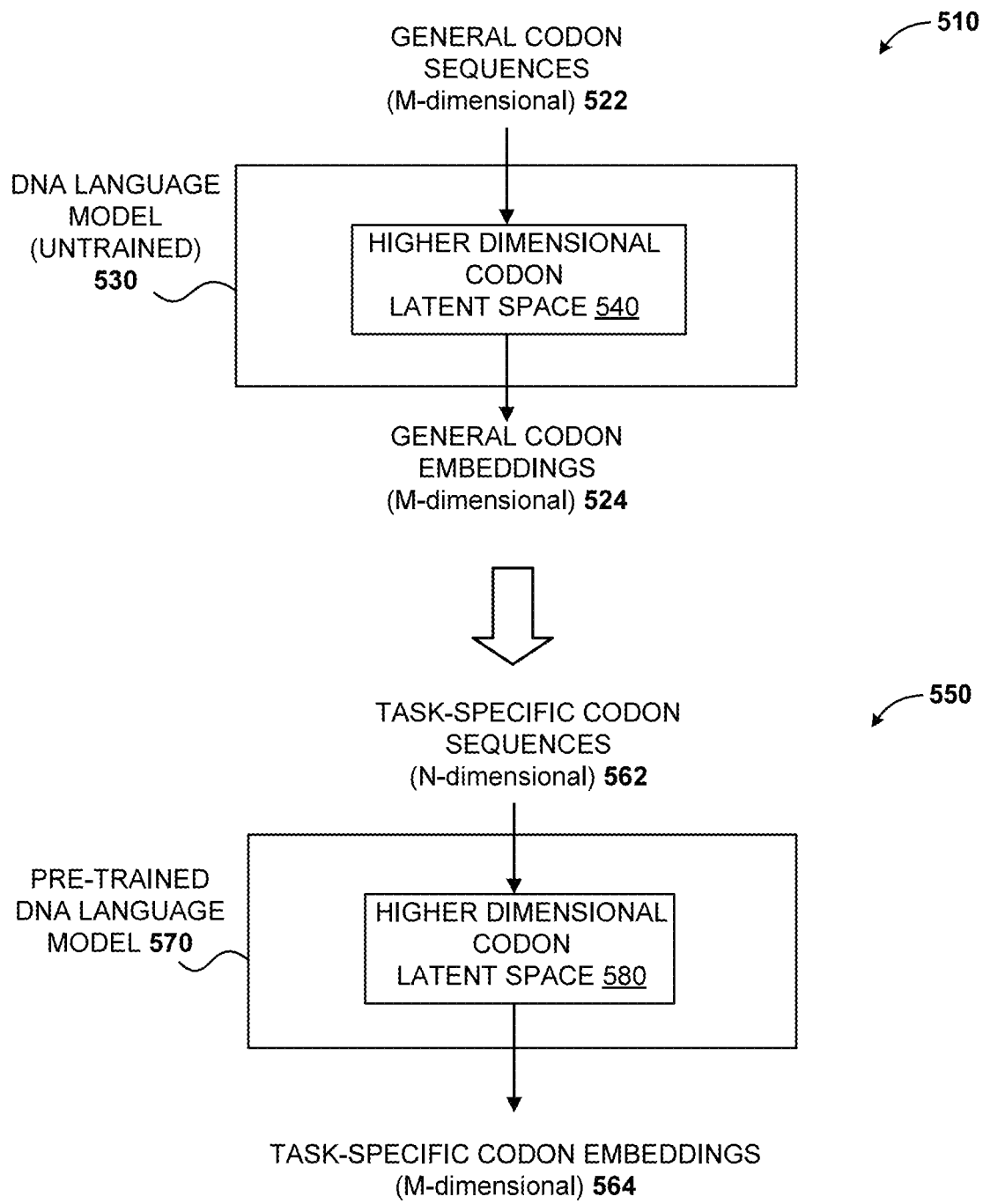
FIG. 5 shows one example of training an untrained DNA language model and fine-tuning the pre-trained DNA language model.

FIG. 5 shows one example of training 510 an untrained DNA language model 530 (i.e., a DNA language model, a codon language model, or a nucleotide language model) and fine-tuning 550 the pre-trained DNA language model 570 (i.e., a DNA language model, a codon language model, or a nucleotide language model). Untrained DNA language model 530 may receive general DNA, nucleotide, or codon sequences 522 during pre-training 510. Pre-trained DNA language model 570 may be fine-tuned 550 by performing additional training with task-specific protein sequences 562. Pre-trained DNA language model 570 may gain additional task-specific knowledge after fine-tuning 550. One having skill in the art will recognize that fine-tuning a pre-trained base model (such as pre-trained DNA language model 570) may be particularly advantageous to save computational resources and/or to train a specific task when only smaller amounts of data may be available.

Untrained DNA language model 530 may receive general gene sequences 522 during pre-training 510. During fine-tuning 550, the parameters of pre-trained DNA language model 570 are not fixed. Fine-tuning 550 refines the pre-trained DNA language model's 570 weights and biases to better perform the specified task of generating task-specific codon embeddings 564 (i.e., codon embeddings or nucleotide embeddings) when provided task-specific codon sequences 562 (i.e., codon sequences or nucleotide sequences) as input for processing. During fine-tuning, pre-trained DNA language model 570 may be fine-tuned separately on task specific gene sequences 562, or pre-trained DNA language model 570 may be fine-tuned in combination with a second model. For example, pre-trained DNA language model 570 may be a pre-trained DNA language model 470 (i.e., a codon embedder) that provides training codon embeddings 660 to train protein-to-codon translator 670. Here, the whole or part of the combined embedder-translator model can be subjected to fine-tuning. After pre-trained codon language model 570 is fine-tuned, task-specific codon embeddings 564 may be extracted from trained higher-dimensional codon latent space 580.

Figure 6:
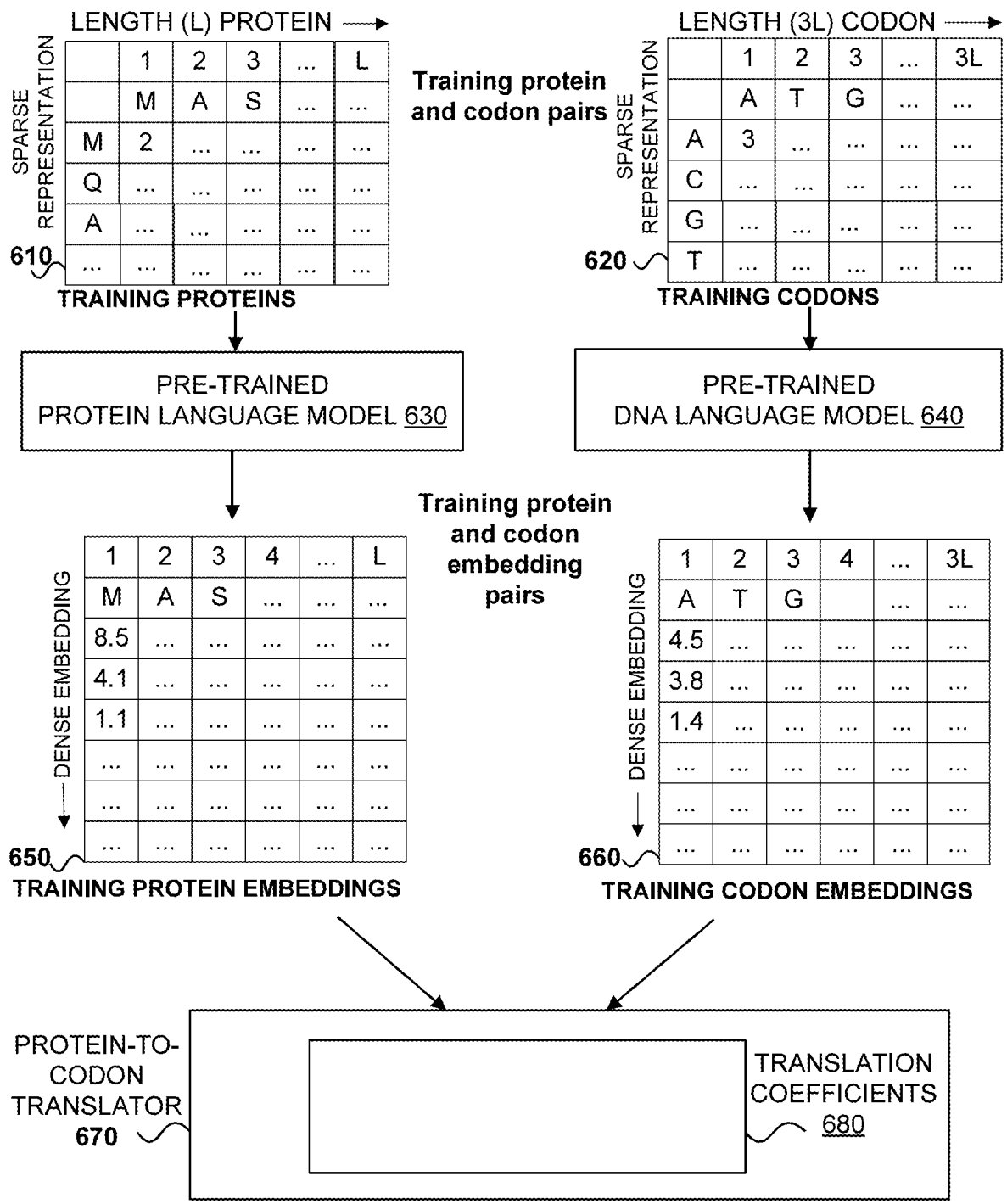
FIG. 6 is one example of training the protein-to-codon translator with training protein and codon embedding pairs.

FIG. 6 is one example of training the protein-to-codon translator 670 with training protein 650 and codon 660 embedding pairs. The training protein 610 and codon 620 (sequence) pairs may be received by pre-trained protein 630 and DNA 640 language models to generate training protein 650 and codon 660 embedding pairs that may be used to train the protein-to-codon translator 670. One having skill in the art will appreciate that utilizing pre-trained protein 630 and DNA 640 language models can significantly reduce the requirement for computational resources.

The training protein 610 and codon 620 pairs may be the initial input. In the "P" pairs of training protein 610 and training codon 620 pairs, a particular training protein 610 sequence may correspond to more than one training codon 620 sequence due to degeneracy of the genetic code (degeneracy refers to the ability of more than one codon to code for a particular amino acid). Training protein 610 and training codon 620 pairs are non-orthogonal, such that a particular training protein 610 may be repeated (redundant) within the "P" pairs of training protein 610 and training codon 620 pairs. Despite non-orthogonality, each training protein 610 must be paired with a corresponding training codon 620 that, when the codon is expressed, would code for the corresponding training protein 610. There can be "P" pairs of the training protein and codon pairs. Additional details regarding the "P" pairs of sequences may be visualized with reference to FIG. 7.

The training protein 610 and codon 620 pairs are sequence data that may be represented as a sparse vector (i.e., or matrix or similar) format. The training protein (sequence) 610 has length L, corresponding to the number of amino acid residues in its sequence. The training protein (sequence) 610 may be tokenized and represented via one-hot encoding. For example, training protein (sequence) 610 may be represented by 2D matrix with dimensions L×a (a signifying the number of amino acids, for example, 20 amino acids). The training protein (sequence) 610 can be represented in a sparse, low dimensional format that is N-dimensional.

The training codon (sequence) 620 has length 3*L, corresponding to the number of nucleotides/codons per amino acid times the length (L) or number of amino acids in the corresponding training protein sequence 610. The training codon (sequence) 620 may be tokenized and represented via one-hot encoding. For example, the training codon (sequence) 620 may be represented by 2D matrix with dimensions 3*L×n (n signifying the number of nucleotides, for example, the 4 nucleotides of DNA). The training codon (sequence) 620 can be represented in a sparse, low dimensional format that is N-dimensional.

The training protein 610 or training codon 620 (sequences) of the "P" training protein and codon pairs, may be received by pre-trained protein language model 630 or pre-trained DNA language model 640, respectively.

After processing, pre-trained protein language model 630 and pre-trained DNA language model 640 each may generate training protein embeddings 650 or training codon embeddings 660, respectively, of the "P" training protein and codon embedding pairs. Training protein 650 and codon 660 embedding pairs may be higher-dimensional representations of corresponding training protein 610 and codon 620 pairs. Feature extraction from higher dimensional latent spaces of the language models may produce dense higher-dimensional representations of protein and codon sequences. Protein embeddings may have sequence length L, with multiple dimensions (or M-dimensions) required to represent the dense protein information. Similarly, codon embeddings may have sequence length 3*L, with multiple dimensions (or M-dimensions) required to represent the dense codon sequence information.

The training protein embeddings 650 or training codon embeddings 660 of the training protein and codon embedding pairs may be used to train protein-to-codon translator 670. Training the downstream architecture may include a supervised machine translation approach or an unsupervised conditional generation approach. In a supervised machine translation approach, the training protein embeddings 650 can be passed as input while their corresponding training codon embeddings 660 (of the P training protein and codon embedding pairs) can be passed as target (or ground truth), as will be further described with reference to FIG. 7. In an unsupervised conditional generation approach, training protein embeddings 650 may be concatenated to their corresponding training codon embeddings 660 (of the P training protein and codon embedding pairs) and passed together as input to the unsupervised architecture, as will be further described with reference to FIG. 9.

A large reduction in the required computational resources may be observed by training the protein-to-codon translator 670 with training protein 650 and codon 660 embedding pairs. For example, the computational resources used to train the translation coefficients 680 on the training protein 650 and codon 660 embedding pairs may be orders of magnitude smaller than computational resources used to train the translation coefficients 680 on the training protein 610 and codon 620 pairs of sequences.

A large reduction in the required dataset resources may be observed by training the protein-to-codon translator 670 with training protein 650 and codon 660 embedding pairs. For example, the training datasets used to train the translation coefficients 680 on the training protein 650 and codon 660 embedding pairs are orders of magnitude smaller than training datasets used to train the translation coefficients 680 on the training protein 610 and codon 620 pairs of sequences.

The protein-to-codon translator 670, for example in protein-to-codon sequence mapping system 100, may be customized for mapping a protein sequence (such as inference protein sequence 102) into a codon sequence (such as inference codon sequence 108) that satisfies one or more pre-determined constraints such as, but not limited to, host organism or protein type.

The protein-to-codon translator 670 may be, for example, a Seq2Seq model, a machine translation model, a large language model, and/or other similarly suited models.

For example, a host organism constraint may be implemented if the training protein 610 and codon 620 pairs belong to the same host organism, and therefore make the protein-to-codon translator 670 (or 150) host organism-specific. Moreover, a host organism-specific protein-to-codon translator (such as translator 150) may generate an inference codon sequence 108 that may also satisfy a host-organism-type constraint.

In other implementations, protein-to-codon sequence mapping system 100 may utilize more than one host-organism specific translator. For example, protein-to-codon sequence mapping system 100 may be configured to provide respective protein-to-codon translators that are specific to respective host organisms. In turn, the respective protein-to-codon translators may be separately trained on respective training protein and codon pairs that belong to the respective host organisms.

In another implementation, protein-to-codon sequence mapping system 100 may be further configured to include a host organism filtering logic that predicts host organism-types for inference codon sequences. The host organism filtering logic may also prune (a) the inference codon sequences whose host organism-type prediction confidence is below a threshold or (b) the inference codon sequences that are predicted to belong to a host organism-type different than a target host organism-type.

In another example, a protein-type constraint may be implemented if the training protein 610 and codon 620 pairs belong to the same protein type, and therefore make the protein-to-codon translator 670 (or 150) host protein-specific. Moreover, a host organism-specific protein-to-codon translator (such as translator 150) may generate an inference codon sequence 108 that may also satisfy a protein-type constraint.

In other implementations, protein-to-codon sequence mapping system 100 may utilize more than one protein-specific translator (for example, several translators, each translator being specific to one protein type, may be used). For example, protein-to-codon sequence mapping system 100 may be configured to provide respective protein-to-codon translators that are specific to respective proteins (or protein types). In turn, the respective protein-to-codon translators may be separately trained on respective training protein and codon pairs that belong to the respective proteins (or protein types).

In another implementation, protein-to-codon sequence mapping system 100 may be further configured to include a protein filtering logic that predicts host protein-types for inference codon sequences. The protein filtering logic may also prune the inference codon sequences that are predicted to belong to a protein-type different than a target protein-type.

Figure 7:
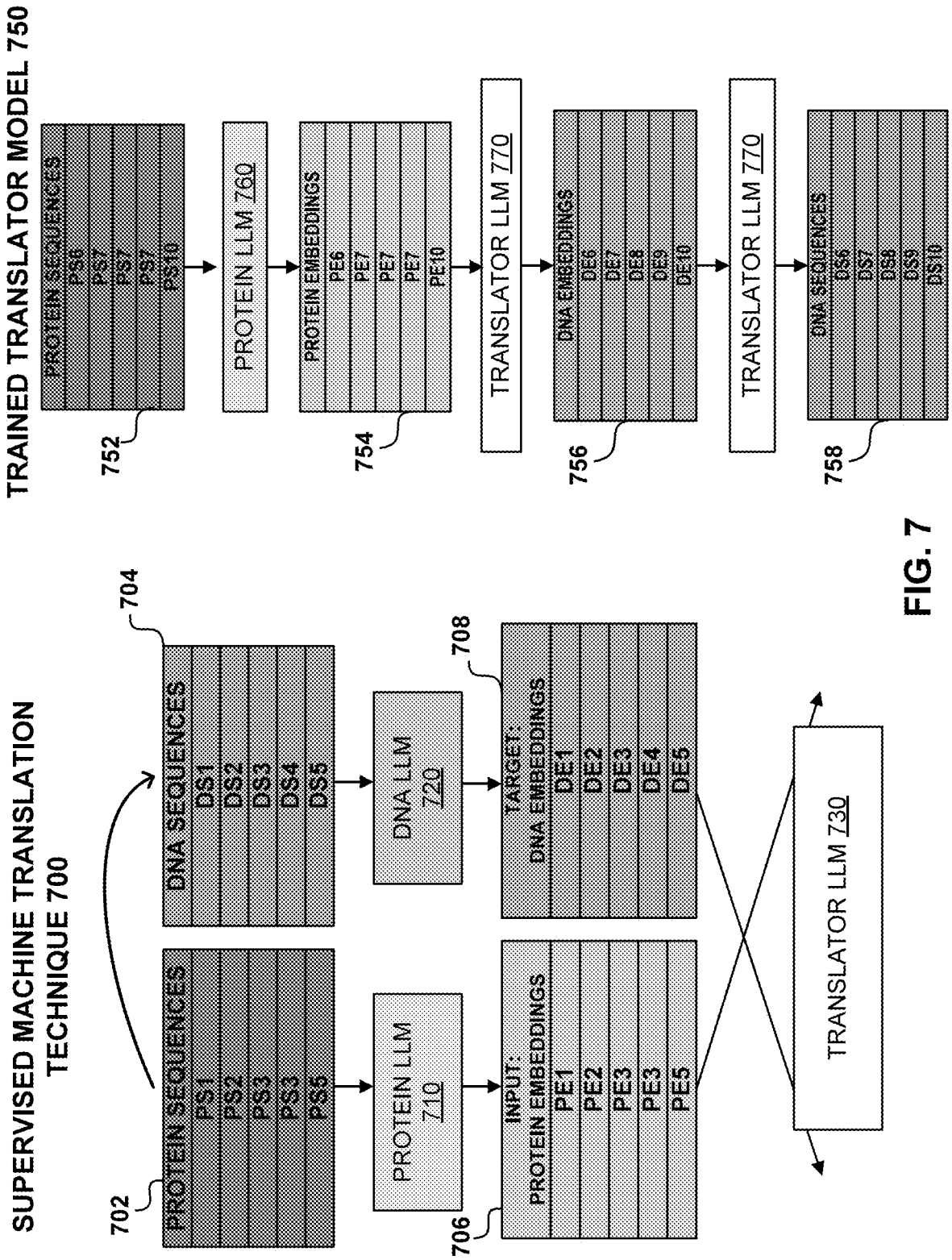
FIG. 7 shows the supervised machine translation technique to train the protein-to-codon translator and shows generating the codon sequence output via the trained translator.

FIG. 7 shows one example of supervised machine translation technique 700 training translator LLM 730 (protein-to-codon translator). FIG. 7 also shows an example of generating DNA Sequences 758 (inference codon sequences) via the trained translator model 750. In supervised machine translation technique 700, training protein 702 and DNA 704 sequence pairs may be provided to protein LLM 710 (i.e., protein LLM can be a pre-trained protein language model) and DNA LLM 720 (i.e., DNA LLM can be pre-trained DNA language model). Output training protein 706 and codon 708 embeddings may be utilized to train translator LLM 730 (protein-to-codon translator). Trained translator model 750 may receive (inference) protein sequences 752 for processing and generate DNA sequences 758 (inference codon sequences) as output. For example, DNA sequences 758 (inference codon sequences) may be optimized for yield/expression of the corresponding protein or may obtain other possible desirable qualities, in accordance with the training data.

In supervised machine translation technique 700. "P" pairs of training protein 702 and DNA 704 sequence pairs can be provided to protein LLM 710 and DNA LLM 720, respectively. In this implementation, for example, there are five pairs of corresponding protein-DNA sequences. Of note, the corresponding protein-DNA sequences are not required to be orthogonal, that is, a particular protein sequence (PS3)

may correspond to more than one DNA sequence (DS3 and DS4) due to degeneracy of the genetic code. Protein LLM 710 and DNA LLM 720 may produce "P" pairs of training protein 706 and DNA 708 embedding pairs. In this implementation, five pairs of corresponding protein-DNA embeddings may be generated in a pairwise manner by protein LLM 710 and DNA LLM 720.

In supervised machine translation technique 700. "P" pairs of training protein 706 and DNA 708 can provide embedding pairs to translator LLM 730 during training. In particular, the training protein embeddings 706 may be provided as input, whereas the corresponding training DNA embeddings 708 may be provided as target, in a pairwise manner. For example, when training protein embedding PE1 is provided as input, then training DNA embedding DE1 may be provided as target.

Translator LLM 730 (i.e., protein-to-codon translator 670) may have translation coefficients 680 that represent the various "weights" of the model. Translation coefficients 680 may be trained using a supervised machine translation technique 700. For example, supervised machine translation technique 700 may train translation coefficients 680 to process the training protein embeddings 706 as inputs and generate the training codon embeddings 708 as target outputs.

Trained translator model 750 may receive protein sequences 752 as input. Input protein sequences 752 were never used during training of the trained translator LLM 750. Protein LLM 760 receives protein sequences 752 for processing and may generate protein embeddings 754 in response. Protein embeddings 754 are provided to translator LLM 770 to generate DNA embeddings 756, which can be reverse mapped via translator LLM 770 to the output DNA sequences 758. For example, upon expression within the desired expression system, DNA sequences 758 yield valid proteins. In other implementations, DNA sequences 758 may obtain other desirable qualities, in accordance with the training data.

Figure 8:
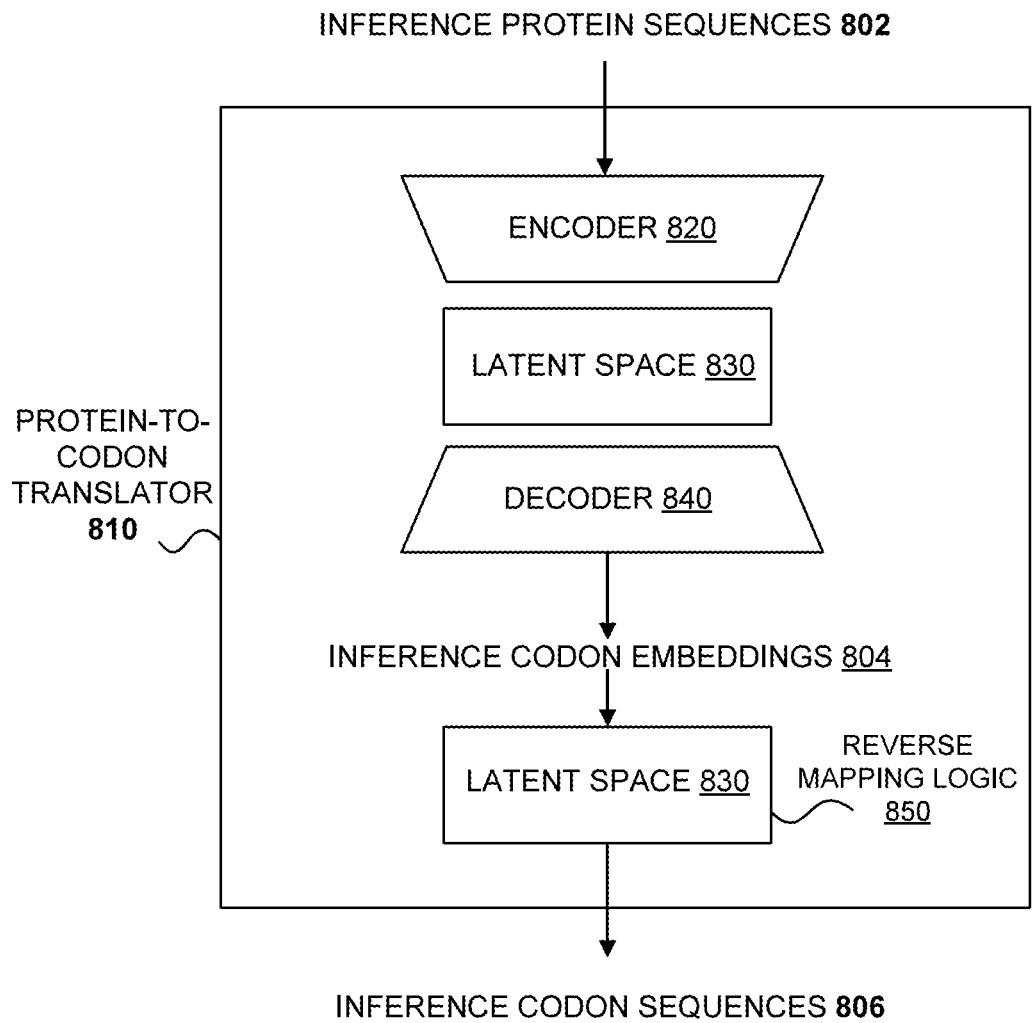
FIG. 8 is one implementation of the protein to codon translator as a sequence to sequence (seq2seq) neural network.

FIG. 8 is one implementation of the protein-to-codon translator 810 as a sequence to sequence (Seq2Seq) neural network model. At inference, (trained) protein-to-codon translator 810 may receive inference protein sequences 802 for processing and generate inference codon sequences 806 as output. One having skill in the art will appreciate that a Seq2Seq model may be particularly well-suited for text-like data of protein and/or codon sequences.

Inference protein sequences 802 may be provided to the protein-to-codon translator 810 that is a Seq2Seq model. In some implementations, the Seq2Seq model may be pre-trained. In other implementations, the Seq2Seq model may be trained from scratch. One having skill in the art will understand the various types of training that may be applied to each and/or all layers of the Seq2Seq model, either separately or in a combined manner.

The Seq2Seq model may be implemented with various architectures. For example, the Seq2Seq model may comprise an encoder network, a latent space, and a decoder network. FIG. 8 shows an example wherein inference protein sequences 802 may be received and processed by an encoder 820 (network), latent space 830, and decoder 840 (network), to generate inference codon embeddings 804. Inference codon embeddings 804 may be provided to latent space 830 that is configured to provide a reverse mapping logic 850 that generates output inference codon sequences 806.

The Seq2Seq model may be a new architecture or a pre-trained architecture. In an approach with new architecture, any new networks may include the use of layers. For example, without being limiting, layers may include bi-directional long short-term memory networks (bi-LSTMs), attention layers, convoluted attention layers, or transformer layers. One with skill in the art will recognize that a Seq2Seq model may provide efficient modeling of long-term dependencies via specific layers or specific pre-trained architectures.

The Seq2Seq model may be a pre-trained architecture. In some implementations, the Seq2Seq encoder network may be a pre-trained encoder-only language model. In other implementations, the Seq2Seq decoder network can be a pre-trained decoder-only language model. In alternative implementations, the Seq2Seq encoder and decoder networks may be combined in a pre-trained encoder-decoder language model. One with skill in the art will recognize that a Seq2Seq model may provide efficient modeling of long-term dependencies via specific pre-trained architectures.

Figure 9:
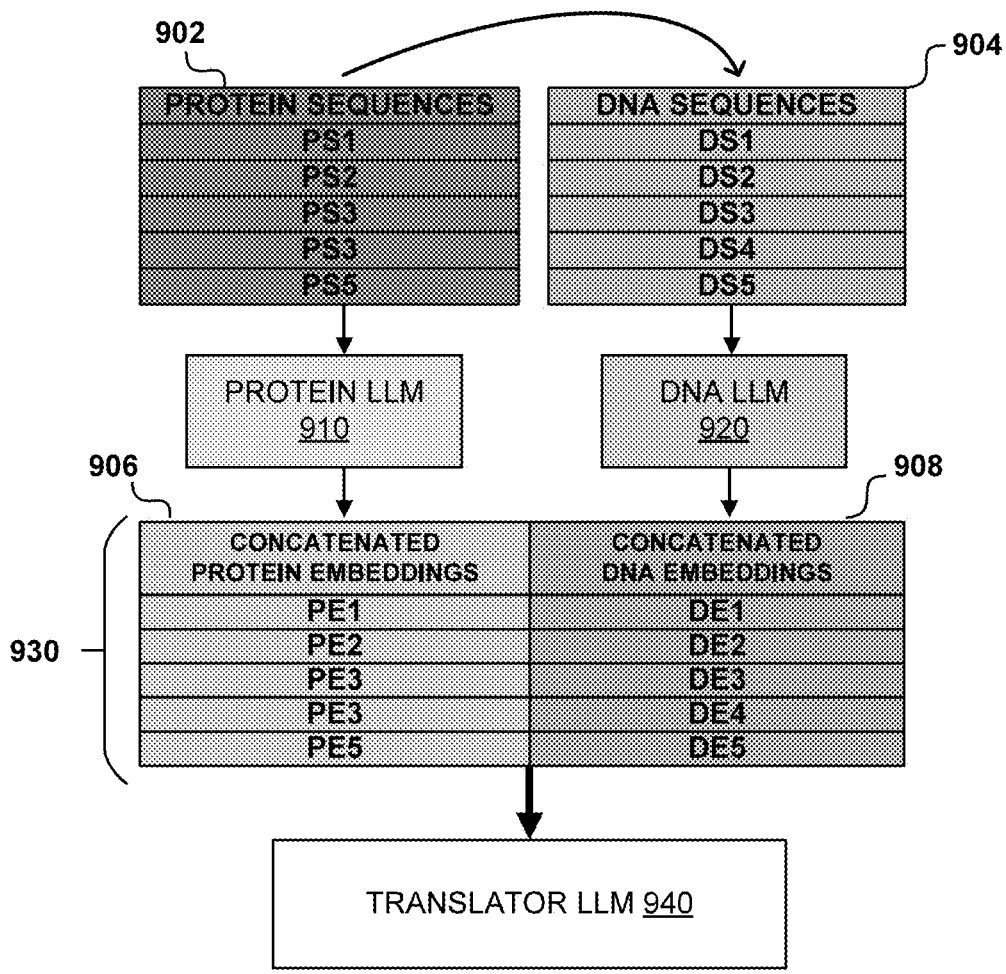
FIG. 9 shows one example of the unsupervised conditional generation technique to train the protein-to-codon translator.

FIG. 9 shows one example of unsupervised conditional generation technique 900 training translator LLM 940 (protein-to-codon translator). In unsupervised conditional generation technique 900, training protein 902 and DNA 904 sequence pairs can be provided to protein LLM 910 (i.e., protein LLM can be a pre-trained protein language model) and DNA LLM 920 (i.e., DNA LLM can be a pre-trained DNA language model). Output training protein 906 and codon 908 embeddings may be utilized to train translator LLM 930 (protein-to-codon translator). One having skill in the art will understand that any suitable unsupervised machine learning technique may used in place of an unsupervised conditional generation technique. This example is meant to provide one of many possible implementations, and this example is by no means meant to limit the scope of possible unsupervised machine learning techniques that may be applied.

In unsupervised conditional generation technique 900. "P" pairs of training protein 902 and DNA 904 sequence pairs can be provided to protein LLM 910 and DNA LLM 920, respectively. In this implementation, for example, there are five pairs of corresponding protein-DNA sequences. Of note, the corresponding protein-DNA sequences are not required to be orthogonal, that is, a particular protein sequence (PS3) may correspond to more than one DNA sequence (DS3 and DS4) due to degeneracy of the genetic code. Protein LLM 910 and DNA LLM 920 may produce "P" pairs of training protein 906 and DNA 908 embedding pairs. In this implementation, five pairs of corresponding protein-DNA embeddings may be generated in a pairwise manner by protein LLM 910 and DNA LLM 920. In a next step, training protein 906 and DNA 908 embedding pairs may be concatenated in a pairwise manner to generate concatenated training protein and DNA embeddings 930 (i.e., training protein embedding PE1 may be concatenated with training DNA embedding DE1).

In unsupervised conditional generation technique 900. "P" pairs of concatenated training protein and DNA embeddings 930 may be provided to translator LLM 940 during unsupervised training.

In unsupervised conditional generation technique 900, translator LLM 940 may have a set of translation coefficients that are the "weights" or "parameters" of the network, such that the weights of the network may be updated as translator LLM 940 learns. Translation coefficients may be trained using an unsupervised conditional generation technique 900. In addition, unsupervised conditional generation technique 900 can train the translation coefficients to process concatenations 930 of the training protein embeddings 906 and the training codon embeddings 908 as inputs and generate the (un-concatenated) training codon embeddings 908 as target outputs.

Translator LLM 940 may be implemented with various architectures. For example, Translator LLM 940 (e.g., protein-to-codon translator) can be a variational autoencoder (VAE). In other implementations, Translator LLM 940 (e.g., protein-to-codon translator) can be a generative adversarial network (GAN). Still in other implementations, translator LLM 940 (e.g., protein-to-codon translator) can be a diffusion model.

Figure 10:
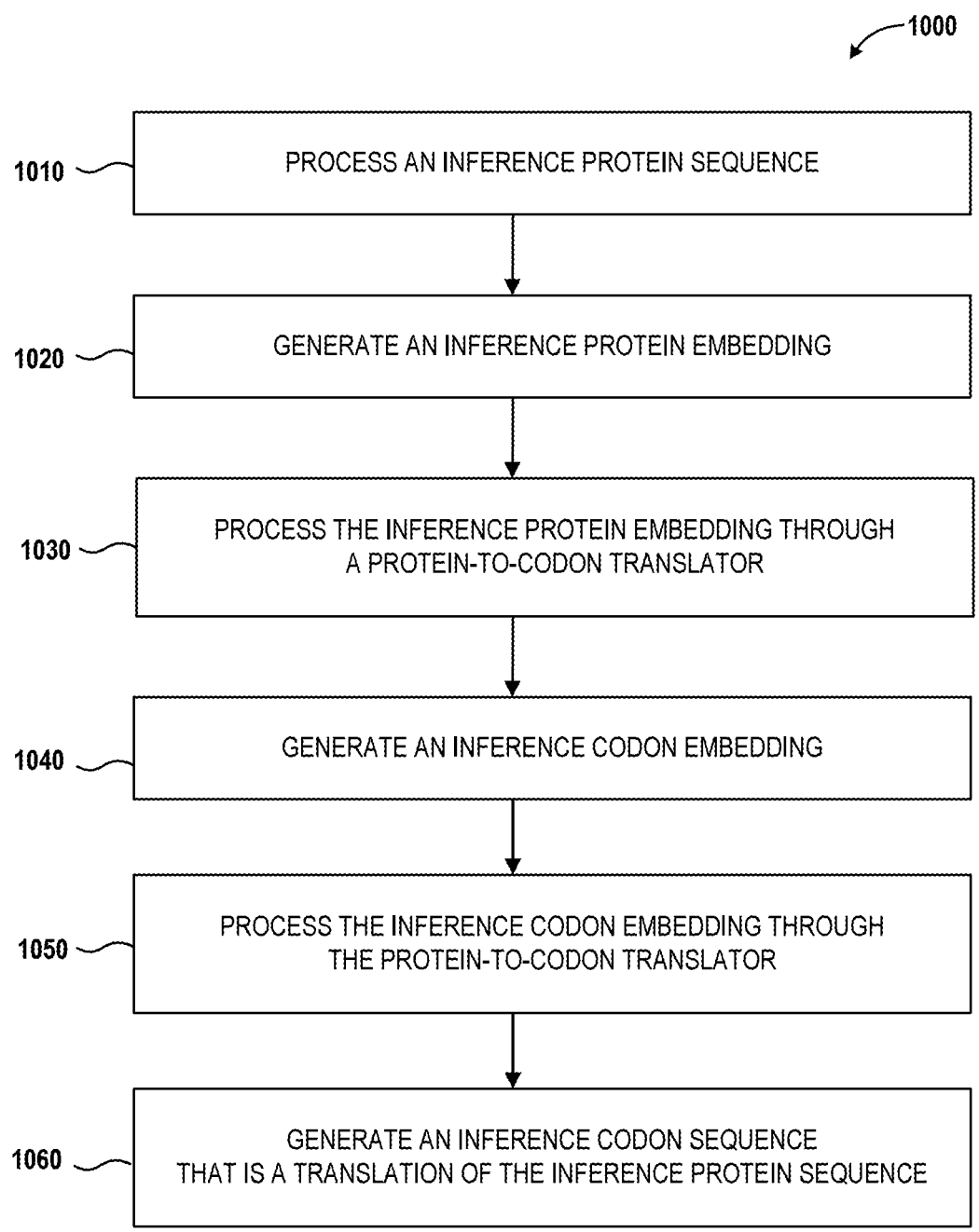
FIG. 10 is a flowchart of one example of generating a codon sequence for a protein-to-codon sequence mapping system.

FIG. 10 is a flowchart of one example of generating a codon sequence 1000 for a protein-to-codon sequence mapping system 100. As depicted, the generating a codon sequence method 1000 includes processing an inference protein sequence 1010, generating an inference protein embedding 1020, processing the inference protein embedding through a protein-to-codon translator 1030, generating an inference codon embedding 1040, processing the inference codon embedding through the protein-to-codon translator 1050, and generating an inference codon sequence that is a translation of the inference protein sequence 1060. The generating a codon sequence method 1000 enables generating a codon sequence that correlates to a valid protein. In some implementations, the generating a codon sequence method 1000 may generate a codon sequence with desired qualities (for example, a codon sequence that expresses a protein with an improved functionality), in accordance with the training data.

Processing an inference protein sequence 1010 may include receiving an input protein sequence. Inference protein sequence 1010 may be tokenized, subjected to one-hot-encoding, or other approaches to transform the sequence of characters (or text) into a sequence of corresponding numerical representations. The numerical representation of inference protein sequence is low-dimensional (N-dimensional), wherein little information (i.e., amino acid sequence) may be represented. The inference protein sequence may be received and processed by a protein embedder. A protein embedder that receives an inference sequence for processing may be pre-trained using training protein sequences (e.g., general protein sequences, UniProt protein sequences, or others.). In some implementations, the protein embedder may be fine-tuned, either separately from protein-to-codon sequence mapping system 100 and/or as a part of protein-to-codon sequence mapping system 100.

Generating an inference protein embedding 1020 includes a protein embedder generating a protein embedding. The inference protein embedding may be a higher-dimensional representation of the corresponding inference protein sequence, having M-dimensions that may denote biochemical, biophysical, structural, and/or other information about the inference protein sequence. Inference protein embedding may be a dense, high-dimensional representation, wherein the M-dimensional value of the inference protein embedding is significantly greater than the N-dimensional value of the inference protein sequence that corresponds to a sparse, low-dimensional representation.

Processing the inference protein embedding through a protein-to-codon translator 1030 may include providing the inference protein embedding to the protein-to-codon translator. The protein-to-codon translator may be trained using training protein and codon embedding pairs, for example, using a supervised machine translation technique. Training the protein-to-codon translator with protein and codon embedding pairs can significantly reduce the computational resources required for training, while also providing the protein-to-codon translator with much more abundant source of information during training. Protein-to-codon translator may have translation coefficients that represent the weights of the model. Moreover, the learned translation coefficients may correspond to a pre-trained protein-to-codon translator, and as such, a pre-trained protein-to-codon translator may be provided to the protein-to-codon sequence mapping system 100, in some implementations.

Generating an inference codon embedding 1040 may include an inference codon embedding that has been processed by the translation coefficients of the protein-to-codon translator. Inference codon embedding is a predicted inference codon embedding that may be a dense, higher-dimensional representation that is M-dimensional.

Processing the inference codon embedding through the protein-to-codon translator 1050 may include translation coefficients that process inference codon embedding. The high-dimensional inference codon embedding (having an M-dimensional value) may be transformed to a corresponding lower-dimensional codon sequence (having an N-dimensional value).

Generating an inference codon sequence that is a translation of the inference protein sequence 1060 may include the protein-to-codon translator generating an inference codon sequence. The inference codon sequence may be a lower dimensional (N-dimensional) numerical representation of the codon sequence, wherein the M-dimensional value of the inference codon embedding is significantly greater than the N-dimensional value of the inference codon sequence.

Autoregressive Decoding

In an alternative implementation of autoregressive decoding, the following flow is executed:
1. Process an inference protein sequence.
2. Generate an inference protein embedding.
4. Generate an inference codon embedding for the start token only.
5. Process the inference protein and codon embeddings through the protein-to-codon translator.
6. Generate an inference codon sequence with the codon for the first inference amino acid.
7. In a loop:
   a. Generate an inference codon embedding for the start token and any generated tokens thus far.
   b. Process the inference protein and codon embeddings through the protein-to-codon translator.
   c. Generate an inference codon sequence with the additional codon for the n^th amino acid in the sequence.

Figure 11:
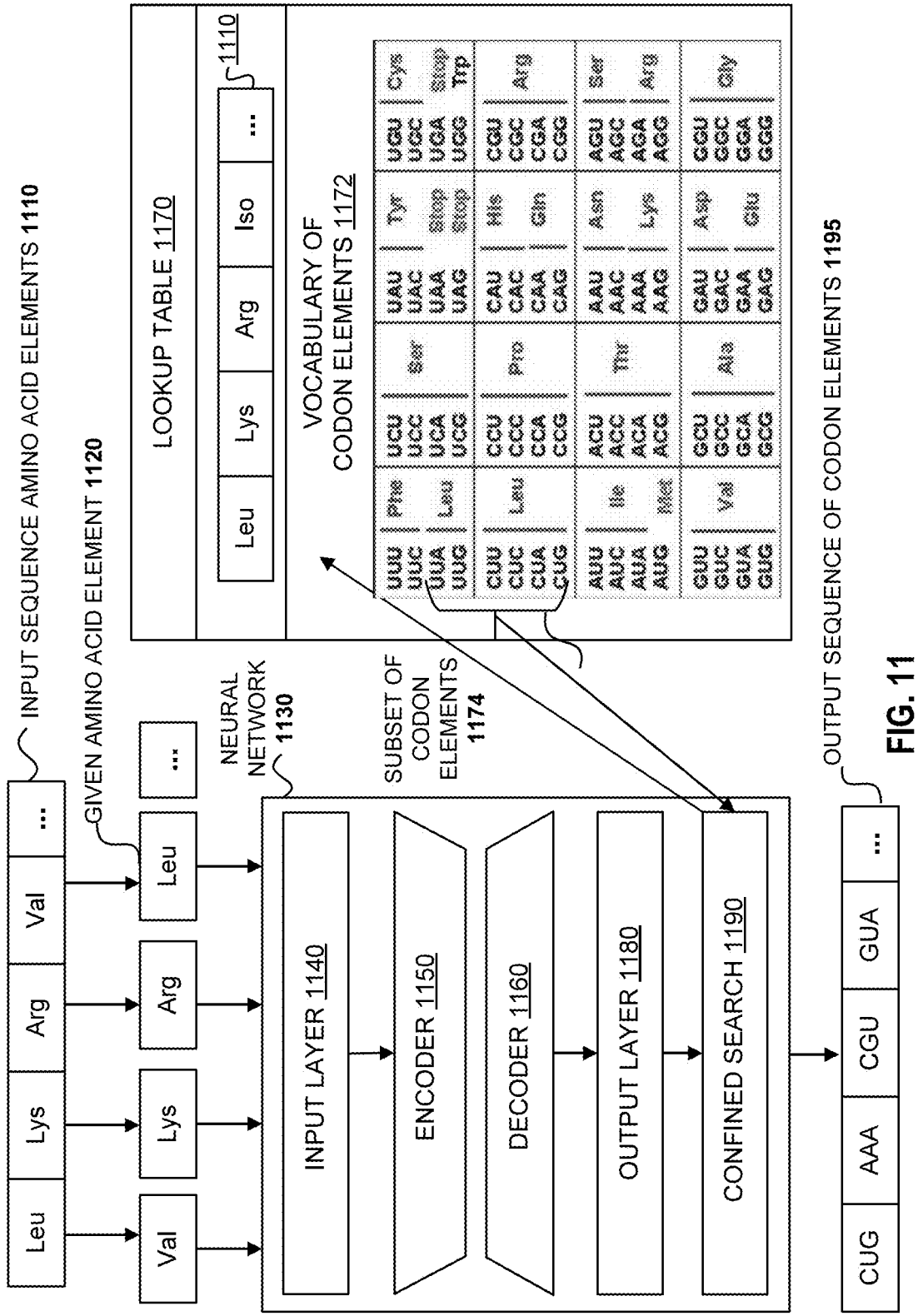
FIG. 11 shows one example of a confined search of a codon element within a sequence of codon elements.

FIG. 11 shows one example of a confined search for a given amino acid element within a sequence of amino acid elements 1100. A confined search for a given amino acid element within a sequence of amino acid elements 1100 may include processing an input sequence of amino acid elements 1110 and obtaining a given amino acid element 1120. For given amino acid element 1120, a corresponding codon element in a vocabulary of codon elements 1172 may be identified. Confining a search 1190 of the corresponding codon element in a vocabulary of codon elements 1172 to a subset of codon elements 1174 known to translate to the given amino acid element, may be performed. After processing, an output sequence of codon elements 1195 may be generated. A person of skill in the art will recognize that generating a prediction by looking back to confine the search to a subset of corresponding codons (e.g., a subset may include 1-6 codons per amino acid, according to the genetic code), instead of all 64 possible codons can provide an enormous speedup at runtime.

In one implementation, the confined search 1190 works after the output layer 1180. The confined search 1190 gets the probabilities for all codons from the output layer 1180. The probabilities are then passed to the confined search block 1190 that suppresses (i.e., sets to-infinity) any codon that is not relevant to the current amino acid that is being currently processed by the neural network 1130.

The confined search for a given amino acid element within a sequence of amino acid elements 1100 may be combined with other systems or methods of the present invention. For example, the protein-to-codon sequence mapping system 100 may be configured to include a confined search for a given amino acid element within a sequence of amino acid elements 1100.

A given amino acid element 1120 may be provided as input to a neural network 1130. Neural network 1130 can process the input sequence of amino acid elements 1110 and generate the output sequence of codon elements 1195.

As depicted in FIG. 11, neural network 1130 may be configured with an input layer 1140 to receive the input sequence of amino acid elements 1110. Input layer 1140 may convert the input sequence of amino acid elements 1110 from symbols into a numerical vector representation (tokenize, one-hot encode, etc.). Input sequence of amino acid elements 1110 may be further processed by layers of neural network 1130 to generate an output sequence of codon elements 1195 that corresponds to a protein with optimized expression.

Neural network 1130 may be a pre-trained neural network, or alternatively, neural network 1130 may be trained from scratch.

Neural network 1130 may perform a search in order to predict a codon sequence element for the corresponding given amino acid element 1120. In some implementations, prior to the search, a neural network component may look back (e.g., via lookup table 1170) at the input sequence of amino acid elements 1110 to determine an identity of the given amino acid element 1120. Then, the neural network component may use the determined identity of the given amino acid element 1120 to confine the search 1190 of the corresponding codon element to the subset of codon elements 1174 known to translate to the given amino acid element 1120.

For example, as depicted in FIG. 11, a given amino acid element (Leucine) 1120, may be received by neural network 1130 during inference to predict a corresponding codon sequence element. During processing and before performing a search, the decoder 1160, for example, may access lookup table 1170 to determine the identity of the given amino acid (Leucine) 1120 at that position of the input sequence of amino acid elements 1110. By determining the identity of the given amino acid (Leucine) 1120 and then determining a corresponding subset of codon elements (UUA, UUG, CUU, CUC, CUA, CUG) 1174, the search may be confined to the subset of 6 codons, instead of the set of all 64 codons (i.e., decoder 1160 is constrained to sampling a subset of 6 corresponding codons and SoftMax may generate a confined subset of 6 probabilities, instead of decoder 1160 sampling across the entire target codon vocabulary of 64 target codons and SoftMax generating 64 probabilities). One having skill in the art will appreciate that reducing the computation required for each position within the input sequence of amino acid elements 1110 will result in a very large savings in computational resources and time.

Neural network 1130 may use any suitable architecture and/or any suitable network layers to accomplish the intended goals. For example, neural network 1130 may be a sequence to sequence (Seq2Seq) neural network. In some implementations, neural network 1130 is an encoder 1150-decoder 1160 neural network (e.g., Transformer).

As depicted in FIG. 11, input sequence of amino acid elements 1110 may be received by an encoder 1150 neural network. In some implementations, the encoder 1150 neural network may generate respective embedded tokens for respective amino acid elements in the input sequence of amino acid elements 1110. In some implementations, the encoder 1150 neural network applies attention between the respective embedded tokens on an amino acid element-by-amino acid element. The context representation of the input sequence of amino acid elements 1110 may be provided to the decoder 1160 neural network.

The decoder 1160 neural network may receive the context representation of the input sequence of amino acid elements 1110. In some implementations of the confined search for a given amino acid 1100, the decoder 1160 neural network may receive results of the attention from the encoder 1150 neural network and may use the results of the attention to generate the output sequence of codon elements 1195. In other implementations of the confined search for a given amino acid 1100, the decoder 1160 neural network may look back (via lookup table 1170 or another approach) at the input sequence of amino acid elements 1110 to determine the identity of the given amino acid element 1120, and uses the determined identity of the given amino acid element to confine the search of the corresponding codon element to the subset of codon elements 1174 known to translate to the given amino acid element.

Figure 12:
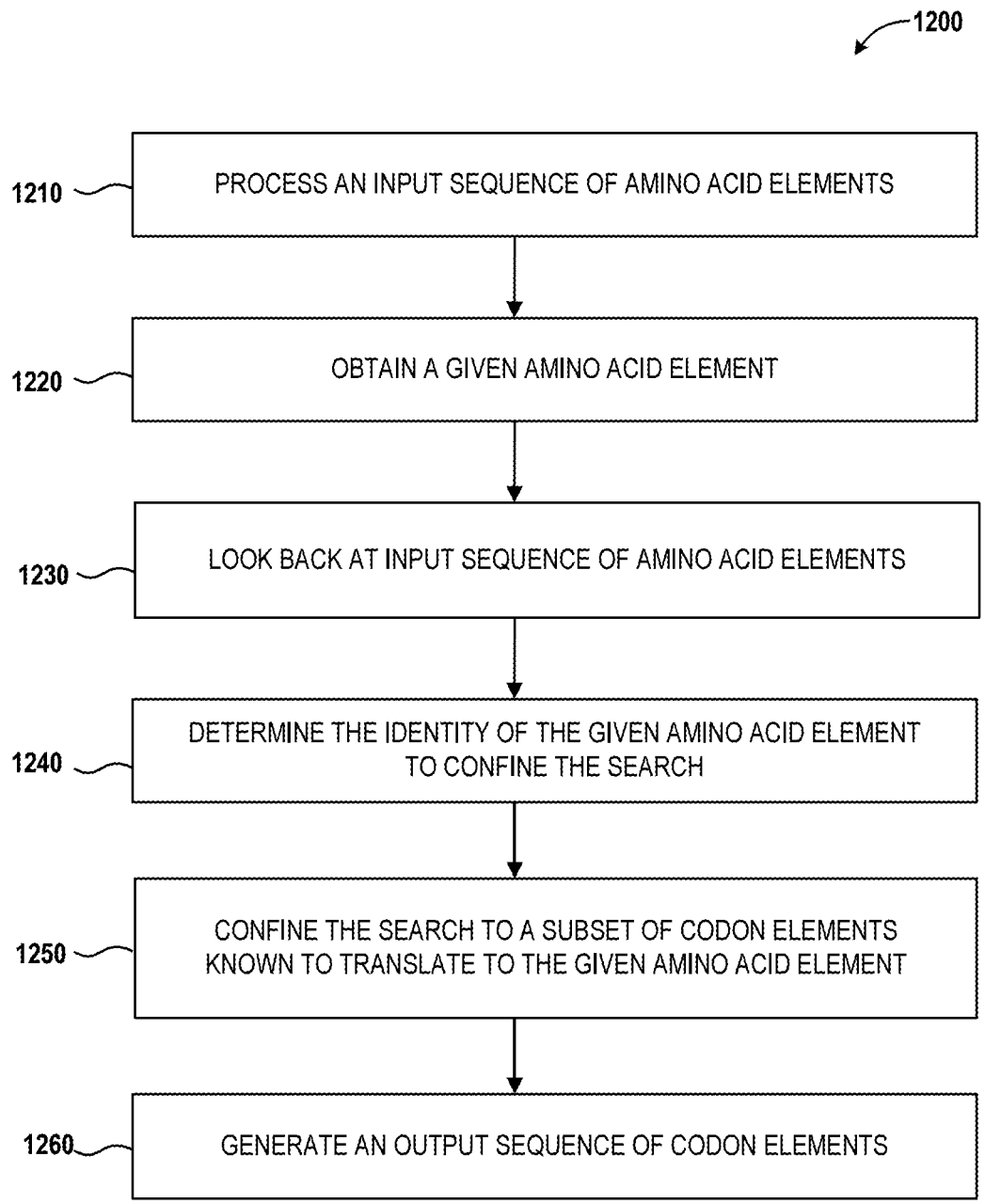
FIG. 12 is a flowchart of one example of generating an output sequence of codon elements by looking back to confine the search.

FIG. 12 is a flowchart of one example of generating an output sequence of codon elements by looking back to confine the search 1200. As depicted, the generating an output sequence of codon elements by looking back to confine the search method 1200 includes processing an input sequence of amino acid elements 1210, obtaining a given amino acid element 1220, looking back at the input sequence of amino acid elements 1230, determining the identity of the given amino acid element to confine the search 1240, confining the search to a subset of codon elements known to translate to the given amino acid element 1250, and generating an output sequence of codon elements 1260. One having skill in the art will appreciate the generating an output sequence of codon elements by looking back to confine the search method 1200 can provide an enormous speedup at runtime by placing a constraint on the number of codons for which a prediction will be made.

Processing an input sequence of amino acid elements 1210 may include the input layer of a neural network to receive the input sequence of amino acid elements. The symbolic text may be converted to a numerical representation of the input sequence of amino acid elements (e.g., via tokenizer, one-hot encoding, etc.). The neural network may generate a context vector or an embedding for predicting a codon sequence element. The neural network may comprise any architecture suitable for the task of generating optimized codon sequences.

Obtaining a given amino acid element 1220 may include a neural network receiving the given amino acid element for processing.

Looking back at the input sequence of amino acid elements 1230 may include a neural network component that determines the identity of the given amino acid element from the input sequence of amino acid elements. The term "looking back" may refer to. for example, accessing information about the input sequence of amino acid elements via a lookup table.

Determining the identity of the given amino acid element to confine the search 1240 may include a neural network component that searches and finds the correct position along the input sequence of amino acid elements.

Confining the search to a subset of codon elements known to translate to the given amino acid element 1250 may include searching the genetic code within a lookup table for a subset of codon elements that corresponds to the given amino acid element at the specified position of the input sequence of amino acid elements. Retrieving the subset of codon elements (for example, a range of 1-6 codons may correspond to a given amino acid element) from the lookup table for additional processing within the neural network. Based on the subset of corresponding codon elements, calculating a prediction probability for the subset of corresponding codon elements (i.e., for 1-6 codons) rather than a prediction probability for the entire set of all possible 64 codons.

Generating an output sequence of codon elements 1260 may include a neural network providing a predicted output sequence of codon elements that is an optimized codon sequence.

Figure 13:
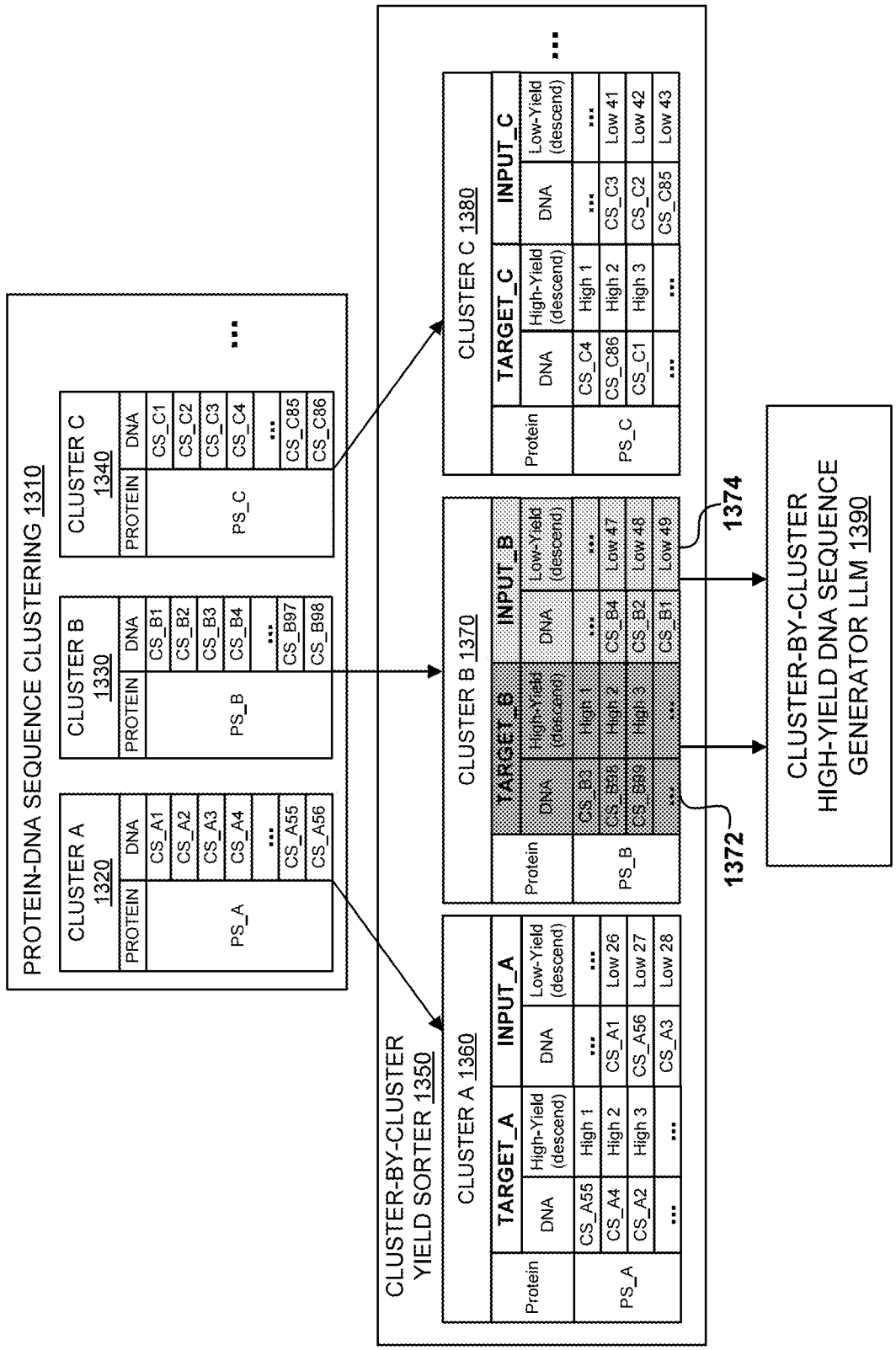
FIG. 13 shows training the cluster-by-cluster high-yield DNA sequence generator via supervised learning.

FIG. 13 shows a cluster-by-cluster, high-yield codon (DNA) sequence generator trained via supervised learning 1300. First, a lower-to-higher yield codon training dataset is created, which is then used to train the cluster-by-cluster high yield DNA generator 1390 on a cluster-basis. Training a cluster-by-cluster high-yield DNA sequence generator 1390 includes creating clusters of DNA sequences on an amino acid sequence-basis via protein-DNA sequence clustering 1310. Each protein-DNA sequence cluster may be sent to a cluster-by-cluster yield sorter 1350, wherein each protein-DNA sequence cluster remains in-tact. All DNA sequences within a single protein-DNA sequence cluster can be sorted by expression yield to generate lower-to-higher yield codon training dataset (for example, cluster B 1370). Then, the cluster-by-cluster high-yield DNA sequence generator LLM 1390 may be trained via supervised learning.

A large set of DNA sequences are obtained to build the lower-to-higher yield codon (DNA) training dataset (e.g., cluster B 1370). For example, DNA sequences based on labeled data, where labels may be obtained from transcriptomic labeling, can identify different DNA (codon) sequences that translate to the same amino acid sequence. In addition, clinical data can provide transcriptomic information. In some implementations, experimentally characterized data supplied information that may be used to generate at least some of the clusters of codon sequences. In another example, the protein-to-codon translator 150 and/or a protein-to-codon sequence mapping system 100 may provide source DNA (codon) sequences.

Protein-DNA sequence clustering 1310 may cluster DNA (codon) sequences based on their single corresponding protein sequence. Individual clusters of protein-DNA sequences can be formed, for example as depicted in FIG. 13, cluster A 1320 includes one protein sequence PS_A and multiple DNA sequences, CS_A1 through CS_A56. Each of the DNA sequences, CS_A1 through CS_A56, have a different DNA sequence that differs by one or more nucleotides (codons) from each of the other DNA sequences. Each of the DNA sequences, CS_A1 through CS_A56, corresponds to a single protein, PS_A. FIG. 13 is meant for illustrative purposes only, and it is not meant to limit the number of DNA sequences that may be clustered, sorted, or contained within a single cluster.

Cluster-by-cluster yield sorter 1350 receives each of the protein-DNA sequence clusters, such that each of the clusters remains in-tact and separated from other clusters. For example, as depicted in FIG. 13, cluster A 1320 is provided to cluster-by-cluster yield sorter 1350, and after being received by cluster-by-cluster yield sorter 1350, cluster A 1360 remains in-tact and separated from cluster B 1370 and cluster C 1380. All DNA sequences within a single cluster may be sorted by expression yield, low-yield to high-yield, and sorted relative to one another, to generate a lower-to-higher yield codon training dataset.

Training the cluster-by-cluster high-yield DNA sequence generator 1390 may be accomplished on a cluster-by-cluster basis. For example, as depicted in FIG. 13, cluster B 1370 has a group of high-yield (yield/expression) DNA sequences 1372 that are sorted in descending order by yield/expression and a group of low-yield DNA sequences 1374 that are sorted in descending order by yield/expression. The low-yield (yield/expression) DNA sequences 1374 may be input during training, while the high-yield DNA sequences 1372 may be target (or ground truth). The cluster-by-cluster high-yield DNA sequence generator 1390 receives input and target during supervised learning. The cluster-by-cluster high-yield DNA sequence generator 1390 is only trained on input/target DNA sequences corresponding to a single cluster (i.e., cluster B 1370) at a time.

After training, the trained cluster-by-cluster high-yield DNA sequence generator (for example 1460) may accept an inference input DNA sequence of any yield/expression and generate an inference output DNA sequence (i) that is of higher yield/expression than the input and (ii) that belongs to the same protein cluster. One having skill in the art will appreciate generating higher-yield/expression codon sequences that correspond to the same protein and therefore have retained and/or improved protein functionality.

The above description is intended to be an example and not limiting. For example, in some implementations, a lower-to-higher yield (yield/expression) codon training dataset may comprise protein embeddings and codon embeddings instead of sequences. Next, the cluster-by-cluster high-yield DNA sequence generator 1460 may be trained with a lower-to-higher yield (yield/expression) codon embedding training dataset. One having skill in the art will recognize that replacing sequences with embeddings to create a lower-to-higher yield (yield/expression) codon embedding training dataset provides more robustness for a smaller dataset. In other implementations, an appropriately trained cluster-by-cluster high-yield DNA sequence generator 1460 may receive an input protein sequence and may generate a high-yield (yield/expression) codon sequence. One having skill in the art will recognize the flexibility of cluster-by-cluster high-yield DNA sequence generator 1460.

Clustering Logic

The technology disclosed creates clusters of codon sequences on an amino acid sequence-basis. In some implementations, a particular cluster of codon sequences created for a particular amino acid sequence includes different codon sequences that translate to the particular amino acid sequence but have varying yields (i.e., yield/expression). In other implementations, the particular cluster of codon sequences is created by clustering based on one or more codon sequence attributes. In one implementation, the codon sequence attributes correspond to biological constraints of the different codon sequences that are to be clustered or sub-clustered. In some implementations, the biological constraints include identity similarity of the different codon sequences that are to be clustered or sub-clustered, homology of the different codon sequences that are to be clustered or sub-clustered, structural similarity of the different codon sequences that are to be clustered or sub-clustered, size of the different codon sequences that are to be clustered or sub-clustered, length of the different codon sequences that are to be clustered or sub-clustered, distribution of the different codon sequences that are to be clustered or sub-clustered, and rarity of the different codon sequences that are to be clustered or sub-clustered.

In some implementations, the particular cluster of codon sequences is created by clustering by clustering those codon sequences in a same cluster that have an identity score for at least one codon sequence identity higher than a similarity threshold. In one implementation, the codon sequence identity includes homology overlap between the codon sequences.

In another implementation, the codon sequences are embedded in an embedding space. The codon sequence identity includes embedding distances between the codon sequences in the embedding space. An embedding space in which the codon sequences are embedded, for example, to group/cluster/subcluster similar codon sequences in a latent space. A "latent space." for example, in deep learning is a reduced-dimensionality vector space of a hidden layer. A hidden layer of a neural network compresses an input and forms a new low-dimensional codon sequence with interesting properties that are distance-wise correlated in the latent space.

A distance is identified between each pair of the instances in the embedding space corresponding to a predetermined measure of similarity between the pair of the instances. The "embedding space." into which the instances are embedded, for example, by an embedding module (not shown), can be a geometric space within which the instances are represented. In one implementation, the embedding space can be a vector space (or tensor space), and in another implementation the embedding space can be a metric space. In a vector space, the features of an instance define its "position" in the vector space relative to an origin. The position is typically represented as a vector from the origin to the instance's position. and the space has a number of dimensions based on the number of coordinates in the vector. Vector spaces deal with vectors and the operations that may be performed on those vectors.

When the embedding space is a metric space, the embedding space does not have a concept of position, dimensions, or an origin. Distances among instances in a metric space are maintained relative to each other, rather than relative to any particular origin, as in a vector space. Metric spaces deal with codon sequences combined with a distance between those codon sequences and the operations that may be performed on those codon sequences.

For purposes of the present disclosure, these codon sequences are significant in that many efficient algorithms exist that operate on vector spaces and metric spaces. For example, metric trees may be used to rapidly identify codon sequences that are "close" to each other. Codon sequences can be embedded into vector spaces and/or metric spaces. In the context of a vector space, this means that a function can be defined that maps codon sequences to vectors in some vector space. In the context of a metric space, this means that it is possible to define a metric (or distance) between those codon sequences, which allows the set of all such codon sequences to be treated as a metric space. Vector spaces allow the use of a variety of standard measures of distance/ divergence (e.g., the Euclidean distance). Other implementations can use other types of embedding spaces.

As used herein, "an embedding" is a map that maps instances into an embedding space. An embedding is a function that takes, as inputs, a potentially large number of characteristics of the instance to be embedded. For some embeddings, the mapping can be created and understood by a human, whereas for other embeddings the mapping can be very complex and non-intuitive. In many implementations, the latter type of mapping is developed by a machine learning algorithm based on training examples, rather than being programmed explicitly.

In order to embed an instance in a vector space, each instance must be associated with a vector. A distance between two instances in such a space is then determined using standard measures of distance using vectors.

A goal of embedding instances in a vector space is to place intuitively similar instances close to each other. One way of embedding text instances is to use a bag-of-words model. The bag of words model maintains a dictionary. Each word in the dictionary is given an integer index, for example, the word aardvark may be given the index 1, and the word zebra may be given the index 60,000. Each instance is processed by counting the number of occurrences of each dictionary word in that instance. A vector is created where the value at the ith index is the count for the ith dictionary word. Variants of this codon sequence normalize the counts in various ways. Such an embedding captures information about the content and therefore the meaning of the instances. Text instances with similar word distributions are close to each other in this embedded space.

Images may be processed to identify commonly occurring features using, e.g., scale invariant feature transforms (SIFT), which are then binned and used in a codon sequence similar to the bag-of-words embedding described above. Further, embeddings can be created using deep neural networks, or other deep learning techniques. For example, a neural network can learn an appropriate embedding by performing gradient descent against a measure of dimensionality reduction on a large set of training data. As another example, a kernel can be learned based on data and derive a distance based on that kernel. Likewise, distances may be learned directly.

These approaches generally use large neural networks to map instances, words, or images to high dimensional vectors (for example see: A brief introduction to kernel classifiers, Mark Johnson, Brown University 2009, http://cs.brown.edu/courses/cs195-5/fall2009/docs/lecture_10-27.pdf "Using Confidence Bounds for Exploitation-Exploration Trade-offs, incorporated herein by reference; and Kernel Method for General Pattern Analysis, Nello Cristianini, University of California, Davis, accessed October 2016, http://www.kernel-methods.net/tutorials/KMtalk.pdf). In another example, image patches can be represented as deep embeddings. As an image is passed through a deep neural network model, the output after each hidden layer is an embedding in a latent space. These deep embeddings provide hints for the model to distinguish different images. In some implementations, the embeddings can be chosen from a low-dimensional layer as the latent codon sequence.

In other implementations, an embedding can be learned using examples with algorithms such as Multi-Dimensional Scaling, or Stochastic Neighbor Embedding. An embedding into a vector space may also be defined implicitly via a kernel. In this case, the explicit vectors may never be generated or used, rather the operations in the vector space are carried out by performing kernel operations in the original space.

Other types of embeddings of particular interest capture date and time information regarding the instance, e.g., the date and time when a photograph was taken. In such cases, a kernel may be used that positions images closer if they were taken on the same day of the week in different weeks, or in the same month but different years. For example, photographs taken around Christmas may be considered similar even though they were taken in different years and so have a large absolute difference in their timestamps. In general, such kernels may capture information beyond that available by simply looking at the difference between timestamps.

Similarly, embeddings capturing geographic information may be of interest. Such embeddings may consider geographic metadata associated with instances, e.g., the geo-tag associated with a photograph. In these cases, a kernel or embedding may be used that captures more information than simply the difference in miles between two locations. For example, it may capture whether the photographs were taken in the same city, the same building, or the same country.

Often embeddings will consider instances in multiple ways. For example, a product may be embedded in terms of the metadata associated with that product, the image of that product, and the textual content of reviews for that product. Such an embedding may be achieved by developing kernels for each aspect of the instance and combining those kernels in some way, e.g., via a linear combination.

In many cases a very high dimensional space would be required to capture the intuitive relationships between instances. In some of these cases, the required dimensionality may be reduced by choosing to embed the instances on a manifold (curved surface) in the space rather than to arbitrary locations.

Different embeddings may be appropriate on different subsets of the instance catalog. For example, it may be most effective to re-embed the candidate result sets at each iteration of the search procedure. In this way, the subset may be re-embedded to capture the most important axes of variation or of interest in that subset.

To embed an instance in a metric space requires associating that catalog with a distance (or metric).

A "distance" between two instances in an embedding space corresponds to a predetermined measurement (measure) of similarity among instances. Preferably, it is a monotonic function of the measurement of similarity (or dissimilarity). Typically, the distance equals the measurement of similarity. Example distances include the Manhattan distance, the Euclidean distance, the Hamming distance, and the Mahalanobis distance.

Given the distance (similarity measure) between instances to be searched, or the embedding of those instances into a vector space, a metric space or a manifold, there are a variety of data structures that may be used to index the instance catalog and hence allow for rapid search. Such data structures include metric trees, kd-trees, R-trees, universal B-trees, X-trees, ball trees, locality sensitive hashes, and inverted indexes. The technology disclosed can use a combination of such data structures to identify a next set of candidate results based on a refined query. An advantage of using geometric constraints is that they may be used with such efficient data structures to identify the next results in time that is sub-linear in the size of the catalog.

There are a wide variety of ways to measure the distance (or similarity) between instances, and these may be combined to produce new measures of distance. An important concept is that the intuitive relationships between digital instances may be captured via such a similarity or distance measure. For example, some useful distance measures place images containing the same person in the same place close to each other. Likewise, some useful measures place instances discussing the same topic close to each other. Of course, there are many axes along which digital instances may be intuitively related, so that the set of all instances close (with respect to that distance) to a given instance may be quite diverse. For example, a historical text describing the relationship between Anthony and Cleopatra may be similar to other historical texts, texts about Egypt, texts about Rome, movies about Anthony and Cleopatra, and love stories. Each of these types of differences constitutes a different axis relative to the original historical text.

Such distances may be defined in a variety of ways. One typical way is via embeddings into a vector space. Other ways include encoding the similarity via a kernel. By associating a set of instances with a distance, we are effectively embedding those instances into a metric space. Instances that are intuitively similar will be close in this metric space while those that are intuitively dissimilar will be far apart. Note further that kernels and distance functions may be learned. In fact, it may be useful to learn new distance functions on subsets of the instances at each iteration of the search procedure.

Note that wherever a distance is used to measure the similarity between instances a kernel may be used to measure the similarity between instances instead, and vice-versa. However, kernels may be used directly instead without the need to transform them into distances.

Kernels and distances may be combined in a variety of ways. In this way, multiple kernels or distances may be leveraged. Each kernel may capture different information about an instance, e.g., one kernel captures visual information about a piece of jewelry, while another captures price, and another captures brand.

Also note that embeddings may be specific to a given domain, such as a given catalog of products or type of content. For example, it may be appropriate to learn or develop an embedding specific to men's shoes. Such an embedding would capture the similarity between men's shoes but would be uninformative with regards to men's shirts.

In other implementations, instead of a distance function, a similarity function can be used, for example, to group/cluster/subcluster visually similar images in a latent space. The similarity function, which is used to determine a measure of similarity, can be any function having kernel properties, such as but not limited to a dot product function, a linear function, a polynomial function, a Gaussian function, an exponential function, a Laplacian function, an analysis of variants (ANOVA) function, a hyperbolic tangent function, a rational quadratic function, a multi-quadratic function, an inverse multi-quadratic function, a circular function, a wave function, a power function, a log function, a spline function, a B-spline function, a Bessel function, a Cauchy function, a chi-square function, a histogram intersection function, a generalized histogram intersection function, a generalized T-student function, a Bayesian function, and a wavelet function.

In the above-described context, using similarity functions, as opposed to using distance functions, is better because neural networks are often trained with regularizers, which add an ever-increasing cost in order to reach the training objective as the weights of the neural network get larger. These regularizers are added to prevent overfitting, where the network pays undue attention to details in the training data, instead of identifying broad trends. Further, these regularizers may be viewed as applying pressure toward a default behavior, which must be overcome by the training data. When used for learning embeddings, standard regularizers have an effect of pushing the embeddings toward an origin, which tends to push them closer together. If one uses a goal to achieve large distances when items are dissimilar, then this sort of regularization pushes towards a default that items will be similar. However, if a goal is set to have the embeddings have a large dot product when the items are similar (as in the case of the above-described similarity function), then the regularizer applies pressure towards a default that items are dissimilar. It will often be the case that a typical random pair of instances should be regarded as dissimilar. An overall more accurate and efficient visual image discovery results.

Figure 14:
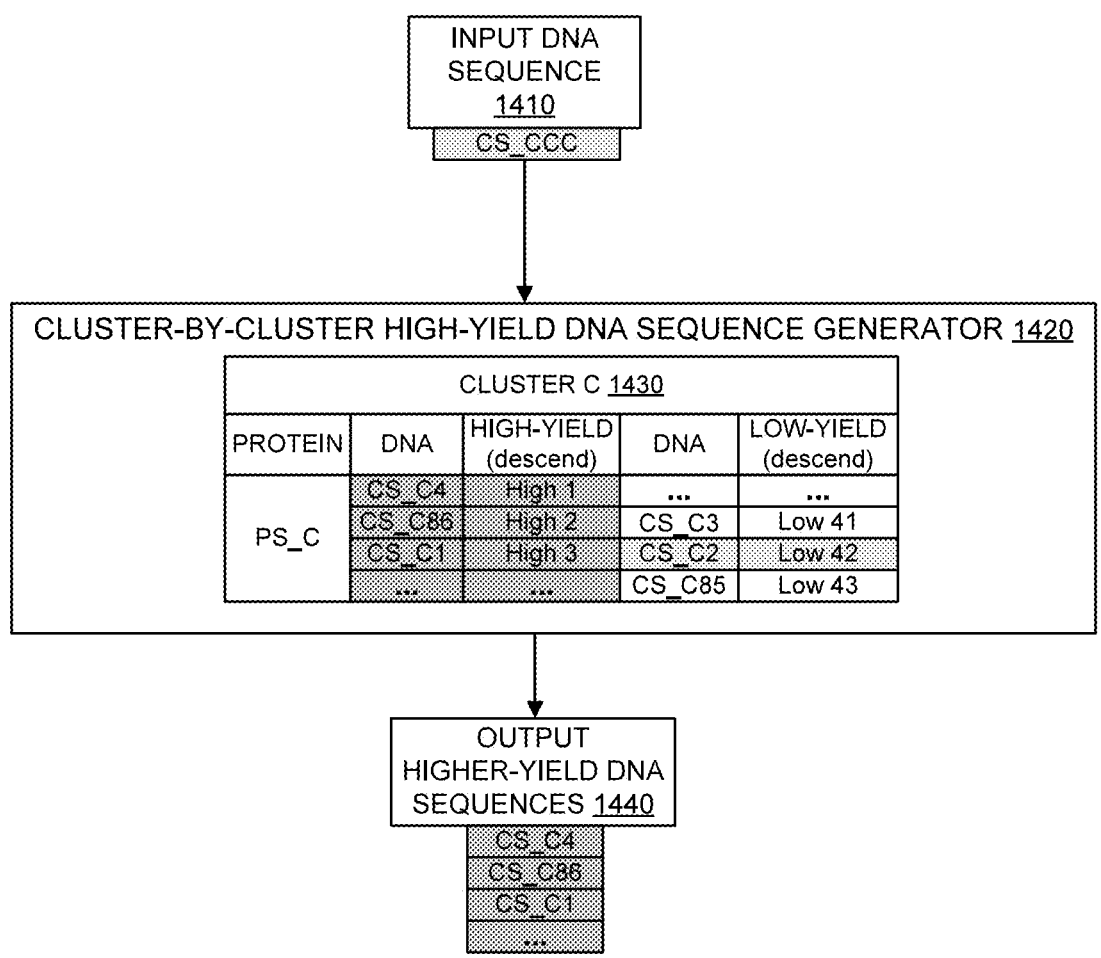
FIG. 14 shows generating the high-yield DNA sequence output via the trained cluster-by-cluster high-yield DNA sequence generator.

FIG. 14 shows generating the output higher-yield DNA sequence 1440 via the trained cluster-by-cluster high-yield DNA sequence generator 1420. During inference, a trained cluster-by-cluster high-yield DNA sequence generator 1420 may receive an input DNA sequence 1410 and, after processing, generate an output higher-yield (i.e., yield/expression) DNA sequence 1440 with the same corresponding protein sequence.

Trained cluster-by-cluster high-yield DNA sequence generator 1420 was trained using the Protein-DNA sequence cluster 1430 (labeled "Cluster C"). such that the model learned high-yield (i.e., yield/expression) DNA sequence features and low-yield (i.e., yield/expression) DNA sequence features that all correspond to the same protein ("PS_C"). At inference. trained cluster-by-cluster high-yield DNA sequence generator 1420 receives input DNA sequence 1410 (labeled as "CS_CCC") that is known to code for the same protein ("PS_C"). At inference. one or more output higher-yield codon sequences 1440 may be generated, that all correspond to the same protein sequence (PS_C) as the input sequence and all have higher expression yield than input DNA sequence 1410. One having skill in the art will appreciate the ease of accessing one or more valid DNA sequences having a higher yield/expression and known to code for the same protein of interest.

Figure 15:
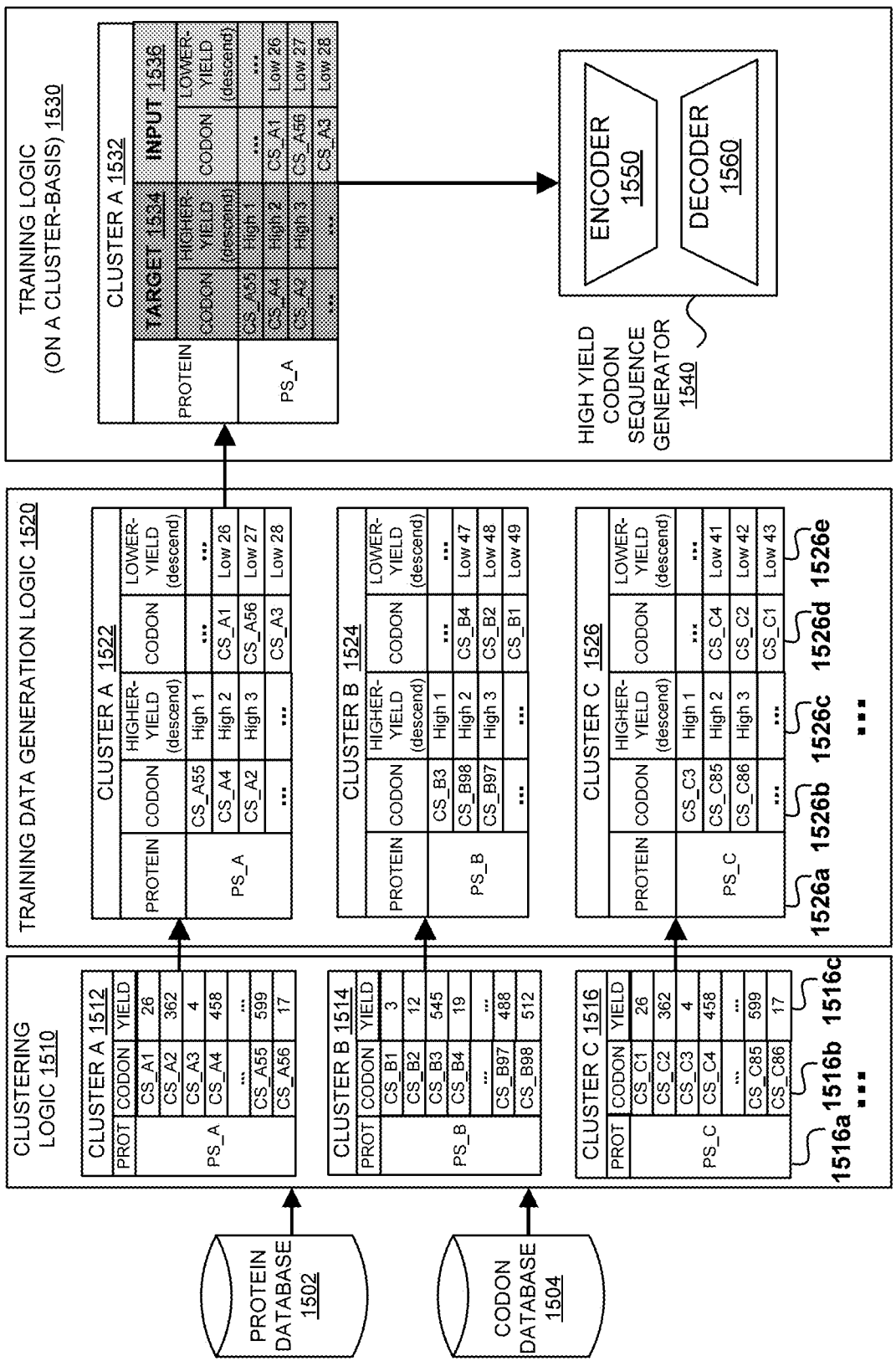
FIG. 15 shows the supervised machine translation technique to train the high-yield codon sequence generator.

FIG. 15 shows the supervised machine translation technique 1500 to train the high-yield codon sequence generator 1540. First, to generate high-yield codon sequences, a series of protein and codon sequences may be received by clustering logic 1510 that creates clusters of codon sequences on an amino acid sequence-basis. The clusters of codon sequences (for example, Cluster C 1516) may be used to build a lower-to-higher yield codon training dataset (for example, Cluster C 1526). The lower-to-higher yield codon training dataset (for example, Cluster C 1526) can be used to train a high-yield codon sequence generator 1540 to map the lower-yield input codon sequences (e.g., 1526d and 1526e) to the higher-yield target codon sequences (e.g., 1526b and 1526c).

Input protein sequences and codon sequences may be retrieved from protein database 1502 and codon database 1504 and then provided to a clustering logic 1510. Protein and codon sequences may be derived from several sources, such as clinical data, databases, or others. In addition, input protein sequences and codon sequences may be processed via a pre-trained protein language model (e.g., 630) and pre-trained DNA language model (e.g., 640), respectively, to generate high dimensional protein embeddings and codon embeddings as input.

Clustering logic 1510 processes the protein and codon sequences to generate protein-codon sequence clusters (e.g., Cluster A 1512, Custer B 1514, Cluster C 1516). Each cluster includes only one protein sequence 1516a and more than one codon sequence 1516b that differs by at least one codon (for example, Cluster A 1512 includes PS_A and multiple codon sequences CS_A1 to CS_A56). Each codon sequence 1516b has an associated expression yield 1516c. In some implementations, a particular cluster of codon sequences 1516b created for a particular amino acid sequence 1516a includes different codon sequences that translate to the particular amino acid sequence but have varying yields/expression 1516c. Moreover, at least some of the clusters of codon sequences are generated based on clinical data that identify different codon sequences that translate to the same amino acid sequence.

Some of the clusters of codon sequences are generated based on an amino acid sequence-to-codon sequence generator generating different output codon sequences for a same input amino acid sequence. In some implementations, the amino acid sequence-to-codon sequence generator is a neural network. In other implementations, the amino acid sequence-to-codon sequence generator that is a neural network, may be a pre-trained neural network. In some implementations, the amino acid sequence-to-codon sequence generator that is a neural network, may be an untrained neural network. In other implementations, the amino acid sequence-to-codon sequence generator that is a neural network, may be a sequence to sequence (seq2seq) neural network. Still in other implementations, the amino acid sequence-to-codon sequence generator that is a neural network, may be an encoder-decoder neural network (e.g., Transformer).

The protein-codon sequence clusters may be received by training data generation logic 1520. Protein-codon sequence clusters remain in-tact throughout downstream logic and when moving between downstream logic units. In addition, clusters are processed by logic on a cluster-by-cluster basis. For example, as shown in FIG. 15, after Cluster A 1512 is formed by clustering logic 1510, then the cluster remains in-tact when received and processed by training data generation logic 1520 into Cluster A 1522.

Training data generation logic 1520 sorts the codon sequences within each of the clusters of codon sequences by yield/expression. For example, in Cluster C 1526, all codon sequences are sorted based on yield/expression into a higher-yield (i.e., yield/expression) codon 1526b grouping and a lower-yield (i.e., yield/expression) codon 1526d grouping.

A single protein-codon sequence cluster 1532 may be received by training logic (on a cluster-basis) 1530, in order to train high-yield codon sequence generator 1540 on a cluster-basis. By processing the lower-to-higher yield codon training dataset 1532, training logic 1530 can link lower-yield input 1536 codon sequences to higher-yield target 1534 codon sequences. Specifically, on a cluster-basis, codon sequences in which one codon sequence has a lower-yield/expression and another codon sequence has a higher-yield/expression can be generated into pairs of codon sequences. With reference to FIG. 15 for example, a lower yield/expression codon sequence, such as CS_A52 (with yield/expression of Low 27), can be paired with a higher-yield/expression codon sequence, such as CS_A2 (with yield/expression of High 3).

After pairing the lower-yield (expression) and higher-yield (expression) codon sequences, then input 1536 and target 1534 (ground truth) groups may be created for training the high-yield codon sequence generator 1540 via supervised learning. From the paired codon sequences, the codon sequence with the lower yield/expression in the lower-to-higher yield codon training dataset 1532 may be included as a lower-yield input 1536 codon sequence. Similarly, from the paired codon sequences, the codon sequence with the higher-yield/expression in the lower-to-higher yield codon training dataset 1532 may be included as a higher-yield input 1534 codon sequence.

High-yield codon sequence generator 1540 is a neural network or any suitable architecture. In some implementations, high-yield codon sequence generator 1540 is a sequence to sequence (seq2seq) neural network. In other implementations, high-yield codon sequence generator 1540 is an encoder-decoder neural network (e.g., Transformer). As depicted in FIG. 15, high-yield codon sequence generator 1540 has an encoder 1550 network and a decoder 1560 network.

In some implementations, high-yield codon sequence generator 1540 is an untrained neural network. In other implementations, high-yield codon sequence generator 1540 is a pre-trained neural network.

High-yield codon sequence generator 1540 may be trained via a supervised learning technique with the lower-yield input 1536 codon sequences and the higher yield target sequences. Training high-yield codon sequence generator 1540 includes training with a single lower-to-higher yield codon training dataset 1532, corresponding to one cluster (Cluster A), at a time.

During inference, the trained high-yield codon sequence generator may generate a higher-yield (i.e., yield/expression) codon sequence, for example, that corresponds to the protein of Cluster A 1532.

Figure 16:
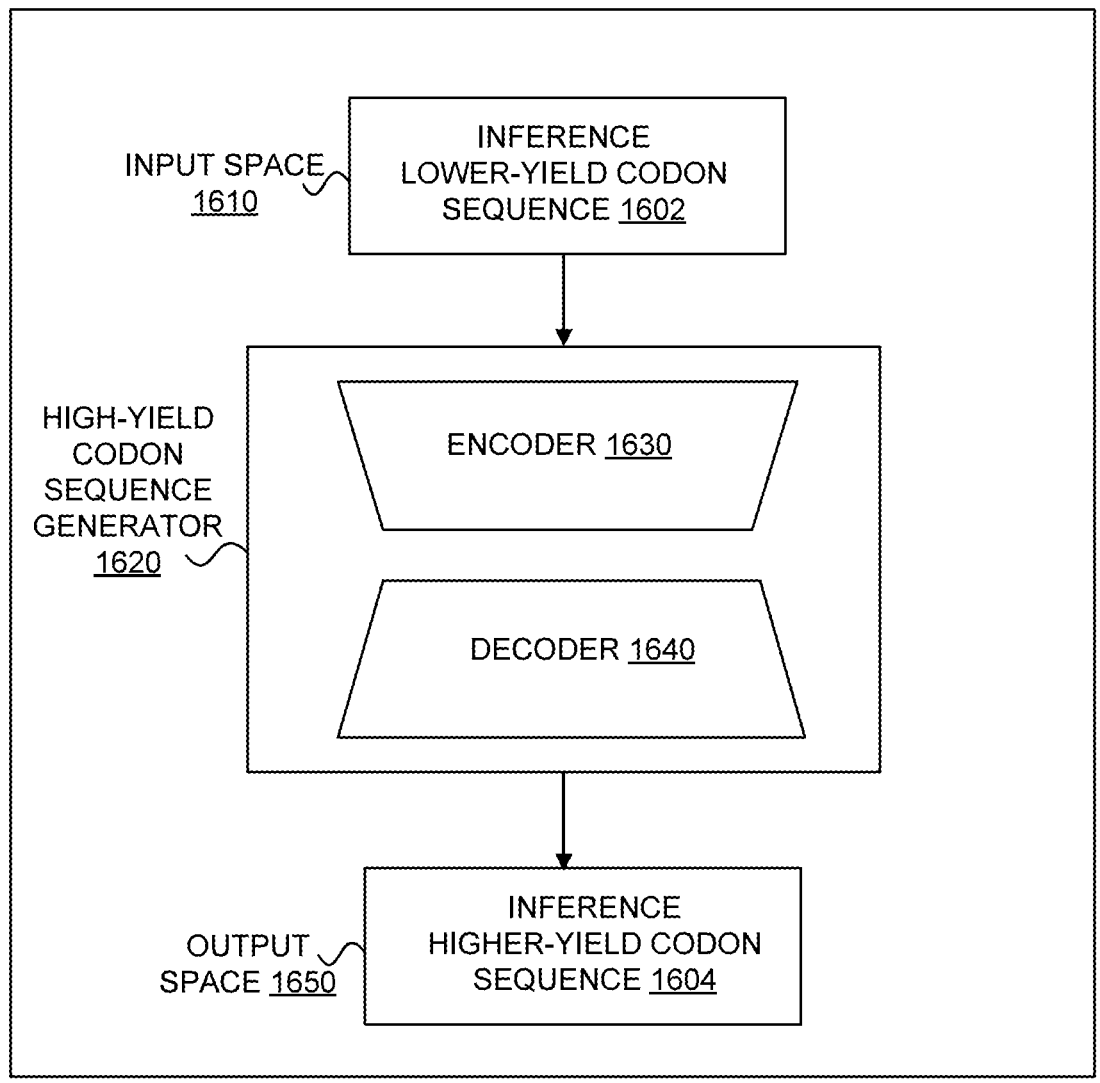
FIG. 16 shows one example of a high-yield codon sequence generator system.

FIG. 16 shows one example of a high-yield codon sequence generator system 1600. During inference, for example, input space 1610 receives inference lower-yield (i.e., yield/expression) codon sequence 1602 for processing by high-yield codon sequence generator 1620. After processing, high-yield codon sequence generator 1620 may generate an inference higher-yield (i.e., yield/expression) codon sequence 1604 in output space 1650. High-yield codon sequence generator 1620 may have any suitable architecture, including an encoder 1630 network and a decoder 1640 network.

Figure 17:
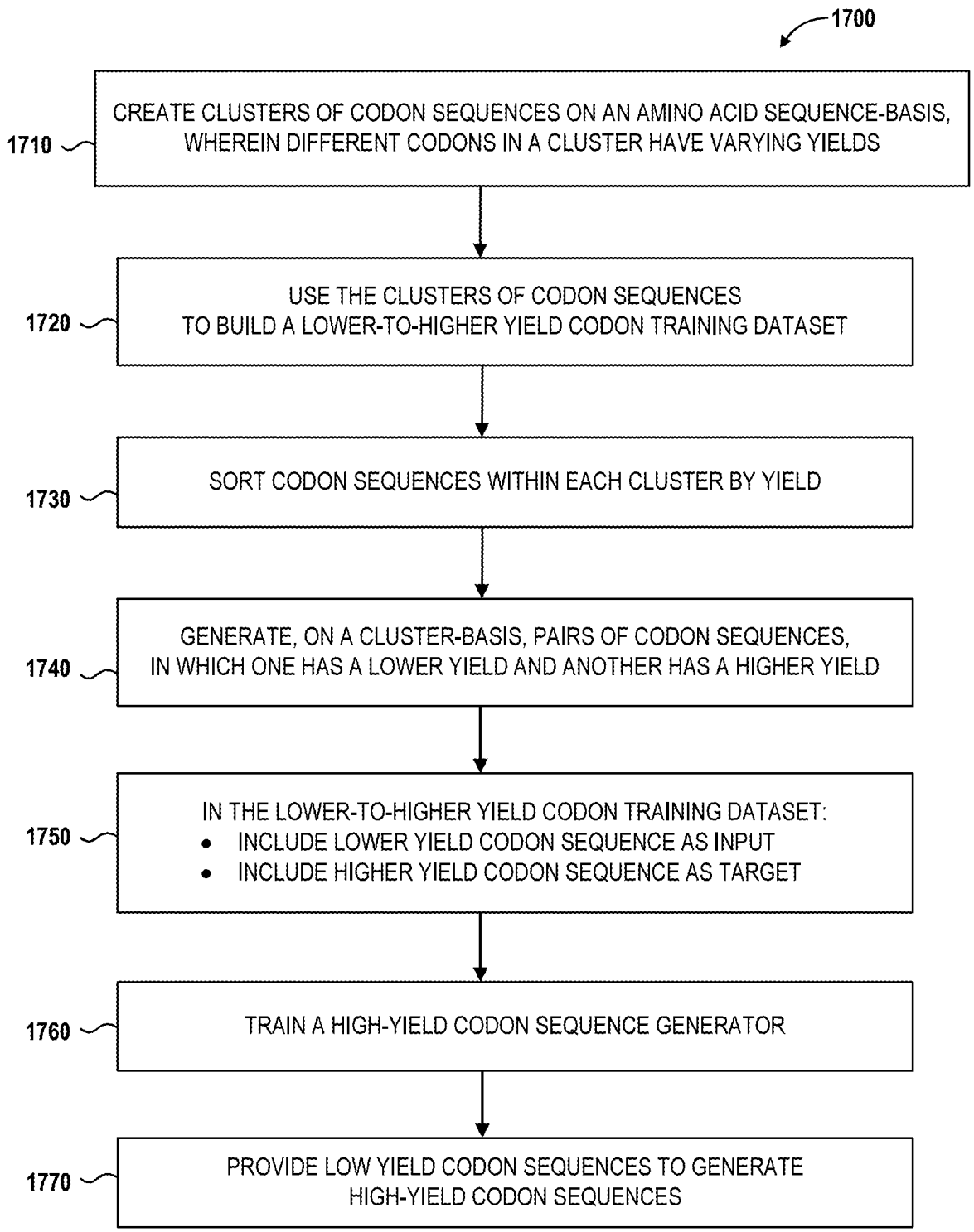
FIG. 17 is a flowchart of one example of generating higher yield codon sequences.

For example, the high-yield codon sequence generator 1620 may be trained via supervised machine high-yield codon generation technique 1500. During inference, a trained high-yield codon sequence generator 1620 may receive an inference lower-yield (i.e., yield/expression) codon sequence 1602 and, after processing, generate inference higher-yield (i.e., yield/expression) codon sequence 1604 corresponding to the same protein sequence as inference lower-yield (i.e., yield/expression) codon sequence 1602 (i.e., if inference lower-yield/expression and higher-yield/expression codon sequences are expressed, then expression of the same protein would result). One having skill in the art will appreciate the ease of accessing one or more valid higher-yield/expression DNA sequences FIG. 17 is a flowchart of one example of generating higher yield codon sequences 1700. As depicted, the generating higher-yield (i.e., yield/expression) codon sequences method 1700 includes creating clusters of codon sequences on an amino acid sequence-basis 1710 and using the clusters of codon sequences to build a lower-to-higher yield codon training dataset 1720. Building the lower-to-higher yield codon training dataset, method 1700 can include sorting codon sequences within each cluster by yield 1730, generating on a cluster-basis pairs of codon sequences 1740, including lower yield codon sequence as input 1750, and including higher yield codon sequence as target 1750. After building the lower-to-higher yield codon training dataset, method 1700 may include training a high-yield codon sequence generator 1760. After training, method 1700 may include providing low yield codon sequences to generate high-yield codon sequences 1770.

Transformer models process input tokes and generate query, key, and value vectors. Transformer models use self-attention to turn these vectors into attention scores. Positional encodings like rotary relative position embedding (RoPE) and Attention with Linear Biases (ALiBi) are used to negate any absolute positional information of the input tokens and to only retain information about the relative angles between every pair of word embeddings (e.g., amino acids) in a sequence (e.g., protein). Positional encodings exist that can vary the relative angles between amino acids. However, this variation is currently restricted to the confines of a given attention head. An opportunity arises to further vary the relative angles between the amino acids across different heads of a Transformer architecture.

The technology disclosed extends positional encodings like ROPE and ALiBI by applying a series of rotation matrices to the query and key vectors at different scaled frequencies that vary both by absolute position so the query and key vectors and by the different attention heads. For example, positional encodings like RoPE and ALiBI scale the query and key vectors by using absolute positions of the query and key vectors as scaling parameters. These absolute positions are expressed by position indices. The technology disclosed adds an additional degree of variability to the positional encodings by further multiplying the position indices with an additional scaling factor, referred to herein as "head-specific scaling parameter." This additional scaling factor is specific to a given attention head and varies across the attention heads of the Transformer architecture. Furthermore, from one attention head to the next, this additional scaling factor can vary in a pattern, for example, change in multiples.

Figure 18:
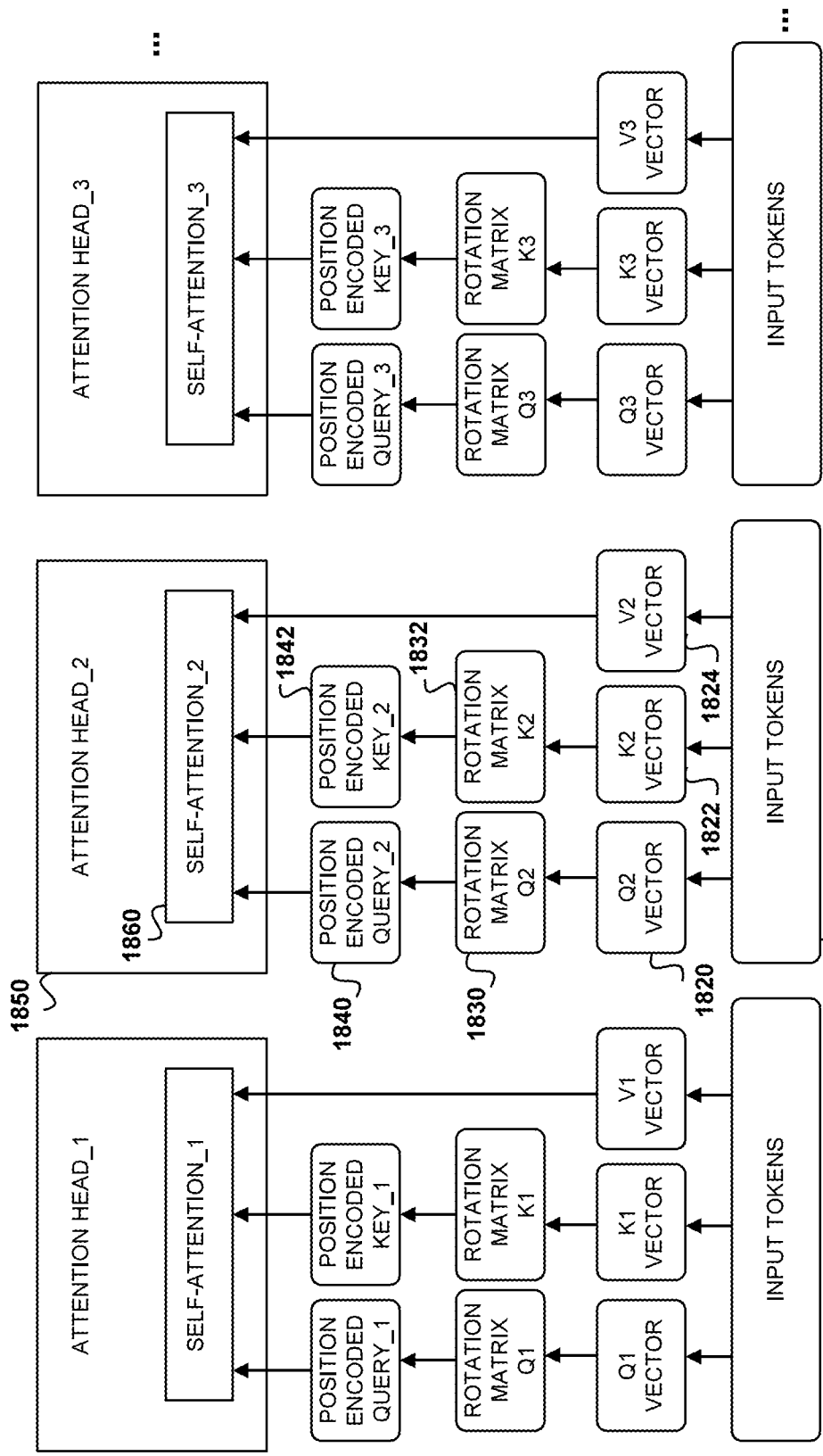
FIG. 18 shows one example of a relative positional embedding to a multi-head attention transformer system.

FIG. 18 shows one example of relative positional embedding provided to a multi-head attention Transformer system. Providing relative positional embedding to a multi-head Transformer model may include providing input tokens 1810, to respective attention heads, such as attention head_2 (1850), of the multi-head attention Transformer model. The input tokens 1810 may be used to generate respective query (Q), key (K), and value (V) vectors to be provided to respective attention. For example, input tokens 1810 may be used to generate Q2 vector 1820, K2 vector 1822, and V2 vector 1824.

Query and key vectors may be converted into position-encoded query and key vectors by applying a series of rotation matrices. As depicted in FIG. 18, Q2 vector 1820 and K2 vector 1822 may be converted into position-encoded query_2 vector 1840 and position-encoded key_2 vector 1842, respectively, via application of rotation matrix Q2 (1830) and rotation matrix K2 (1832). Rotation matrices may be applied to the query and key vectors at different scaled frequencies that vary by absolute positions of the query and key vectors and by the respective attention heads.

For example, application of the series of rotation matrices may include rotating pairs of feature dimensions in the query and key vectors by an angle in multiples of a scaled position index of a corresponding query or key vector. The scaled position index may be scaled by a head-specific scaling parameter that varies across the respective attention heads. In some implementations, the head-specific scaling parameter may be a head-specific scaling scalar.

The position-encoded query and key vectors may be used for execution of self-attention by the respective attention heads to generate pairwise attention scores that depend on relative positions of input token pairs and on their feature similarity. As depicted in FIG. 18, position-encoded query_2 vector 1840 and position-encoded key vector 1842 may be used for execution of self-attention_2 (1860) by respective attention head_2 (1850) to generate pairwise attention scores.

Pairwise attention scores that are generated may depend on relative positions of input token pairs and on their feature similarity. For example, the pairwise attention scores may be penalized based on how far the position-encoded query and key vectors are located from one another. In some implementations, when a position-encoded query vector and a position-encoded key vector are close by, then the attention score penalty may be very low. In some implementations, when a position-encoded query vector and a position-encoded key vector are far away, then the attention score penalty may be very high.

In some implementations, the input token pairs may be amino acid token pairs. In other implementations, the input token pairs can be nucleotide token pairs.

One having skill in the art will recognize the relative positional embedding to a multi-head attention Transformer model can overcome the limitations arising from the longer sequence length, the nature of the sequence resulting folding, and the corresponding scaled number of parameters. Specifically, different scaling may be performed on each attention head that is proportional to its context length.

In another example, given a vector, Q, of length R, where Q is a vector of positions (e.g. [1, 2, 3, 4, 5, 6, ... R]) where R is the sequence length. By multiplying vector Q with a certain scalar (referred to herein as a "scaling parameter" or "head-specific scaling parameter") such that the scalar changes on each head, then the amount of rotation changes for each word and the amount of rotation changes for each of the other words in each of the other attention heads.

To illustrate the above, vector Q, with length R, may be Q=[1, 2, 3, 4, 5, 6, ... R]. If given S attention heads, then it may follow that:

At the 1st head: Q will be scaled by 0.5 (e.g. Q*0.5)
At the 2nd head: Q will be scaled by 0.25 (e.g. Q*0.25)
At the 3rd head: Q will be scaled by 0.125 (e.g. Q*0.125)
And so on, until the Sth attention head.

One having skill in the art will recognize that relative positional embedding to a multi-head Transformer model may be especially beneficial for predicting longer amino acid sequence embeddings that surpass the relative positional embedding dimension. The relative positional embedding to a multi-head Transformer may extend the context length to sustain relationships between distant tokens of an input sequence, which is of high importance in protein sequence modeling.

Figure 19:
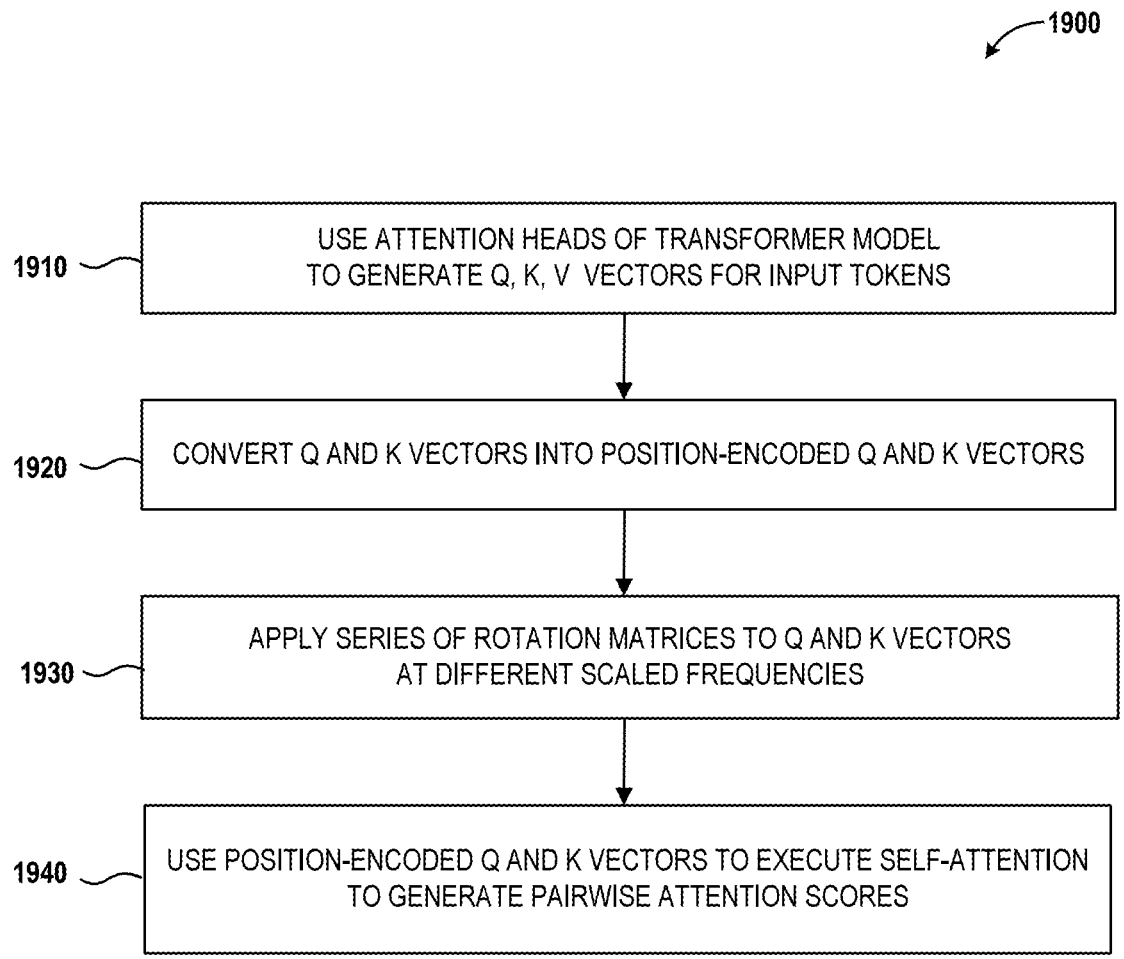
FIG. 19 is a flowchart of one example of providing relative positional embedding to a multi-head attention transformer.

FIG. 19 is a flowchart of one example of a method of providing relative positional embedding to a multi-head attention Transformer 1900. The exemplary method of FIG. 19 depicts using attention heads of a multi-head attention Transformer model to generate query (Q), key (K), and value (V) vectors 1910. Another method step may include converting query (Q) vectors and key (K) vectors into position-encoded query (Q) and key (K) vectors 1920. Forming position-encoded Q and K vectors may be accomplished by applying a series of rotation matrices to Q and K vectors at different scaled frequencies 1930. For example, the different scaled frequencies may vary by absolute positions of the query and key vectors and by the respective attention heads. In some embodiments, application of the series of rotation matrices may include rotating pairs of feature dimensions in the query and key vectors by an angle in multiples of a scaled position index of a corresponding query or key vector. FIG. 19 also depicts using position-encoded query and key vectors for execution of self-attention by the respective attention heads to generate pairwise attention scores that depend on relative positions of input token pairs and on their feature similarity 1940. One having skill in the art will recognize that relative positional embedding to a multi-head Transformer model may be especially beneficial for predicting longer amino acid sequence embeddings that surpass the relative positional embedding dimension.

Computer System

Figure 20:
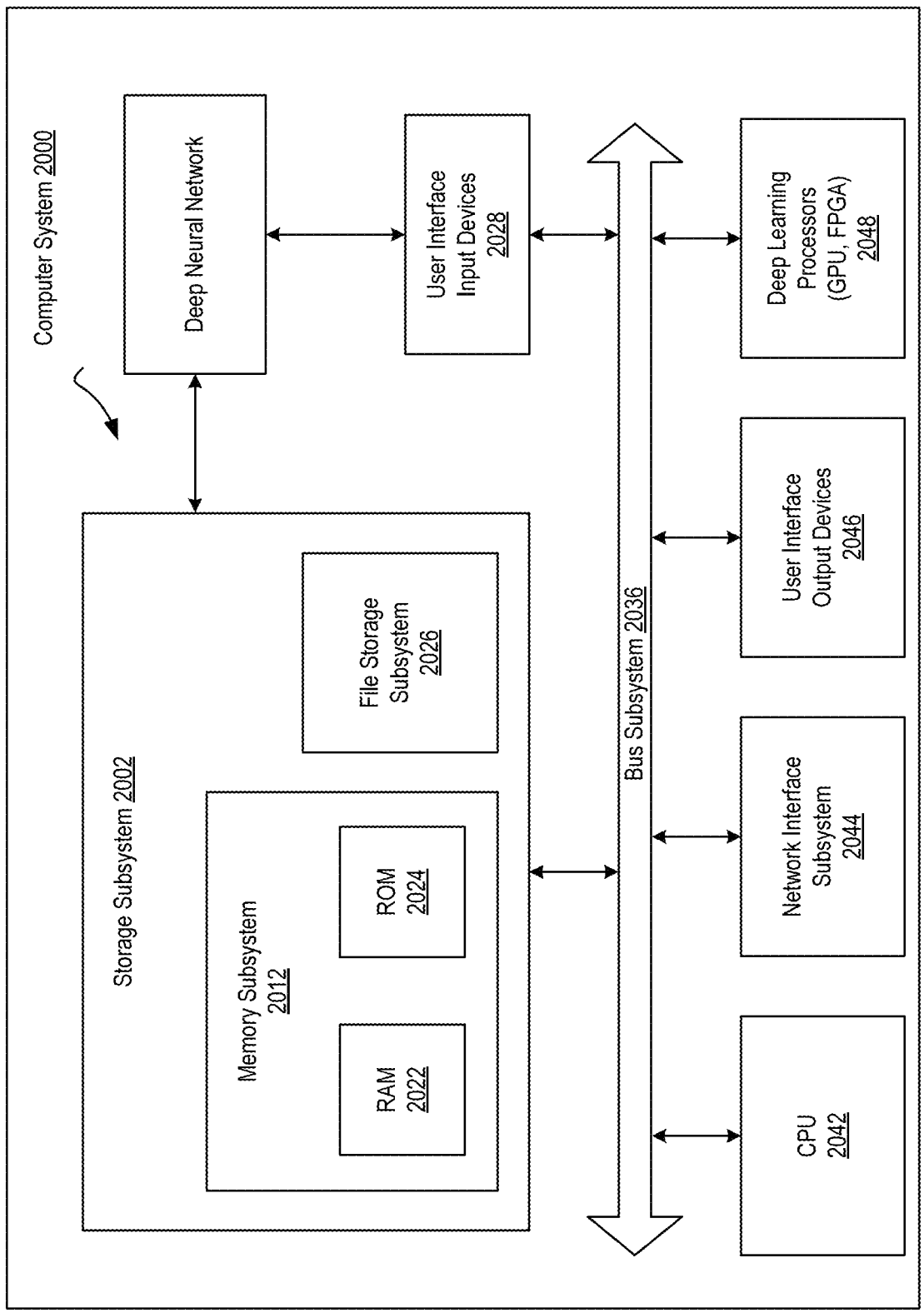
FIG. 20 is a simplified block diagram of a computer system that can be used to implement the technology disclosed.

FIG. 20 shows an example computer system 2000 that can be used to implement the technology disclosed. Computer system 2000 includes at least one central processing unit (CPU) 2042 that communicates with a number of peripheral devices via bus subsystem 2026. These peripheral devices can include a storage subsystem 2002 including, for example, memory devices and a file storage subsystem 2026, user interface input devices 2028, user interface output devices 2046, and a network interface subsystem 2044. The input and output devices allow user interaction with computer system 2000. Network interface subsystem 2044 provides an interface to outside networks, including an interface to corresponding interface devices in other computer systems.

In one implementation, the deep neural network like the large language models disclosed here is communicably linked to the storage subsystem 2002 and the user interface input devices 2028.

User interface input devices 2028 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2000.

User interface output devices 2046 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2000 to the user or to another machine or computer system.

Storage subsystem 2002 stores programming and data constructs that provide the functionality of some or all of the modules and methods described herein. These software modules are generally executed by processors 2048.

Processors 2048 can be graphics processing units (GPUs), field-programmable gate arrays (FPGAs), application-specific integrated circuits (ASICs), and/or coarse-grained reconfigurable architectures (CGRAs). Processors 2048 can be hosted by a deep learning cloud platform such as Google Cloud Platform™, Xilinx™, and Cirrascale™. Examples of processors 2048 include Google's Tensor Processing Unit (TPU)™, rackmount solutions like GX4 Rackmount Series™, GX20 Rackmount Series™, NVIDIA DGX-1™, Microsoft' Stratix V FPGA™, Graphcore's Intelligent Processor Unit (IPU)™, Qualcomm's Zeroth Platform™ with Snapdragon processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 2012 used in the storage subsystem 2002 can include a number of memories including a main random access memory (RAM) 2022 for storage of instructions and data during program execution and a read only memory (ROM) 2024 in which fixed instructions are stored. A file storage subsystem 2026 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2026 in the storage subsystem 2002, or in other machines accessible by the processor.

Bus subsystem 2036 provides a mechanism for letting the various components and subsystems of computer system 2000 communicate with each other as intended. Although bus subsystem 2036 is shown schematically as a single bus, alternative implementations of the bus subsystem can use multiple busses.

Computer system 2000 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 2000 depicted in FIG. 20 is intended only as a specific example for purposes of illustrating the preferred implementations of the present invention. Many other configurations of computer system 2000 are possible having more or less components than the computer system depicted in FIG. 20.

In various implementations, a learning system is provided. In some implementations, a feature vector is provided to a learning system. Based on the input features, the learning system generates one or more outputs. In some implementations, the output of the learning system is a feature vector. In some implementations, the learning system comprises an SVM. In other implementations, the learning system comprises an artificial neural network. In some implementations, the learning system is pre-trained using training data. In some implementations training data is retrospective data. In some implementations, the retrospective data is stored in a data store. In some implementations, the learning system may be additionally trained through manual curation of previously generated outputs.

In some implementations, the sequence generator 172 is a trained classifier. In some implementations, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

FIG. 20 is a schematic of an exemplary computing node. Computing node 2000 is only one example of a suitable computing node and is not intended to suggest any limitation as to the scope of use or functionality of embodiments described herein. Regardless, computing node 2000 is capable of being implemented and/or performing any of the functionality set forth hereinabove.

In computing node 2000 there is a computer system/server, which is operational with numerous other general purpose or special purpose computing system environments or configurations. Examples of well-known computing systems, environments, and/or configurations that may be suitable for use with computer system/server include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed computing environments that include any of the above systems or devices, and the like.

Computer system/server may be described in the general context of computer system-executable instructions, such as program modules, being executed by a computer system. Generally, program modules may include routines, programs, objects, components, logic, data structures, and so on that perform particular tasks or implement particular abstract data types. Computer system/server may be practiced in distributed computing environments where tasks are performed by remote processing devices that are linked through a communications network. In a distributed computing environment, program modules may be located in both local and remote computer system storage media including memory storage devices.

As shown in FIG. 20, computer system/server in computing node 2000 is shown in the form of a general-purpose computing device. The components of computer system/server may include, but are not limited to, one or more processors or processing units, a system memory, and a bus that couples various system components including system memory to processor.

The Bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server typically includes a variety of computer system readable media. Such media may be any available media that is accessible by computer system/server, and it includes both volatile and non-volatile media, removable and non-removable media.

System memory can include computer system readable media in the form of volatile memory, such as random access memory (RAM) and/or cache memory. Algorithm Computer system/server may further include other removable/non-removable, volatile/non-volatile computer system storage media. By way of example only, storage system can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus by one or more data media interfaces. As will be further depicted and described below, memory may include at least one program product having a set (e.g., at least one) of program modules that are configured to carry out the functions of embodiments of the disclosure.

Program/utility, having a set (at least one) of program modules, may be stored in memory by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments as described herein.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages. such as the "C" programming language or similar programming languages. The computer readable program instructions may execute entirely on the user's computer. partly on the user's computer. as a stand-alone software package. partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some implementations, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to implementations of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIG.s illustrate the architecture, functionality, and operation of possible implementations of systems, methods, and computer program products according to various implementations of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reinforcement Learning with Human Feedback (RLHF)

RLHF incorporates human input into the RL process to improve learning efficiency, adaptability, and safety. In basic RL frameworks, an agent learns to make decisions by interacting with an environment. The agent receives feedback in the form of rewards or penalties based on its actions, guiding the agent towards optimal behavior.

Basic RL faces several challenges. First, some tasks have sparse or delayed rewards that can make RL learning slow or difficult. Second, the trade-offs between RL exploration and RL exploitation can be difficult. More specifically, it may be difficult to achieve effective RL learning, as it can be difficult to balance exploration of new strategies with exploitation of known good strategies.

To address these challenges, human feedback is incorporated into RL in several ways. First, in the form of reward shaping, wherein humans can provide additional reward signals or modify existing ones to guide the agent more effectively. Reward shaping can speed up basic RL learning by providing more informative feedback. Second, human feedback can be incorporated into basic RL by imitation learning. Imitation learning refers to the concept that humans can demonstrate desired behaviors, and the agent learns by imitating these demonstrations. This reduces exploration, compared to basic RL, in complex or dangerous environments. Third, human feedback can be incorporated into basic RL by feedback on policies. More specifically, humans can provide feedback directly to the agent, regarding the agent's policies or decision-making processes. In turn, direct feedback on policies helps the agent learn faster and avoid costly mistakes.

Human feedback can include several types. For example, human feedback may include Explicit Rewards, wherein humans assign rewards or penalties based on the agent's actions. In other examples, human feedback can include Demonstrations, such that humans demonstrate desired behaviors, and the agent learns from these examples. In some implementations, human feedback entails Preferences, such that humans express preferences or rankings over different actions or outcomes that guide the agent's decision-making. Still in other implementations, human feedback can include Critiques, wherein humans provide feedback on the agent's decisions, in which humans point out the agent's errors in decision-making or suggest improvements to these decisions.

There are multiple ways this human integration into basic RL can be implemented. For example, human integration into basic RL may be implemented via Reward Augmentation, wherein human-provided rewards are combined with intrinsic rewards from the environment to create a more informative signal. In other examples, Inverse Reinforcement Learning (IRL) may be implemented by having the agent infer the underlying reward function from human demonstrations, that allows it to learn complex behaviors. In further examples, human integration may be implemented by Interactive Learning, wherein the agent interacts with humans in real-time, receiving feedback during training episodes.

RLHF may be implemented according to several phases. The first phase, Supervised Fine-Tuning (SFT), provides that RLHF begins with a pre-trained language model that is then fine-tuned on high-quality datasets for specific applications. The next phase, Preference Sampling and Reward Learning, entails collecting human preferences between pairs of language model outputs and using these preferences to learn a reward function, typically employing the Bradley-Terry model. The final phase, Reinforcement Learning Optimization, uses the learned reward function to further fine-tune the language model, focusing on maximizing the reward for the outputs while maintaining proximity to its original training.

The above RLHF phases may utilize, for example, any of the following language models as appropriate: pre-trained protein language model 270, pre-trained DNA language model 470, protein-to-codon translator 150, cluster-by-cluster high yield DNA sequence generator 1460, high-yield codon sequence generator 1620, or others. In addition, the above RLHF may utilize, for example, any of the following fine-tuning components as appropriate: for example, fine-tuning protein language model 300, fine-tuning codon language model 500, or others.

Direct Performance Optimization (DPO)

The language models of the present invention may also be compatible with direct performance optimization (DPO), a parameterization method of the reward model in RLHF, that enables the extraction of the corresponding optimal policy in a closed form. The DPO approach simplifies the RLHF problem to a simple classification loss, making the algorithm stable, performant, and computationally lightweight.

In the present invention, DPO may combine the reward function and language model into a single transformer network. This combined single transformer network, DPO, only requires the language model to be trained, which more directly and efficiently aligns the combined single transformer with human preferences. The combined single transformer network based on DPO, can deduce which reward function the language model can best maximize, thereby streamlining the entire process.

Performance Results as Objective Indicia of Inventiveness and Non-Obviousness

Figure 21:
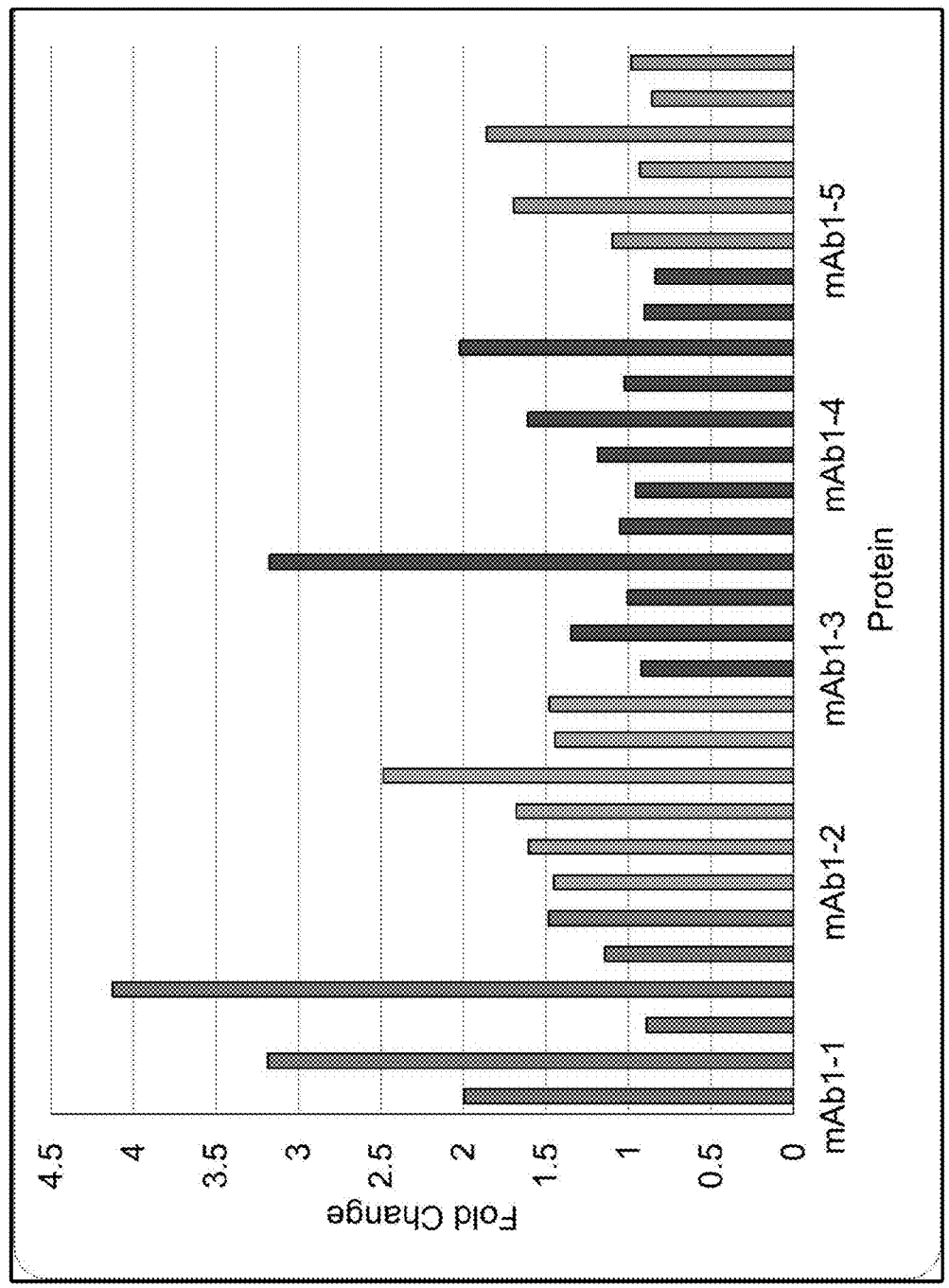
FIG. 21 includes a chart that shows the fold-change in yield/expression for five proteins that were each expressed in the HEK293 cell line.

FIG. 21 includes a chart that shows the fold-change in yield/expression for five proteins that were each expressed in the HEK293 cell line. As shown in FIG. 21, each of the five proteins has at least two variants with a 1.5- to 2-fold or more increase in protein expression relative to the wild type/reference sequence, demonstrating the successful performance of the protein-to-codon sequence mapping system. In fact, two of the proteins had variants with at least a 3- to 4-fold increase in protein expression.

Figure 22:
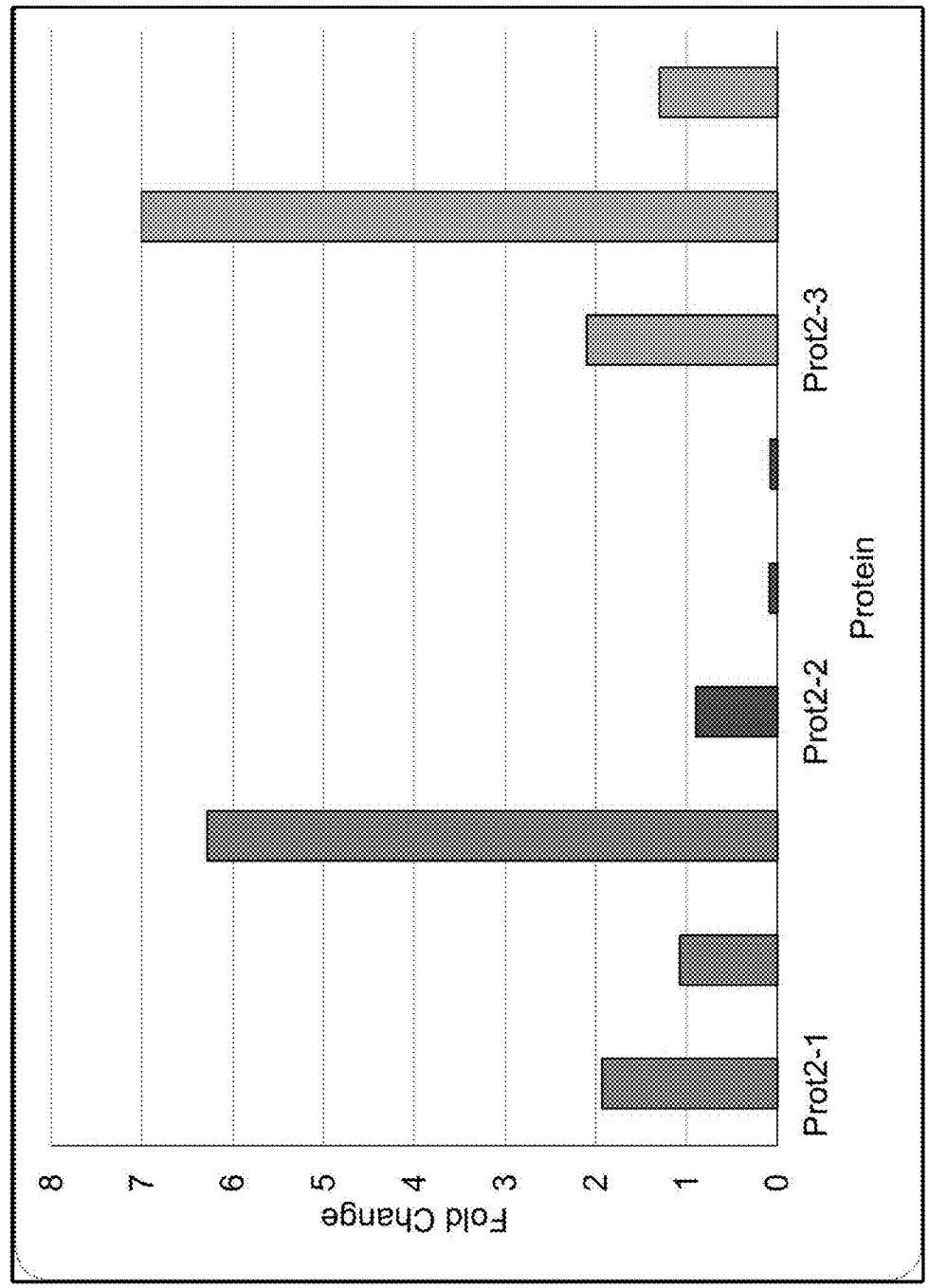
FIG. 22 includes a chart that shows the fold-change in yield/expression for three proteins that were each expressed in the Yeast Pichia cell line.

FIG. 22 includes a chart that shows the fold-change in yield/expression for three proteins that were each expressed in the Yeast Pichia cell line. As shown in FIG. 22, two of the three proteins have at least two variants with a 1.5- to 2-fold or more increase in protein expression relative to the wild type/reference sequence, demonstrating the successful performance of the protein-to-codon sequence mapping system. In fact, two of the proteins had variants with at least a 6- to 7-fold increase in protein expression.

Figure 23:
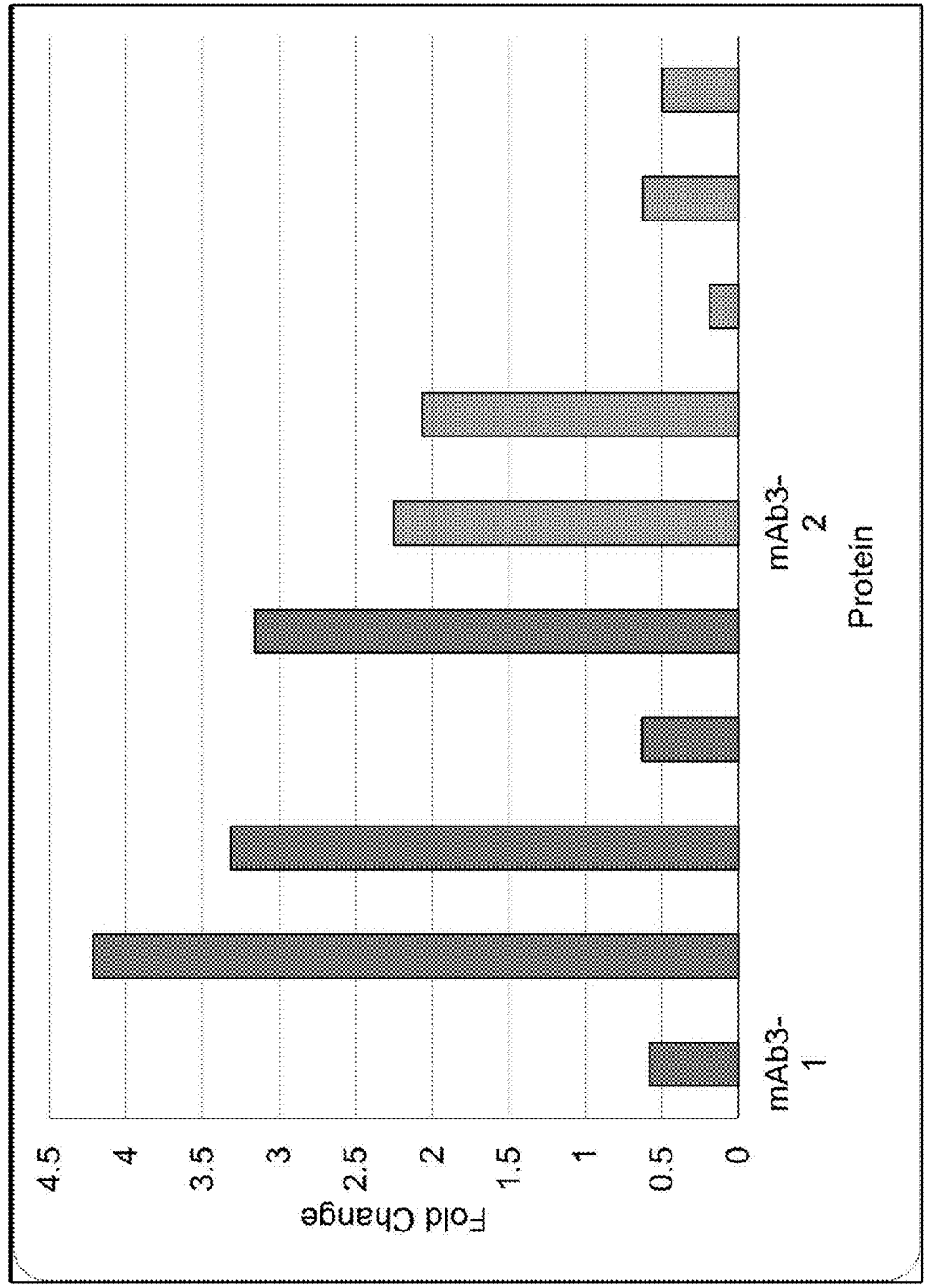
FIG. 23 includes a chart that shows the fold-change in yield/expression for two proteins that were each expressed in the HEK293 cell line.

FIG. 23 includes a chart that shows the fold-change in yield/expression for two proteins that were each expressed in the HEK293 cell line. As shown in FIG. 23, both proteins have at least two variants with a 2-fold or more increase in protein expression relative to the wild type/reference sequence, demonstrating the successful performance of the protein-to-codon sequence mapping system. In fact, one protein had three of the six variants exhibit at least a 3- to 4-fold increase in protein expression.

FIG. 24 includes a table that shows the fold-change in yield/expression for two protein classes, each with several corresponding proteins, that were each expressed in the CHO cell line. As shown in table of FIG. 23, three of the five mAb proteins have at least one variant with a 7-fold or more increase in protein expression relative to the wild type/reference sequence, demonstrating the hugely successful performance of the protein-to-codon sequence mapping system. In fact, two proteins had two of their three variants exhibit at least a 26-fold increase in protein expression, with one variant even reaching a 65-fold increase in protein expression. As shown in table of FIG. 24, three of the four VHH4 proteins have at least one variant with a 1.3-fold or more increase in protein expression relative to the wild type/reference sequence, demonstrating the successful performance of the protein-to-codon sequence mapping system FIG. 25A includes a table that shows the fold-change in yield/expression for the first of two protein classes, each with several corresponding protein indices, that were each expressed in the HEK293 cell line. As shown in table of FIG. 25A, four of the five VHH4 proteins have at least one variant with a 2-fold or more increase in protein expression relative to the wild type/reference sequence, demonstrating the successful performance of the protein-to-codon sequence mapping system.

Figure 25B:
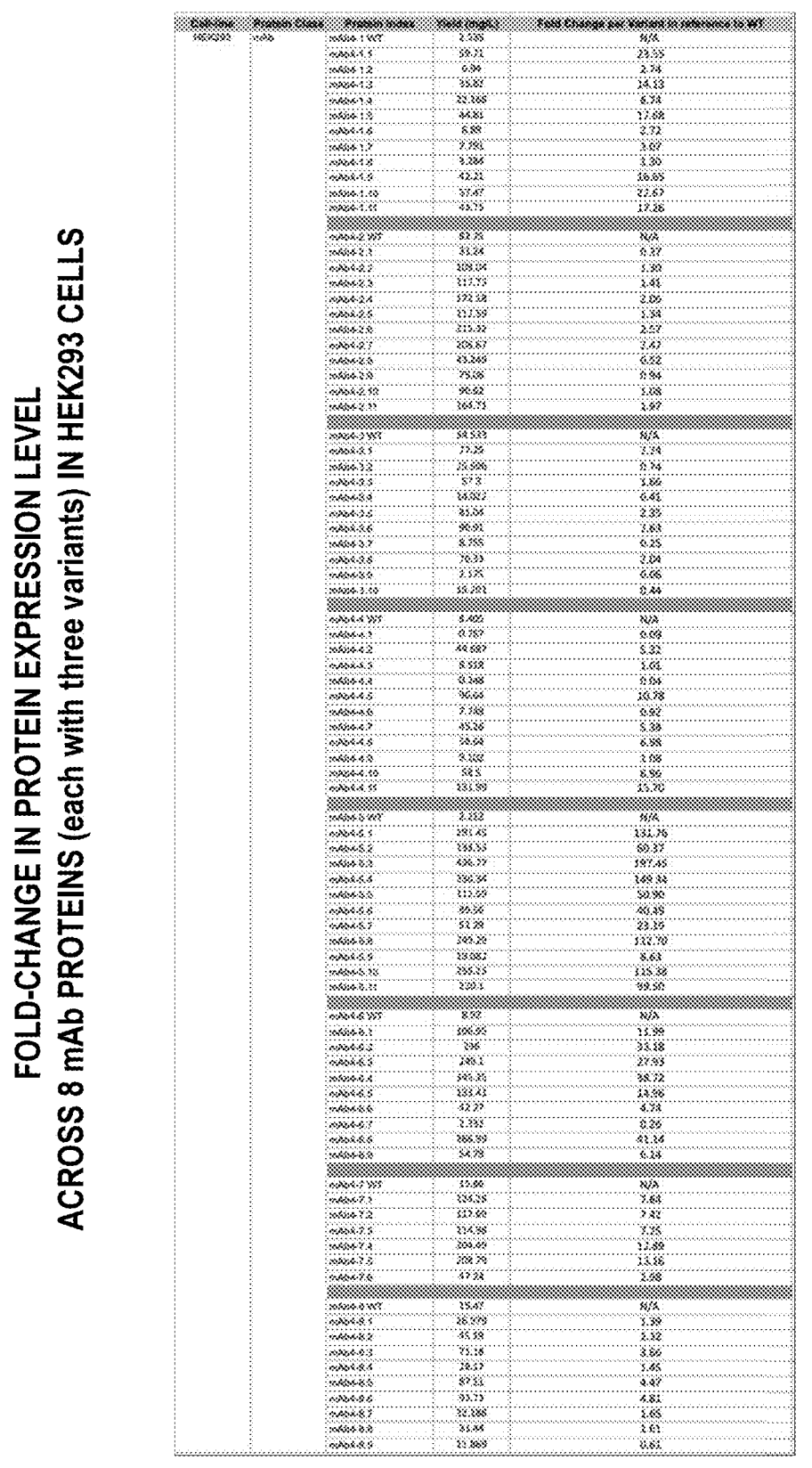

FIG. 25B includes a table that shows the fold-change in yield/expression for the second of two protein classes, each with several corresponding proteins, that were each expressed in the HEK293 cell line. As shown in table of FIG. 25B, all of the eight mAb proteins have at least one variant with a 2-fold or more increase in protein expression relative to the wild type/reference sequence, demonstrating the hugely successful performance of the protein-to-codon sequence mapping system. In fact, five of the eight proteins had one or more variants exhibit at least a 10-fold increase in protein expression, with three proteins having one or more variants with at least a 20-fold increase in protein expression, and one particularly striking protein had five variants reach at least a 100-fold increase in protein expression.

Clauses

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

We disclose the following clauses:

Clause Set 1

1. A system, comprising:
    memory storing an inference protein sequence that requires translation from a protein input space to a codon output space;
    a protein embedder configured to generate an inference protein embedding in response to processing the inference protein sequence through protein embedding coefficients trained to encode the inference protein sequence in a higher-dimensional protein latent space,
        wherein the inference protein embedding is M-dimensional,
        wherein the inference protein sequence is N-dimensional, and
        wherein $M \gg N$;
    a protein-to-codon translator configured with translation coefficients trained using training protein and codon embedding pairs that are higher-dimensional representations of corresponding training protein and codon pairs,
        wherein the training protein and codon embedding pairs are M-dimensional, wherein the training protein and codon pairs are N-dimensional, and
wherein M>>N;
an inference logic configured to process the inference protein embedding through the translation coefficients, and cause the protein-to-codon translator to generate an inference codon embedding; and
a reverse mapping logic configured to process the inference codon embedding through the translation coefficients, and cause the protein-to-codon translator to generate an inference codon sequence that is a translation of the inference protein sequence in the codon output space,
wherein the inference codon embedding is M-dimensional,
wherein the inference codon sequence is N-dimensional, and
wherein M>>N.

The translation coefficients take into account the protein and codon embeddings to output the codon sequence. The reverse mapping logic is configured to process the inference codon embedding and inference protein embeddings through the translation coefficients (e.g., transformer model, cross-attention layer), and cause the protein-to-codon translator to generate the inference codon sequence that is a translation of the inference protein sequence in the codon output space. In other implementations, the translation coefficients can also be referred to as translation deep learning modules, translation neural networks layers, and translation backbone. The codon embeddings do not need to have the same dimensionality as the protein embeddings.

2. The system of clause 1, wherein the protein embedder is a pre-trained protein language model that generates training protein embeddings in the training protein and codon embedding pairs in response to processing corresponding proteins in the training protein and codon pairs.

3. The system of clause 2, wherein the training protein embeddings are extracted from the higher-dimensional protein latent space of the pre-trained protein language model.

4. The system of clause 2, wherein the pre-trained protein language model is pre-trained on large-scale multi-species and multi-protein training datasets.

5. The system of clause 1, wherein a codon embedder is a pre-trained gene/DNA language model that generates training codon embeddings in the training protein and codon embedding pairs in response to processing corresponding codons in the training protein and codon pairs.

The language models can be tokenized at both the codon and the nucleotide level.

6. The system of clause 5, wherein the training codon embeddings are extracted from a higher-dimensional codon latent space of the pre-trained DNA language model.

7. The system of clause 5, wherein the pre-trained DNA language model is pre-trained on large-scale multi-species and multi-DNA training datasets.

8. The system of clause 6, wherein the training datasets used to pre-train the pre-trained protein language model and the pre-trained DNA language model to generate the higher-dimensional protein latent space and the higher-dimensional codon latent space are orders of magnitude larger than training datasets used to train the translation coefficients.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

9. The system of clause 6, wherein computational resources used to pre-train the pre-trained protein language model and the pre-trained DNA language model to generate the higher-dimensional protein latent space and the higher-dimensional codon latent space are orders of magnitude larger than computational resources used to train the translation coefficients.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

10. The system of clause 9, wherein computational resources used to train the translation coefficients on the training protein and codon embedding pairs are orders of magnitude smaller than computational resources used to train the translation coefficients on the training protein and codon pairs.

11. The system of clause 9, wherein training datasets used to train the translation coefficients on the training protein and codon embedding pairs are orders of magnitude smaller than training datasets used to train the translation coefficients on the training protein and codon pairs.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

12. The system of clause 1, wherein the translation coefficients are trained using a supervised machine translation technique.

13. The system of clause 12, wherein the supervised machine translation technique trains the translation coefficients to process the training protein embeddings as inputs and generate the training codon embeddings as target outputs.

14. The system of clause 12, wherein the protein-to-codon translator is a sequence-to-sequence (Seq2Seq) model.

15. The system of clause 14, wherein the Seq2Seq model comprises an encoder network, a latent space, and a decoder network.

16. The system of clause 15, wherein the encoder network is a pre-trained encoder-only language model.

17. The system of clause 15, wherein the decoder network is a pre-trained decoder-only language model. In other implementations, the technology disclosed can use non-pre-trained Seq2Seq models.

18. The system of clause 15, wherein the encoder and decoder networks are combined in a pre-trained encoder-decoder language model.

19. The system of clause 1, wherein the translation coefficients are trained using an unsupervised conditional generation technique.

20. The system of clause 19, wherein the unsupervised conditional generation technique trains the translation coefficients to process concatenations of the training protein embeddings and the training codon embeddings as inputs and generate the training codon embeddings as target outputs.

21. The system of clause 20, wherein the protein-to-codon translator is a variational autoencoder (VAE).
22. The system of clause 20, wherein the protein-to-codon translator is a generative adversarial network (GAN).
23. The system of clause 20, wherein the protein-to-codon translator is a diffusion model.
24. The system of clause 1, wherein the protein-to-codon translator is different from the protein embedder.
25. The system of clause 5, wherein the protein-to-codon translator is different from the codon embedder.
26. The system of clause 24, wherein the protein-to-codon translator is same as the protein embedder.
27. The system of clause 25, wherein the protein-to-codon translator is same as the codon embedder.
28. The system of clause 1, wherein the training protein and codon pairs belong to a same host organism, and therefore make the protein-to-codon translator host organism-specific.

In other implementations, a multi-host/cell line model can be used. In different implementations, the model can be cell-line specific, host-specific, class-specific (e.g., mammalian), and multi-host/multi-class.

29. The system of clause 28, wherein the inference codon sequence satisfies a cell-line/host/class organism-type constraint.
30. The system of clause 28, further configured to provide respective protein-to-codon translators that are specific to respective host organisms based on separately training the respective protein-to-codon translators on respective training protein and codon pairs that belong to the respective host organisms.
31. The system of clause 28, further configured to include host organism filtering logic that predicts cell-line/host/class organism-types for inference codon sequences, and prunes those ones of the inference codon sequences that are a predicted to belong to a cell-line/host/class organism-type different than a target cell-line/host/class organism-type.
32. The system of clause 1, wherein the training protein and codon pairs belong to a same protein-type, and therefore make the protein-to-codon translator protein-specific.
33. The system of clause 32, wherein the inference codon sequence satisfies a protein-type constraint.
34. The system of clause 32, further configured to provide respective protein-to-codon translators that are specific to respective proteins based on separately training the respective protein-to-codon translators on respective training protein and codon pairs that belong to the respective proteins.
35. The system of clause 32, further configured to include protein filtering logic that predicts cell-line/host/class protein-types for inference codon sequences, and prunes those ones of the inference codon sequences that are a predicted to belong to a cell-line/host/class protein-type different than a target cell-line/host/class protein-type.
36. A computer-implemented method, including:
    generating an inference protein embedding in response to processing an inference protein sequence through a protein embedder's protein embedding coefficients that are trained to encode the inference protein sequence in a higher-dimensional protein latent space,
    wherein the inference protein sequence requires translation from a protein input space to a codon output space (e.g., via an intermediate protein embedding space),
    wherein the inference protein embedding is M-dimensional,
    wherein the inference protein sequence is N-dimensional, and
    wherein $M \gg N$;
    processing the inference protein embedding through translation coefficients of a protein-to-codon translator, and causing the protein-to-codon translator to generate an inference codon embedding,
    wherein the translation coefficients are trained using training protein and codon embedding pairs that are higher-dimensional representations of corresponding training protein and codon pairs,
    wherein the training protein and codon embedding pairs are M-dimensional, and
    wherein the training protein and codon pairs are N-dimensional, and
    wherein $M \gg N$;
    processing the inference codon embedding through the translation coefficients, and causing the protein-to-codon translator to generate an inference codon sequence that is a translation of the inference protein sequence in the codon output space,
    wherein the inference codon embedding is M-dimensional,
    wherein the inference codon sequence is N-dimensional, and
    wherein $M \gg N$.

The translation coefficients take into account the protein and codon embeddings to output the codon sequence. The reverse mapping logic is configured to process the inference codon embedding and inference protein embeddings through the translation coefficients (e.g., transformer model, cross-attention layer), and cause the protein-to-codon translator to generate the inference codon sequence that is a translation of the inference protein sequence in the codon output space. In other implementations, the translation coefficients can also be referred to as translation deep learning modules, translation neural networks layers, and translation backbone.

The codon embeddings do not need to have the same dimensionality as the protein embeddings.

37. The computer-implemented method of clause 36, wherein the protein embedder is a pre-trained protein language model that generates training protein embeddings in the training protein and codon embedding pairs in response to processing corresponding proteins in the training protein and codon pairs.
38. The computer-implemented method of clause 37, wherein the training protein embeddings are extracted from the higher-dimensional protein latent space of the pre-trained protein language model.
39. The computer-implemented method of clause 37, wherein the pre-trained protein language model is pre-trained on large-scale multi-species and multi-protein training datasets.
40. The computer-implemented method of clause 36, wherein a codon embedder is a pre-trained DNA language model that generates training codon embeddings in the training protein and codon embedding pairs in response to processing corresponding codons in the training protein and codon pairs.

The language models can be tokenized at both the codon and the nucleotide level.

41. The computer-implemented method of clause 40, wherein the training codon embeddings are extracted from a higher-dimensional codon latent space of the pre-trained DNA language model.
42. The computer-implemented method of clause 40, wherein the pre-trained DNA language model is pre-trained on large-scale multi-species and multi-DNA training datasets.
43. The computer-implemented method of clause 41, wherein the training datasets used to pre-train the pre-trained protein language model and the pre-trained DNA language model to generate the higher-dimensional protein latent space and the higher-dimensional codon latent space are orders of magnitude larger than training datasets used to train the translation coefficients.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

44. The computer-implemented method of clause 41, wherein computational resources used to pre-train the pre-trained protein language model and the pre-trained DNA language model to generate the higher-dimensional protein latent space and the higher-dimensional codon latent space are orders of magnitude larger than computational resources used to train the translation coefficients.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

45. The computer-implemented method of clause 44, wherein computational resources used to train the translation coefficients on the training protein and codon embedding pairs are orders of magnitude smaller than computational resources used to train the translation coefficients on the training protein and codon pairs.
46. The computer-implemented method of clause 44, wherein training datasets used to train the translation coefficients on the training protein and codon embedding pairs are orders of magnitude smaller than training datasets used to train the translation coefficients on the training protein and codon pairs.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

47. The computer-implemented method of clause 36, wherein the translation coefficients are trained using a supervised machine translation technique.
48. The computer-implemented method of clause 47, wherein the supervised machine translation technique trains the translation coefficients to process the training protein embeddings as inputs and generate the training codon embeddings as target outputs.
49. The computer-implemented method of clause 47, wherein the protein-to-codon translator is a sequence-to-sequence (Seq2Seq) model.
50. The computer-implemented method of clause 49, wherein the Seq2Seq model comprises an encoder network, a latent space, and a decoder network.
51. The computer-implemented method of clause 50, wherein the encoder network is a pre-trained encoder-only language model.
52. The computer-implemented method of clause 50, wherein the decoder network is a pre-trained decoder-only language model.

In other implementations, the technology disclosed can use non-pre-trained Seq2Seq models.

53. The computer-implemented method of clause 50, wherein the encoder and decoder networks are combined in a pre-trained encoder-decoder language model.
54. The computer-implemented method of clause 36, wherein the translation coefficients are trained using an unsupervised conditional generation technique.
55. The computer-implemented method of clause 54, wherein the unsupervised conditional generation technique trains the translation coefficients to process concatenations of the training protein embeddings and the training codon embeddings as inputs and generate the training codon embeddings as target outputs.
56. The computer-implemented method of clause 55, wherein the protein-to-codon translator is a variational autoencoder (VAE).
57. The computer-implemented method of clause 55, wherein the protein-to-codon translator is a generative adversarial network (GAN).
58. The computer-implemented method of clause 55, wherein the protein-to-codon translator is a diffusion model.
59. The computer-implemented method of clause 36, wherein the protein-to-codon translator is different from the protein embedder.
60. The computer-implemented method of clause 40, wherein the protein-to-codon translator is different from the codon embedder.
61. The computer-implemented method of clause 59, wherein the protein-to-codon translator is same as the protein embedder.
62. The computer-implemented method of clause 60, wherein the protein-to-codon translator is same as the codon embedder.
63. The computer-implemented method of clause 36, wherein the training protein and codon pairs belong to a same host organism, and therefore make the protein-to-codon translator host organism-specific.

In other implementations, a multi-host/cell line model can be used. In different implementations, the model can be cell-line specific, host-specific, class-specific (e.g., mammalian), and multi-host/multi-class.

64. The computer-implemented method of clause 63, wherein the inference codon sequence satisfies a cell-line/host/class organism-type constraint.
65. The computer-implemented method of clause 63, further including providing respective protein-to-codon translators that are specific to respective host organisms based on separately training the respective protein-to-codon translators on respective training protein and codon pairs that belong to the respective host organisms.
66. The computer-implemented method of clause 63, further including providing host organism filtering logic that predicts cell-line/host/class organism-types for inference codon sequences, and prunes those ones of the inference codon sequences whose cell-line/host/class organism-type prediction confidence is below a threshold or that are a predicted to belong to a cell-line/host/class organism-type different than a target cell-line/host/class organism-type.
67. The computer-implemented method of clause 36, wherein the training protein and codon pairs belong to a same protein-type, and therefore make the protein-to-codon translator protein-specific.
68. The computer-implemented method of clause 67, wherein the inference codon sequence satisfies a protein-type constraint.
69. The computer-implemented method of clause 67, further including providing respective protein-to-codon translators that are specific to respective proteins based on separately training the respective protein-to-codon translators on respective training protein and codon pairs that belong to the respective proteins (and/or protein type/class).
70. The computer-implemented method of clause 67, further including providing protein filtering logic that predicts cell-line/host/class protein-types for inference codon sequences, and prunes those ones of the inference codon sequences that are a predicted to belong to a cell-line/host/class protein-type different than a target cell-line/host/class protein-type.
71. A non-transitory computer readable storage medium impressed with computer program instructions, the instructions, when executed on a processor, implement a method comprising:
generating an inference protein embedding in response to processing an inference protein sequence through a protein embedder's protein embedding coefficients that are trained to encode the inference protein sequence in a higher-dimensional protein latent space,
wherein the inference protein sequence requires translation from a protein input space to a codon output space,
wherein the inference protein embedding is M-dimensional,
wherein the inference protein sequence is N-dimensional, and
wherein $M >> N$;
processing the inference protein embedding through translation coefficients of a protein-to-codon translator, and causing the protein-to-codon translator to generate an inference codon embedding,
wherein the translation coefficients are trained using training protein and codon embedding pairs that are higher-dimensional representations of corresponding training protein and codon pairs,
wherein the training protein and codon embedding pairs are M-dimensional, and
wherein the training protein and codon pairs are N-dimensional, and
wherein $M >> N$;
processing the inference codon embedding through the translation coefficients, and causing the protein-to-codon translator to generate an inference codon sequence that is a translation of the inference protein sequence in the codon output space,
wherein the inference codon embedding is M-dimensional,
wherein the inference codon sequence is N-dimensional, and
wherein $M >> N$.

The translation coefficients take into account the protein and codon embeddings to output the codon sequence. The reverse mapping logic is configured to process the inference codon embedding and inference protein embeddings through the translation coefficients (e.g., transformer model, cross-attention layer), and cause the protein-to-codon translator to generate the inference codon sequence that is a translation of the inference protein sequence in the codon output space. In other implementations, the translation coefficients can also be referred to as translation deep learning modules, translation neural networks layers, and translation backbone. The codon embeddings do not need to have the same dimensionality as the protein embeddings.

72. The non-transitory computer readable storage medium of clause 71, wherein the protein embedder is a pre-trained protein language model that generates training protein embeddings in the training protein and codon embedding pairs in response to processing corresponding proteins in the training protein and codon pairs.
73. The non-transitory computer readable storage medium of clause 72, wherein the training protein embeddings are extracted from the higher-dimensional protein latent space of the pre-trained protein language model.
74. The non-transitory computer readable storage medium of clause 72, wherein the pre-trained protein language model is pre-trained on large-scale multi-species and multi-protein training datasets.
75. The non-transitory computer readable storage medium of clause 71, wherein a codon embedder is a pre-trained DNA language model that generates training codon embeddings in the training protein and codon embedding pairs in response to processing corresponding codons in the training protein and codon pairs. The language models can be tokenized at both the codon and the nucleotide level.
76. The non-transitory computer readable storage medium of clause 75, wherein the training codon embeddings are extracted from a higher-dimensional codon latent space of the pre-trained DNA language model.
77. The non-transitory computer readable storage medium of clause 75, wherein the pre-trained DNA language model is pre-trained on large-scale multi-species and multi-DNA training datasets.
78. The non-transitory computer readable storage medium of clause 76, wherein the training datasets used to pre-train the pre-trained protein language model and the pre-trained DNA language model to generate the higher-dimensional protein latent space and the higher-dimensional codon latent space are orders of magnitude larger than training datasets used to train the translation coefficients.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

79. The non-transitory computer readable storage medium of clause 76, wherein computational resources used to pre-train the pre-trained protein language model and the pre-trained DNA language model to generate the higher-dimensional protein latent space and the higher-dimensional codon latent space are orders of magnitude larger than computational resources used to train the translation coefficients.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

80. The non-transitory computer readable storage medium of clause 79, wherein computational resources used to train the translation coefficients on the training protein and codon embedding pairs are orders of magnitude smaller than computational resources used to train the translation coefficients on the training protein and codon pairs.

81. The non-transitory computer readable storage medium of clause 79, wherein training datasets used to train the translation coefficients on the training protein and codon embedding pairs are orders of magnitude smaller than training datasets used to train the translation coefficients on the training protein and codon pairs.

In other implementations, the technology disclosed can use non-pre-trained Seq2Seq models. In such implementations, the higher-dimensional protein latent space and the higher-dimensional codon latent space are the same order of magnitude as the training datasets used to train the translation coefficients.

82. The non-transitory computer readable storage medium of clause 71, wherein the translation coefficients are trained using a supervised machine translation technique.

83. The non-transitory computer readable storage medium of clause 82, wherein the supervised machine translation technique trains the translation coefficients to process the training protein embeddings as inputs and generate the training codon embeddings as target outputs.

84. The non-transitory computer readable storage medium of clause 82, wherein the protein-to-codon translator is a sequence-to-sequence (Seq2Seq) model.

85. The non-transitory computer readable storage medium of clause 84, wherein the Seq2Seq model comprises an encoder network, a latent space, and a decoder network.

86. The non-transitory computer readable storage medium of clause 85, wherein the encoder network is a pre-trained encoder-only language model.

87. The non-transitory computer readable storage medium of clause 85, wherein the decoder network is a pre-trained decoder-only language model.

In other implementations, the technology disclosed can use non-pre-trained Seq2Seq models.

88. The non-transitory computer readable storage medium of clause 85, wherein the encoder and decoder networks are combined in a pre-trained encoder-decoder language model.

89. The non-transitory computer readable storage medium of clause 71, wherein the translation coefficients are trained using an unsupervised conditional generation technique.

90. The non-transitory computer readable storage medium of clause 89, wherein the unsupervised conditional generation technique trains the translation coefficients to process concatenations of the training protein embeddings and the training codon embeddings as inputs and generate the training codon embeddings as target outputs.

91. The non-transitory computer readable storage medium of clause 90, wherein the protein-to-codon translator is a variational autoencoder (VAE).

92. The non-transitory computer readable storage medium of clause 90, wherein the protein-to-codon translator is a generative adversarial network (GAN).

93. The non-transitory computer readable storage medium of clause 90, wherein the protein-to-codon translator is a diffusion model.

94. The non-transitory computer readable storage medium of clause 71, wherein the protein-to-codon translator is different from the protein embedder.

95. The non-transitory computer readable storage medium of clause 75, wherein the protein-to-codon translator is different from the codon embedder.

96. The non-transitory computer readable storage medium of clause 94, wherein the protein-to-codon translator is same as the protein embedder.

97. The non-transitory computer readable storage medium of clause 95, wherein the protein-to-codon translator is same as the codon embedder.

98. The non-transitory computer readable storage medium of clause 71, wherein the training protein and codon pairs belong to a same host organism, and therefore make the protein-to-codon translator host organism-specific.

In other implementations, a multi-host/cell line model can be used. In different implementations, the model can be cell-line specific, host-specific, class-specific (e.g., mammalian), and multi-host/multi-class.

99. The non-transitory computer readable storage medium of clause 98, wherein the inference codon sequence satisfies a cell-line/host/class organism-type constraint.

100. The non-transitory computer readable storage medium of clause 98, implementing the method further comprising providing respective protein-to-codon translators that are specific to respective host organisms based on separately training the respective protein-to-codon translators on respective training protein and codon pairs that belong to the respective host organisms.

101. The non-transitory computer readable storage medium of clause 98, implementing the method further comprising providing host organism filtering logic that predicts cell-line/host/class organism-types for inference codon sequences, and prunes those ones of the inference codon sequences whose cell-line/host/class organism-type prediction confidence is below a threshold or that are a predicted to belong to a cell-line/host/class organism-type different than a target cell-line/host/class organism-type.

102. The non-transitory computer readable storage medium of clause 71, wherein the training protein and codon pairs belong to a same protein-type, and therefore make the protein-to-codon translator protein-specific.

103. The non-transitory computer readable storage medium of clause 102, wherein the inference codon sequence satisfies a protein-type constraint.

104. The non-transitory computer readable storage medium of clause 102, implementing the method further comprising providing respective protein-to-codon translators that are specific to respective proteins based on separately training the respective protein-to-codon translators on respective training protein and codon pairs that belong to the respective proteins.

105. The non-transitory computer readable storage medium of clause 102, implementing the method further comprising providing protein filtering logic that predicts cell-line/host/class protein-types for inference codon sequences, and prunes those ones of the inference codon sequences that are a predicted to belong to a cell-line/host/class protein-type different than a target cell-line/host/class protein-type.

Clause Set 2

1. A computer-implemented method of generating optimized codon sequences, including:
   processing an input sequence of amino acid elements; and
   based on the processing, generating an output sequence of codon elements, including:
      for a given amino acid element in the input sequence of amino acid elements, confining search of a corresponding codon element in a vocabulary of codon elements to a subset of codon elements known to translate to the given amino acid element.

In some implementations, given the codon/nucleotide sequence sampling often takes place in a manner that's unrestricted by the protein sequence but rather guided with it, it is probable that the codons/nucleotides sampled by the decoder may not encode back to the original amino acids.

2. The computer-implemented method of clause 1, further including, prior to the search, evaluating at the input sequence of amino acid elements to determine an identity of the given amino acid element, and using the determined identity of the given amino acid element to confine the search of the corresponding codon element to the subset of codon elements known to translate to the given amino acid element.
3. The computer-implemented method of clause 1, wherein a neural network (e.g., AA2DNA) processes the input sequence of amino acid elements, and generates the output sequence of codon elements.
4. The computer-implemented method of clause 1, wherein the neural network is a pre-trained neural network.
5. The computer-implemented method of clause 1, wherein the neural network is trained from scratch.
6. The computer-implemented method of clause 3, wherein the neural network is a sequence to sequence (seq2seq) neural network (e.g., RNNs like LSTMs and GRUs, and also Transformers).
7. The computer-implemented method of clause 3, wherein the neural network is an encoder-decoder neural network (e.g., Transformer).
8. The computer-implemented method of clause 7, wherein an encoder neural network generates respective embedded tokens for respective amino acid elements in the input sequence of amino acid elements.
9. The computer-implemented method of clause 8, wherein the encoder neural network applies attention between the respective embedded tokens on an amino acid element-by-amino acid element.
10. The computer-implemented method of clause 9, wherein a decoder neural network receives results of the attention from the encoder neural network, and uses the results of the attention to generate the output sequence of codon elements.
11. The computer-implemented method of clause 10, wherein the decoder neural network looks back at the input sequence of amino acid elements to determine the identity of the given amino acid element, and uses the determined identity of the given amino acid element to confine the search of the corresponding codon element to the subset of codon elements known to translate to the given amino acid element.
12. A computer-implemented method of generating high-yield codon sequences, including:
   creating clusters of codon sequences on an amino acid sequence-basis, wherein a particular cluster of codon sequences created for a particular amino acid sequence includes different codon sequences that translate to the particular amino acid sequence but have varying yields/expression; and
   using the clusters of codon sequences to build a lower-to-higher yield codon training dataset that links lower-yield input codon sequences to higher-yield target codon sequences by:
      sorting codon sequences within each of the clusters of codon sequences by yield;
      based on the sorting, generating, on a cluster-basis, pairs of codon sequences in which one codon sequence has a lower yield and another codon sequence has a higher yield;
      including the codon sequence with the lower yield in the lower-to-higher yield codon training dataset as a lower-yield input codon sequence; and
      including the codon sequence with the higher yield in the lower-to-higher yield codon training dataset as a higher-yield target codon sequence for the codon sequence with the lower yield.
13. The computer-implemented method of clause 12, further including using the lower-to-higher yield codon training dataset to train a high-yield codon sequence generator to map the lower-yield input codon sequences to the higher-yield target codon sequences.
14. The computer-implemented method of clause 13, wherein the high-yield codon sequence generator is a neural network.
15. The computer-implemented method of clause 14, wherein the neural network is a pre-trained neural network.
16. The computer-implemented method of clause 14, wherein the neural network is trained from scratch.
17. The computer-implemented method of clause 14, wherein the neural network is a sequence to sequence (seq2seq) neural network (e.g., RNNs like LSTMs and GRUs, and also Transformers).
18. The computer-implemented method of clause 17, wherein the neural network is an encoder-decoder neural network (e.g., Transformer).
19. The computer-implemented method of clause 12, wherein at least some of the clusters of codon sequences are generated based on clinical data that identifies different codons sequences that translate to a same amino acid sequence.

In other implementations, at least some of the clusters of codon sequences are generated based on "labeled data" that can use transcriptomic labeling a proteomic labeling.

20. The computer-implemented method of clause 12, wherein at least some of the clusters of codon sequences are generated based on an amino acid sequence-to-codon sequence generator generating different output codon sequences for a same input amino acid sequence.

21. The computer-implemented method of clause 20, wherein the amino acid sequence-to-codon sequence generator is a neural network.
22. The computer-implemented method of clause 21, wherein the neural network is a pre-trained neural network.
23. The computer-implemented method of clause 21, wherein the neural network is an untrained neural network.
24. The computer-implemented method of clause 21, wherein the neural network is a sequence to sequence (seq2seq) neural network.
25. The computer-implemented method of clause 24, wherein the neural network is an encoder-decoder neural network (e.g., Transformer).
26. A computer-implemented method of generating optimized codon sequences, including:
   processing an input sequence of amino acid elements; and
   based on the processing, generating an output sequence of codon elements, including confining sampling of the codon elements to map back to the amino acid elements.
27. A system, comprising:
   a high-yield codon sequence generator trained on a lower-to-higher yield codon training dataset, and configured to generate output codon sequences in response to processing input codon sequences, wherein the output codon sequences have yields higher than that of the input codon sequences.
28. A computer-implemented method of generating high-yield codon sequences, including:
   using a pre-trained protein language model to process amino acid sequences and generate codon sequence embeddings;
   using a pre-trained DNA language model to process codon sequences and generate amino acid sequence embeddings;
   using the amino acid sequence embeddings as inputs and the codons sequence embeddings as targets to train an amino acid sequence-to-codon sequence generator to generate clusters of variant codon sequences that translate to a same amino acid sequence;
   sorting the variant codon sequences by yield and using the sorted variant codon sequences to build a lower-to-higher yield codon training dataset that links lower-yield input codon sequences to higher-yield target codon sequences; and
   using the lower-to-higher yield codon training dataset to train a high-yield codon sequence generator to map the lower-yield input codon sequences to the higher-yield target codon sequences.
29. A computer-implemented method of providing a relative positional embedding to a multi-head attention transformer model, including:
   using respective attention heads of the multi-head attention transformer model to generate query, key, and value vectors for inputs tokens;
   converting the query and key vectors into position-encoded query and key vectors by applying a series of rotation matrices to the query and key vectors at different scaled frequencies that vary by absolute positions of the query and key vectors and by the respective attention heads, wherein the application of the series of rotation matrices includes:
   rotating pairs of feature dimensions in the query and key vectors by an angle in multiples of a scaled position index of a corresponding query or key vector, wherein the scaled position index is scaled by a head-specific scaling parameter that varies across the respective attention heads; and
   using the position-encoded query and key vectors for execution of self-attention by the respective attention heads to generate pairwise attention scores that depend on relative positions of input token pairs and on their feature similarity.
30. The computer-implemented method of clause 29, wherein the head-specific scaling parameter is a head-specific scaling scalar.
31. The computer-implemented method of clause 29, wherein the pairwise attention scores are penalized based on how far the position-encoded query and key vectors are.
32. The computer-implemented method of clause 31, wherein when a position-encoded query vector and a position-encoded key vector are close by, the penalty is very low.
33. The computer-implemented method of clause 31, wherein when a position-encoded query vector and a position-encoded key vector are far away, the penalty is very high.
34. The computer-implemented method of clause 29, wherein the input token pairs are amino acid token pairs.
35. The computer-implemented method of clause 29, wherein the input token pairs are nucleotide token pairs.

What is claimed is:
1. A system, comprising:
   memory storing an inference protein sequence that requires translation from a protein input space to a codon output space;
   a protein embedder configured to process the inference protein sequence through protein embedding coefficients to generate an inference protein embedding, wherein the protein embedding coefficients are trained to encode the inference protein sequence in a higher-dimensional protein latent space,
      wherein each instance of the inference protein embedding is M-dimensional,
      wherein each instance of the inference protein sequence is N-dimensional, and
      wherein M is greater than N;
   a protein-to-codon translator configured with translation coefficients trained using training protein and codon embedding pairs that are higher-dimensional representations of corresponding training protein and codon pairs,
      wherein the protein-to-codon translator is an encoder-decoder neural network configured with an encoder neural network and a decoder neural network, and wherein the protein-to-codon translator provides an embedding space that generates the higher-dimensional representations,
      wherein each of the training protein and codon embedding pairs are M-dimensional,
      wherein each of the training protein and codon pairs are N-dimensional, and
      wherein M is greater than N;
   an inference logic configured to process the inference protein embedding through the translation coefficients by sampling the embedding space using the protein-to-codon translator to generate an inference codon embedding; and a reverse mapping logic configured to process the inference codon embedding through the translation coefficients by sampling the embedding space using the protein-to-codon translator to generate an inference codon sequence, wherein the inference codon sequence is a translation of the inference protein sequence in the codon output space, wherein each instance of the inference codon embedding is M-dimensional, wherein each instance of the inference codon sequence is N-dimensional, and wherein M is greater than N.

2. The system of claim 1, wherein the protein embedder is a pre-trained protein language model that generates training protein embeddings in the training protein and codon embedding pairs in response to processing corresponding proteins in the training protein and codon pairs.

3. The system of claim 2, wherein the training protein embeddings are extracted from the higher-dimensional protein latent space of the pre-trained protein language model.

4. The system of claim 2, wherein the pre-trained protein language model is pre-trained on multi-species and multi-protein training datasets.

5. The system of claim 1, wherein a codon embedder is a pre-trained DNA language model that generates training codon embeddings in the training protein and codon embedding pairs in response to processing corresponding codons in the training protein and codon pairs.

6. The system of claim 5, wherein the training codon embeddings are extracted from a higher-dimensional codon latent space of the pre-trained DNA language model.

7. The system of claim 5, wherein the pre-trained DNA language model is pre-trained on multi-species and multi-DNA training datasets.

8. The system of claim 2, wherein the training datasets used to pre-train the pre-trained protein language model and the pre-trained DNA language model to generate the higher-dimensional protein latent space and the higher-dimensional codon latent space are orders of magnitude larger than training datasets used to train the translation coefficients.

9. The system of claim 2, wherein computational resources used to pre-train the pre-trained protein language model and the pre-trained DNA language model to generate the higher-dimensional protein latent space and the higher-dimensional codon latent space are orders of magnitude larger than computational resources used to train the translation coefficients.

10. The system of claim 9, wherein computational resources used to train the translation coefficients on the training protein and codon embedding pairs are orders of magnitude smaller than computational resources used to train the translation coefficients on the training protein and codon pairs.

11. The system of claim 9, wherein training datasets used to train the translation coefficients on the training protein and codon embedding pairs are orders of magnitude smaller than training datasets used to train the translation coefficients on the training protein and codon pairs.

12. The system of claim 1, wherein the translation coefficients are trained using a supervised machine translation technique.

13. The system of claim 12, wherein the supervised machine translation technique trains the translation coefficients to process the training protein embeddings as inputs and generate the training codon embeddings as target outputs.

14. The system of claim 12, wherein the protein-to-codon translator is a sequence-to-sequence (Seq2Seq) model.

15. The system of claim 14, wherein the Seq2Seq model comprises an encoder network, a latent space, and a decoder network.

16. The system of claim 15, wherein the encoder network is a pre-trained encoder-only language model.

17. The system of claim 15, wherein the decoder network is a pre-trained decoder-only language model.

18. The system of claim 15, wherein the encoder and decoder networks are combined in a pre-trained encoder-decoder language model.

* * * * *